US007548792B2

(12) United States Patent
Kumano et al.

(10) Patent No.: US 7,548,792 B2
(45) Date of Patent: Jun. 16, 2009

(54) EQUIVALENT MATERIAL CONSTANT CALCULATION SYSTEM, STORAGE MEDIUM STORING AN EQUIVALENT MATERIAL CONSTANT CALCULATION PROGRAM, EQUIVALENT MATERIAL CONSTANT CALCULATION METHOD, DESIGN SYSTEM, AND STRUCTURE MANUFACTURING METHOD

(75) Inventors: Yutaka Kumano, Sanda (JP); Tetsuyoshi Ogura, Settsu (JP); Toru Yamada, Katano (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/077,879

(22) Filed: Mar. 21, 2008

(65) Prior Publication Data

US 2008/0183322 A1 Jul. 31, 2008

Related U.S. Application Data

(62) Division of application No. 11/259,835, filed on Oct. 27, 2005, now Pat. No. 7,379,780.

(30) Foreign Application Priority Data

| Oct. 29, 2004 | (JP) | ............................. 2004-317052 |
| Apr. 5, 2005 | (JP) | ............................. 2005-109046 |

(51) Int. Cl.
*G06F 17/00* (2006.01)
*G06F 1/02* (2006.01)

(52) U.S. Cl. ............................. 700/98; 700/97; 703/1; 703/14; 716/15

(58) Field of Classification Search .................. 700/97, 700/98; 703/1, 14; 716/15
See application file for complete search history.

(56) References Cited

U.S. PATENT DOCUMENTS 4,742,473 A 5/1988 Shugar et al.

(Continued)

FOREIGN PATENT DOCUMENTS

JP 5-181831 7/1993

(Continued)

*Primary Examiner*—Michael D Masinick
(74) *Attorney, Agent, or Firm*—Hamre, Schumann, Mueller & Larson, P.C.

(57) ABSTRACT

An equivalent material constant calculation system that calculates an equivalent material constant of a structure constituted by a plurality of materials includes a shape data input portion that inputs shape data, a material data input portion that inputs material constant data, a dividing portion that divides the structure into a plurality of small regions, and a small region interior calculation portion that calculates equivalent material constants in the small regions, in which the small region interior calculation portion, based on the shape data and material constant data, with a function that includes a value in a variable that expresses a position in at least one direction in the small region, expresses an equivalent material constant for a region that is a portion of a small region, and using the function, calculates an equivalent material constant for the small region with respect to the at least one direction.

20 Claims, 27 Drawing Sheets

U.S. PATENT DOCUMENTS

| | | |
|---|---|---|
| 5,408,638 A | 4/1995 | Sagawa et al. |
| 5,502,643 A | 3/1996 | Fujinaga |
| 5,966,312 A | 10/1999 | Chen |
| 6,546,528 B1 | 4/2003 | Sasaki et al. |
| 6,718,291 B1 | 4/2004 | Shapiro et al. |
| 2003/0163295 A1 | 8/2003 | Jakatdar et al. |
| 2004/0230411 A1 | 11/2004 | Zheng |

FOREIGN PATENT DOCUMENTS

| | | |
|---|---|---|
| JP | 10-230326 | 9/1998 |
| JP | 2000-180395 | 6/2000 |
| JP | 2004-227337 | 8/2004 |

| | Equivalent material constant | Percentage |
|---|---|---|
| Precise analysis value | 60 | 100% |
| No correction | 110 | 182% |
| Maximum value | 88 | 146% |
| Minimum value | 45 | 75% |
| Arithmetic mean | 68 | 112% |
| Geometric mean | 63 | 104% |

EQUIVALENT MATERIAL CONSTANT CALCULATION SYSTEM, STORAGE MEDIUM STORING AN EQUIVALENT MATERIAL CONSTANT CALCULATION PROGRAM, EQUIVALENT MATERIAL CONSTANT CALCULATION METHOD, DESIGN SYSTEM, AND STRUCTURE MANUFACTURING METHOD

CROSS-REFERENCE TO RELATED MATTERS

This application is a Division of application Ser. No. 11/259,835, filed Oct. 27, 2005, which application is incorporated herein by reference.

BACKGROUND OF THE INVENTION

1. Field of the Invention

The present invention relates to an equivalent material constant calculation system that calculates an equivalent material constant of a structure made from a plurality of materials having different material constants, an equivalent material constant calculation program, an equivalent material constant calculation method, and a design system and manufacturing method for such a structure.

2. Description of Related Art

For example, in the design of electronic equipment, it is possible to model the electronic equipment such that the electronic equipment can be handled as data on a computer, and predict temperature, stress, and the like by performing a simulation that employs, for example, a finite element method.

When modeling electronic equipment, the shape of components that constitute the electronic equipment, the material constant, and the like are necessary as data. For example, the shape of an electronic circuit board that is a component part of the electronic equipment and the material constant (for example, thermal conductivity) are necessary as data. The electronic circuit board is configured of a wired portion made from metal material and a non-wired portion made from resin material. Thus, the electronic circuit board includes metal material and resin material, which are materials with different material constants. In this case, it is not possible to model all of the wires using a computer having present day specifications. Consequently, it is necessary to solve for an equivalent material constant by considering all or a part of the entire electronic circuit board, which is made from a plurality of materials that have different material constants, as a structure made from a plurality of materials that have one equivalent material constant.

As a method of calculating this sort of equivalent material constant, a calculation method of an equivalent thermal conductivity that takes into consideration a wiring pattern on the electronic circuit board is known, as disclosed in JP 2000-180395A. FIG. 26 is a flowchart that shows an overview of an electronic circuit board equivalent thermal conductivity calculation method, and which is an example of this conventional equivalent material constant calculation method.

In Step S911, shape data of the electronic circuit board that is the target of the equivalent thermal conductivity calculation is input. The electronic circuit board is configured by layering a wire pattern layer (hereinafter, referred to as a 'wire layer') and an insulation layer. As shape data, for example, data relating to various shapes is input, such as the outer contour of the entire electronic circuit board, the position and size of holes in the electronic circuit board when such holes exist, the thickness of the wire layer and the insulation layer, and the shape of the wire pattern in each wire layer.

In Step S912, material data of the electronic circuit board is input. As material data, for example, a thermal conductivity of the wire material, which is metal material that constitutes the wire pattern of the electronic circuit board, and a thermal conductivity of the insulation material, which is resin material that constitutes the insulation layer and the non-wire portion that is the portion other than the wire pattern, are input.

In Step S913, the electronic circuit board for which this equivalent thermal conductivity calculation will be performed is divided into a number N of small regions of each wire layer and insulation layer of this electronic circuit board.

In Step S914, the wire pattern surface area and the insulating portion surface area, which is the area other than the wire pattern, are obtained for each divided small region using the shape data of the electronic circuit board that was input in above Step S911, and from both of these surface areas a surface area ratio of the wire portion in each small region is calculated. Ordinarily the electronic circuit board has a very complicated shape, and reflecting this fact, the shape data of this electronic circuit board also is very complicated. However, by dividing the electronic circuit board into small regions, the shape of the wire pattern in those small regions becomes, for example, a straight line or arc, or a square or triangle, or part of a circle, or a shape that can be approximated by at least these shapes. As a result, it is possible to calculate the wire pattern surface area and the other, insulation portion surface area with relative ease and high accuracy.

In Step S915, by adding up the wire portion surface area ratio of these divided N-small regions, a wire portion surface area ratio is calculated for each wire layer or insulation layer. The formula for obtaining the wire portion surface area ratio for each of these layers is shown in formula 1. Pi in formula 1 indicates the wire portion surface area ratio of a layer No. i.

$$P_i = \sum_{j=1}^{N} p_{ij} / N \quad \text{Formula 1}$$

In formula 1, $P_{ij}$ is the wire portion surface area ratio of a small region No. j of the layer No. i.

This formula obtains an average of the wire portion surface area ratios of each small region. However, here it is assumed that the surface area of the divided small regions is equal.

In Step S916, an equivalent thermal conductivity λp of the entire electronic circuit board that is regarded as lamination material is calculated using the wire portion surface area ratio calculated for each of the wire and insulation layers.

It is possible to use formula 2 or formula 3 for this calculation of λp. Formula 2 is a formula for a case in which the thermal conductivity effect of the insulator material is ignored. Ordinarily, the thermal conductivity of the insulator material is very small in comparison to the thermal conductivity of the wire material, and so it is possible to lighten the calculation load by ignoring the thermal conductivity effect of the insulator material as in formula 2. Formula 3 is a formula for a case in which the thermal conductivity effect of the insulator material is taken into consideration.

$$\lambda_p = \sum_i (\lambda_i P_i \alpha_i) \quad \text{Formula 2}$$

-continued $$\lambda_p = A + B \qquad \text{Formula 3}$$

$$A = \sum ((\lambda_A P_i + \lambda_B (1 - P_i))\alpha_i) \left(\sum \text{ is wire layer sum only}\right)$$

$$B = \sum (\lambda_B \alpha_i) \left(\sum \text{ is insulation layer sum only}\right)$$

In Formula 2, $\lambda_i$, $P_i$, and $\alpha_i$ indicate the following values:
$\lambda_i$: thermal conductivity of the wire material of layer No. i (W/m·K)
$P_i$: wire portion surface area ratio of layer No. i (0.0 for the insulation layer)
$\alpha_i$: ratio at which the thickness of layer No. i accounts for the thickness of the entire electronic circuit board (see Formula 4).

$$\sum_i \alpha_i = 1 \qquad \text{Formula 4}$$

In formula 3, $\lambda_A$ and $\lambda_B$ indicate the following values. $P_i$ and $\alpha_i$ are the same as in formula 2.
$\lambda_A$: thermal conductivity of the wire material (W/m·K)
$\lambda_B$: thermal conductivity of the insulator material (W/m·K)

In formula 3, portions of the wire material that are included in the insulation layer (such as through holes) are ignored. If portions of the wire material that are included in the insulation layer also are considered, then it is possible to perform the calculation for B in formula 3 in the same manner as the calculation for A.

Further, in formula 3, it is assumed that the wire material of each layer and also the insulator material of each layer are the same (or at least that the thermal conductivity of the wire material of each layer is the same, and that the thermal conductivity of the insulator material of each layer is the same).

In Step S917, equivalent thermal conductivity information for the entire electronic circuit board that was calculated in Step S916 is output to a thermal conductivity database or the like. The equivalent thermal conductivity saved in the thermal conductivity database afterwards can be read and used when performing a thermal conductivity analysis that employs a finite element method or the like.

However, in the conventional equivalent material constant calculation method described above, an equivalent material constant is calculated using a surface area ratio of the occupied surface area of each electronic material (wire material and insulator material), but the directionality of the shape of the portion occupied by each electronic material on the electronic circuit board is not considered at all.

Even assuming that a particular electronic material occupies the same surface area on one board, the equivalent material constant differs greatly according to the directionality of the shape of the portion on that board that is occupied by that electronic material.

FIG. 27 shows an example of a wire pattern of an electronic circuit board. For example, in an electronic circuit board 921 shown in FIG. 27A, a wire pattern 923 constituted by wire material that is a good thermal conductor occupies a long and narrow surface area along the direction of the X axis, and six strips of that wire material are present. In this electronic circuit board 921, for example, when heat is transmitted in the direction of the X axis, the transmission of heat is good because it is transmitted from one side to the opposite side through the wire pattern 923, which is a good thermal conductor. On the other hand, when heat is transmitted in the direction of axis Y, the transmission of heat becomes poor because it is transmitted alternately through the wire pattern 923 and the non-wire portion 924. Accordingly, the equivalent thermal conductivity is comparatively high in the direction of the X axis, and comparatively low in the direction perpendicular to direction X (the direction of the Y axis).

Conversely, as in an electronic circuit board 922 shown in FIG. 27B, when the wire pattern 923, which is constituted by wire material that is a good thermal conductor, occupies a long and narrow surface area along the direction of the Y axis and is present in seven strips, the thermal conductivity becomes comparatively high in the direction of the Y axis, and comparatively low in the direction of the X axis, which is perpendicular to the Y axis.

Because the equivalent material constant that can be obtained by the conventional equivalent material constant calculation method described above is calculated using a surface area ratio of the occupied surface area, the directionality of the shape of the portion occupied by each electronic material on the electronic circuit board is not taken into consideration at all. Thus, for example, as shown in FIGS. 27A and 27B, when the shape of the portion occupied by each material is anisotropic, the calculated equivalent material constant cannot avoid an extremely large error.

As one approach for solving this problem, for example, it has been conceived to divide the electronic circuit board into even smaller regions and obtain an equivalent material constant for each of the divided small regions, thereby reducing the size of the error. However, this approach makes a greater amount of calculation time necessary. Also, because the equivalent material constant for each small region does not take into consideration the different directionality of the shape of the portion that each electronic material occupies, this method has little effectiveness for increasing the accuracy of an equivalent material constant having anisotropy. Thus, there is the problem that the effectiveness of calculation processing worsens.

Also, when the electronic circuit board is finely divided, the amount of data output as calculation results becomes large because as many equivalent material constants are output as there are divided small regions. Thus, analysis processing also becomes complicated when analysis is performed using the output equivalent material constants, and the effectiveness worsens.

SUMMARY OF THE INVENTION

Therefore, with the foregoing in mind, it is an object of the present invention to provide an equivalent material constant calculation system in which it is possible to calculate with good effectiveness a highly accurate equivalent material constant that takes into consideration the directionality of each material in a structure constituted by a plurality of materials, an equivalent material constant calculation program, an equivalent material constant calculation method, and also a design system and manufacturing method for that sort of structure.

An equivalent material constant calculation system according to the present invention calculates an equivalent material constant of a structure constituted by a plurality of materials, and includes a shape data input portion that inputs shape data that expresses the shape of each material constituting the structure, a material data input portion that inputs material constant data that expresses a material constant of at least one of the materials constituting the structure, a dividing portion that divides the structure into a plurality of small regions, and a small region interior calculation portion that calculates equivalent material constants in the small regions, wherein the small region interior calculation portion, based on the shape data and material constant data, expresses an equivalent material constant for a region that is part of a small region, with a function that includes a value in a variable that expresses a location in at least one direction in the small regions, and using the function, calculates equivalent material constants in the small region with respect to the at least one direction.

An equivalent material constant calculation system according to the present invention calculates an equivalent material constant of a structure constituted by a plurality of materials, and includes a shape data input portion that inputs shape data that expresses the shape of each material constituting the structure, a material data input portion that inputs material constant data that expresses a material constant of at least one of the materials constituting the structure, a dividing portion that divides the structure into a plurality of small regions, and a small region interior calculation portion that calculates constituent ratios of the materials included in the small regions based on the shape data, and calculates equivalent material constants in the small regions based on the constituent ratios and the material constant data, and a combining portion that, based on the equivalent material constants for the small region, obtains an equivalent material constant for a region in which a plurality of the small regions that are adjacent are combined.

An equivalent material constant calculation program stored on a storage medium according to the present invention allows a computer to execute processing that calculates an equivalent material constant of a structure constituted by a plurality of materials, the processing including shape data input processing that inputs shape data that expresses the shape of each material constituting the structure, material data input processing that inputs material constant data that expresses a material constant of at least one of the materials constituting the structure, dividing processing that divides the structure into a plurality of small regions, and small region interior calculation processing that calculates equivalent material constants in the small regions. The small region interior calculation processing, based on the shape data and material constant data, expresses an equivalent material constant for a region that is a portion of a small region, with a function that includes a value in a variable that expresses a position in at least one direction in the small regions, and using the function, calculates an equivalent material constant for the small region with respect to the at least one direction.

An equivalent material constant calculation program stored on a storage medium according to the present invention allows a computer to execute processing that calculates an equivalent material constant of a structure constituted by a plurality of materials. The processing includes shape data input processing that inputs shape data that expresses the shape of each material constituting the structure, material data input processing that inputs material constant data that expresses a material constant of at least one of the materials constituting the structure, dividing processing that divides the structure into a plurality of small regions, small region interior calculation processing that calculates constituent ratios of the materials included in the small region based on the shape data, and calculates an equivalent material constant for the small region based on the constituent ratio and the material constant data, and combining processing that, based on the equivalent material constant for the small region, obtains an equivalent material constant for a region in which a plurality of the small regions that are adjacent are combined.

An equivalent material constant calculation method according to the present invention calculates an equivalent material constant of a structure constituted by a plurality of materials using a computer. The method includes a shape data input step in which a shape data input portion provided by the computer inputs shape data that expresses the shape of each material constituting the structure, a material data input step in which a material data input portion provided by the computer inputs material constant data that expresses a material constant of at least one of the materials constituting the structure, a dividing step in which a dividing portion provided by the computer divides the structure into a plurality of small regions, and a small region interior calculation step in which a small region interior calculation portion provided by the computer calculates equivalent material constants in the small regions, in which in the small region interior calculation step, a small region interior calculation portion, based on the shape data and material constant data, expresses an equivalent material constant for a region that is a portion of a small region, with a function that includes a value in a variable that expresses a location in the small region in at least one direction, and using the function, calculates an equivalent material constant for the small region with respect to the at least one direction An equivalent material constant calculation method according to the present invention calculates an equivalent material constant of a structure constituted by a plurality of materials using a computer. The method includes a shape data input step in which a shape data input portion provided by the computer inputs shape data that expresses the shape of each material constituting the structure, a material data input step in which a material data input portion provided by the computer inputs material constant data that expresses a material constant of at least one of the materials constituting the structure, a dividing step in which a dividing portion provided by the computer divides the structure into a plurality of small regions, a small region interior calculation step in which a small region interior calculation portion provided by the computer calculates a constituent ratio of the materials included in the small region based on the shape data, and calculates an equivalent material constant for the small region based on the constituent ratio and the material constant data, and a combining step in which a combining portion provided by the computer, obtains an equivalent material constant for a region in which a plurality of the small regions that are adjacent are combined, based on the equivalent material constant for the small region.

Due to the present invention adopting the configuration described above, in a structure constituted by a plurality of materials, it is possible to calculate efficiently a highly accurate equivalent material constant that takes into consideration the directionality of each material.

DETAILED DESCRIPTION OF THE INVENTION

Figure 1A:
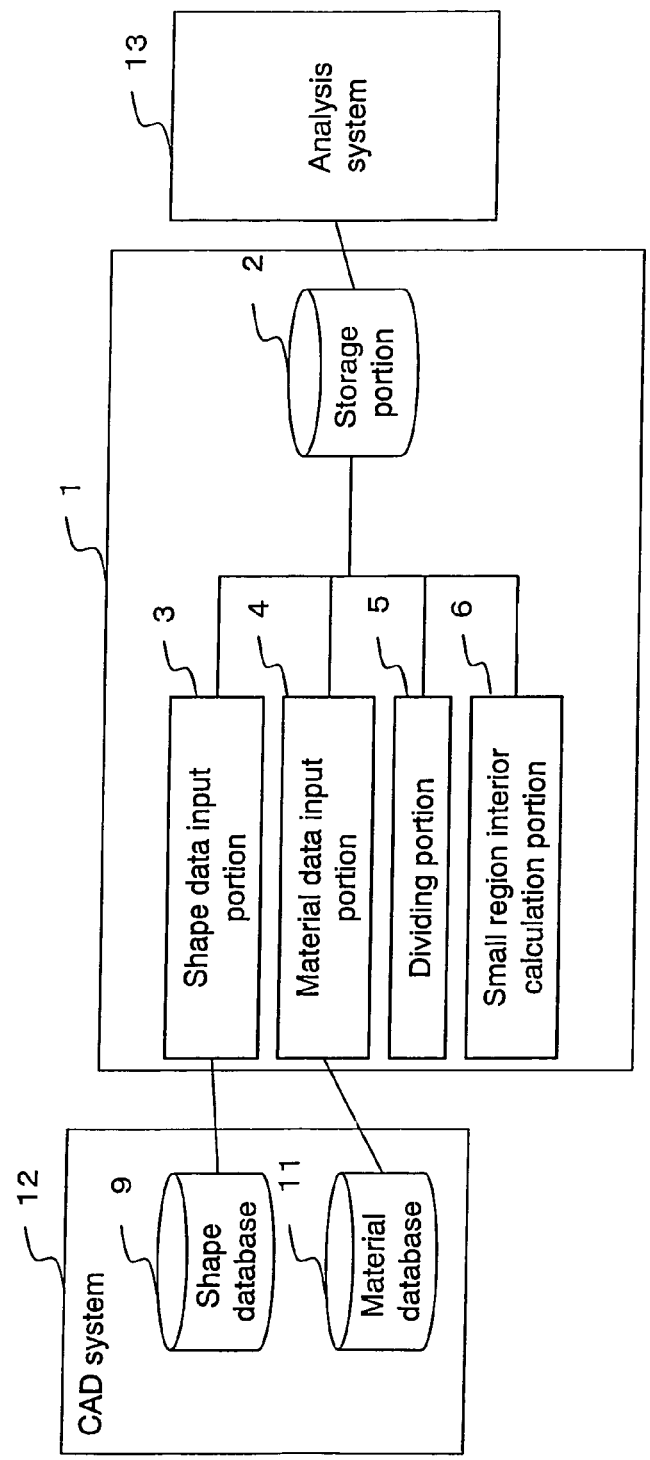
FIG. 1A is a functional block diagram that shows the configuration of an equivalent material constant calculation system.

An equivalent material constant calculation system according to the present invention calculates an equivalent material constant of a structure constituted by a plurality of materials, and includes a shape data input portion that inputs shape data that expresses the shape of each material constituting the structure, a material data input portion that inputs material constant data that expresses a material constant of at least one of the materials constituting the structure, a dividing portion that divides the structure into a plurality of small regions, and a small region interior calculation portion that calculates equivalent material constants in the small regions. The small region interior calculation portion, expresses based on the shape data and material constant data, an equivalent material constant for a region that is part of a small region, with a function that includes a value in a variable that expresses a position in at least one direction in the small regions, and calculates equivalent material constants in the small region with respect to the at least one direction using the function.

The small region interior calculation portion, based on the shape data and material constant data, with a function that includes a value that expresses a location in at least one direction in the small regions in a variable, expresses an equivalent material constant for a region that is part of a small region. Because the small region interior calculation portion calculates equivalent material constants in a small region using the function, it is possible to calculate an equivalent material constant with respect to at least one direction.

In the equivalent material constant calculation system according to the present invention, it is preferable that the small region interior calculation portion includes a boundary function generating portion that sets a coordinate in the direction of one coordinate axis to u in an orthogonal coordinate system that has been set for the structure, and generates, based on the shape data, a boundary function F(u) that expresses a boundary between the materials in a small region, a section setting portion that sets one or two or more sections for u in the small region according to a domain of the boundary function F(u), a section interior calculation portion that creates, in the section, based on the function F(u) and the material constant data, a function that expresses a position where the material constant is applied, and obtains an equivalent material constant of the coordinate axis direction in the section by integrating the function in the section, and an equivalent material constant generating portion that, based on a section equivalent material constant of each section obtained by the section interior calculation portion, obtains an equivalent material constant of the coordinate axis direction in the small region.

Because the small region interior calculation portion obtains an equivalent material constants for the direction of one coordinate in the small region using the boundary function F(u), it is possible to obtain efficiently an equivalent material constant that takes into consideration the directionality of each material in the small region.

In the equivalent material constant calculation system according to the present invention, it is preferable that the small region interior calculation portion includes a minimum region material constant generating portion that further divides the small regions into a plurality of minimum regions along one or two or more directions, and obtains an equivalent material constant for each minimum region based on the shape data and the material constant data, a spectrum calculation portion that obtains a frequency spectrum in each minimum region by performing a Fourier transformation of the distribution of the equivalent material constant of the minimum regions in the small region in one or two or more directions, and an equivalent material constant generating portion that obtains an equivalent material constant for the small region in the one or two or more directions, based on the frequency spectrum in each of the minimum regions.

Because the small region interior calculation portion obtains an equivalent material constant of the small region based on a frequency spectrum for each minimum region obtained by performing a Fourier transformation of the distribution of the equivalent material constant of the minimum regions in the small region from the minimum region material constant generating portion in one or two or more directions, it is possible to obtain efficiently an equivalent material constant that takes into consideration the directionality of each material in the small region.

It is preferable that the equivalent material constant calculation system according to the present invention includes a combining portion that obtains, based on the equivalent material constant for the small region, an equivalent material constant for a region in which a plurality of small regions that are adjacent are combined.

Because the combining portion obtains an equivalent material constant for a region in which a plurality of small regions that are adjacent are combined based on the equivalent material constant for the small region, it is possible to reduce the data quantity of the equivalent material constants obtained as calculation results as necessary.

It is preferable that in the equivalent material constant calculation system according to the present invention, the combining portion obtains the equivalent material constant for a region in which a plurality of the small regions that are adjacent are combined, by deeming the equivalent material constant for each of the plurality of small regions to be a mutually connected resistance, and obtaining a combined resistance.

An equivalent material constant calculation system according to the present invention calculates an equivalent material constant of a structure constituted by a plurality of materials, and includes a shape data input portion that inputs shape data that expresses the shape of each material constituting the structure, a material data input portion that inputs material constant data that expresses a material constant of at least one of the materials constituting the structure, a dividing portion that divides the structure into a plurality of small regions, and a small region interior calculation portion that calculates constituent ratios of the materials included in the small regions based on the shape data, and calculates equivalent material constants in the small regions based on the constituent ratios and the material constant data, and a combining portion that obtains, based on the equivalent material constants for the small region, an equivalent material constant for a region in which a plurality of the small regions that are adjacent are combined.

With the equivalent material constant calculation system according to the present invention, even when the dividing portion has finely divided a structure into a large number of small regions, and the small region interior calculation portion has obtained equivalent material constants for a large number of finely divided small regions, an equivalent material constant is obtained by the combining portion for a region in which a plurality of the small regions that are adjacent are combined. Thus, it is possible to reduce the data quantity of the equivalent material constants obtained as calculation results as necessary.

It is preferable that in the equivalent material constant calculation system according to the present invention, the dividing portion divides the structure into a plurality of layers, and divides the divided layers into small regions, and the combining portion includes a lamination direction combining portion that obtains an equivalent material constant of a region in which the small regions of the layers are combined in the lamination direction, based on an equivalent material constant of the small regions of each layer, and a perpendicular direction combining portion that obtains an equivalent material constant of a region in which the small regions that are adjacent are combined in the direction perpendicular to the lamination direction.

Because the combining portion obtains an equivalent material constant of a region in which the small regions divided into each layer by the dividing portion are combined in the lamination direction, and an equivalent material constant of a region in which adjacent small regions that are adjacent are combined in the direction perpendicular to the lamination direction, an equivalent material constant of the combined region can be obtained efficiently.

It is preferable that in the equivalent material constant calculation system according to the present invention, the combining portion deems the equivalent material constant for each of the combined plurality of small regions to be a mutually connected resistance, and using Kirchoff's law, obtains an equivalent material constant for a region in which a plurality of the small regions that are adjacent are combined.

By using Kirchoff's law, the combining portion can obtain efficiently an equivalent material constant for a region in which a plurality of the small regions that are adjacent are combined.

In the equivalent material constant calculation system according to the present invention, it is possible to adopt a configuration wherein the structure is an electronic circuit board, and the material constant is thermal conductivity or thermal resistance.

In the equivalent material constant calculation system according to the present invention, it is possible to adopt a configuration wherein the structure is an electronic circuit board, the material constant is thermal conductivity or thermal resistance, and the layer is a wire layer or an insulation layer of the electronic circuit board.

A storage medium storing an equivalent material constant calculation program according to the present invention allows a computer to execute processing that calculates an equivalent material constant of a structure constituted by a plurality of materials. The processing includes shape data input processing that inputs shape data that expresses the shape of each material constituting the structure, material data input processing that inputs material constant data that expresses a material constant of at least one of the materials constituting the structure, dividing processing that divides the structure into a plurality of small regions, and small region interior calculation processing that calculates equivalent material constants in the small regions, in which the small region interior calculation processing, based on the shape data and material constant data, expresses an equivalent material constant for a region that is a portion of a small region, with a function that includes a value in a variable that expresses a position in at least one direction in the small regions, and calculates an equivalent material constant for the small region with respect to the at least one direction using the function.

In the equivalent material constant calculation program according to the present invention, it is preferable that the small region interior calculation processing includes boundary function generating processing that sets a coordinate in the direction of one coordinate axis to u in an orthogonal coordinate system that has been set for the structure, and generates, based on the shape data, a boundary function F(u) that expresses a boundary between the materials in a small region, section setting processing that sets one or two or more sections for u in the small region according to a domain of the boundary function F(u), section interior calculation processing that creates, in the section, based on the function F(u) and the material constant data, a function that expresses a position where the material constant is applied, and obtains an equivalent material constant of the coordinate axis direction in the section by integrating the function in the section, and equivalent material constant generating processing that, based on a section equivalent material constant of each section obtained by the section interior calculation portion, obtains an equivalent material constant of the coordinate axis direction in the small region.

In the equivalent material constant calculation program according to the present invention, it is preferable that the small region interior calculation processing includes minimum region material constant generating processing that further divides each of the small regions into a plurality of minimum regions along one or two or more directions, and obtains an equivalent material constant for each minimum region based on the shape data and the material constant data, spectrum calculation processing that obtains a frequency spectrum in each minimum region by performing a Fourier transformation of the distribution of the equivalent material constant of the minimum regions in the small region in one or two or more directions, and equivalent material constant generating processing that obtains an equivalent material constant for the small region in the one or two or more directions, based on the frequency spectrum in each of the minimum regions.

An equivalent material constant calculation program stored on a storage medium according to the present invention allows a computer to execute processing that calculates an equivalent material constant of a structure constituted by a plurality of materials. The processing includes shape data input processing that inputs shape data that expresses the shape of each material constituting the structure, material data input processing that inputs material constant data that expresses a material constant of at least one of the materials constituting the structure, dividing processing that divides the structure into a plurality of small regions, small region interior calculation processing that calculates constituent ratios of the materials included in the small region based on the shape data, and calculates an equivalent material constant for the small region based on the constituent ratio and the material constant data, and combining processing that, obtains, based on the equivalent material constant for the small region, an equivalent material constant for a region in which a plurality of the small regions that are adjacent are combined.

An equivalent material constant calculation method according to the present calculates an equivalent material constant of a structure constituted by a plurality of materials using a computer. The method include a shape data input step in which a shape data input portion provided by the computer inputs shape data that expresses the shape of each material constituting the structure, a material data input step in which a material data input portion provided by the computer inputs material constant data that expresses a material constant of at least one of the materials constituting the structure, a dividing step in which a dividing portion provided by the computer divides the structure into a plurality of small regions, and a small region interior calculation step that calculates equivalent material constants in the small regions, wherein the small region interior calculation step, in which a small region interior calculation portion provided by the computer expresses, based on the shape data and material constant data, an equivalent material constant for a region that is a portion of a small region, with a function that includes a value in a variable that expresses a location in the small region in at least one direction, and calculates an equivalent material constant for the small region with respect to the at least one direction using the function.

In the equivalent material constant calculation method according to the present invention, it is preferable that the small region interior calculation step includes a boundary function generating step of setting a coordinate in the direction of one coordinate axis to u in an orthogonal coordinate system that has been set for the structure, and generating, based on the shape data a boundary function F(u) that expresses a boundary between the materials within the small region, a section setting step of setting one or more sections for u in the small region according to a domain of the boundary function F(u), a section interior calculation step of creating, in the section a function that expresses a position where the material constant is applied, based on the function F(u) and the material constant data, and obtaining an equivalent material constant of the coordinate axis direction in the section by integrating the function in the section, and an equivalent material constant generating step of obtaining an equivalent material constant of the coordinate axis direction in the small region, based on a section equivalent material constant of each section which is obtained in the section interior calculation step.

In the equivalent material constant calculation method according to the present invention, it is preferable that the small region interior calculation step includes a minimum region material constant generating step of further dividing a small regions into a plurality of minimum regions along one or more directions, and obtaining an equivalent material constant for each minimum region, based on the shape data and the material constant data, a spectrum calculation step of obtaining a frequency spectrum in each minimum region by performing a Fourier transformation of the distribution of the equivalent material constant of the minimum regions in the small region in one or more directions, and an equivalent material constant generating step of obtaining an equivalent material constant for the small region in the one or more directions, based on the frequency spectrum in each of the minimum regions.

An equivalent material constant calculation method according to the present invention calculates an equivalent material constant of a structure constituted by a plurality of materials using a computer. The method includes a shape data input step in which a shape data input portion provided by the computer inputs shape data that expresses the shape of each material constituting the structure, a material data input step in which a material data input portion provided by the computer inputs material constant data that expresses a material constant of at least one of the materials constituting the structure, a dividing step in which a dividing portion provided by the computer divides the structure into a plurality of small regions, a small region interior calculation step in which a small region interior calculation portion provided by the computer calculates a constituent ratio of the materials included in the small region based on the shape data, and calculates an equivalent material constant for the small region based on the constituent ratio and the material constant data, and a combining step in which a combining portion provided by the computer obtains an equivalent material constant for a region in which a plurality of the small regions that are adjacent are combined, based on the equivalent material constant for the small region.

An equivalent material constant calculation system according to the present invention that calculates an equivalent material constant of a structure constituted by a plurality of materials includes a shape data input portion that inputs shape data that expresses the shape of each material constituting the structure, a material data input portion that inputs material constant data that expresses a material constant of at least one of the materials constituting the structure, a dividing portion that divides the structure into a plurality of small regions, and a small region interior calculation portion that calculates equivalent material constants in the small regions, wherein the small region interior calculation portion calculates an area of each material included in the small region based on the shape data, obtains a slope of a line that expresses a boundary between the materials relative to a predetermined direction, and calculates an equivalent material constant for the small region based on the slope, the area, and the material constant data.

Because the small region interior calculation portion calculates the equivalent material constant based on the slope, the area, and the material constant data, an equivalent material constant is calculated that takes into consideration the directionality of the shape of each material occupying part of the interior of the small region. Also, the small region interior calculating portion calculates the equivalent material constant by obtaining the area and the slope. Thus, the small region interior calculating portion can calculate an equivalent material constant that takes into consideration the directionality with simpler processing than, for example, a method that divides the small regions more finely and analyzes that data.

An equivalent material constant calculation system according to the present invention calculates an equivalent material constant of a structure constituted by a plurality of materials, and includes a shape data input portion that inputs shape data that expresses the shape of each material constituting the structure, a material data input portion that inputs material constant data that expresses a material constant of at least one of the materials constituting the structure, a dividing portion that divides the structure into a plurality of small regions, a representative material determining portion that determines a material that represents respective small regions for each of the plurality of small regions, a material constant selection portion that selects the material constant of the material that represents the respective small regions from the material constant data, and a combining portion that calculates an equivalent material constant for a region in which a plurality of the small regions that are adjacent are combined with respect to at least one direction, by combining the material constant of the representative material of the plurality of adjacent small regions in at least one direction.

With the equivalent material constant calculation system according to the present invention, the representative material determining portion determines a representative material for each small region divided by the dividing portion, and the material constant of that representative material is selected by the material constant selection portion. Because it is not necessary to calculate the material constants of the small regions, no time is required to determine the material constants of the small regions. The combining portion, by combining the material constants given one at a time to each small region with respect to at least one direction, can obtain an equivalent material constant that takes into consideration directionality with a simple calculation. As a result, it is possible to calculate efficiently an equivalent material constant that takes into consideration anisotropy of the structure.

Also, even when the dividing portion has finely divided the structure into a large number of small regions, an equivalent material constant is obtained by the combining portion for a region in which a plurality of adjacent small regions are combined. Thus, it is possible to decrease the data quantity of equivalent material constants obtained as calculation results as necessary.

It is preferable that in the equivalent material constant calculation system according to the present invention, the dividing portion divides part of the structure into a plurality of small regions, and the representative material determining portion, the material constant selection portion, and the combining portion perform processing for the regions of part of the structure divided by the dividing portion.

In this way, because the processing that calculates an equivalent material constant for a region that is a part of the structure divided by the dividing portion is performed, it is possible to omit processing that calculates an equivalent material constant of locations unnecessary for analysis. Thus, it is possible to achieve a shortening of calculation time.

It is preferable that in the equivalent material constant calculation system according to the present invention, the combining portion calculates an equivalent material constant for each medium region in which a plurality of adjacent small regions are combined, and the medium region is a region that is part of the structure, and a plurality of the medium regions are included in the structure.

By doing so, an equivalent material constant is calculated for each medium region that constitutes a part of the structure. Thus, it is possible to express compression of the material that constitutes the structure with the size of the equivalent material constant. That is, because an equivalent material constant is obtained for a plurality of medium regions included in the structure, a distribution of the equivalent material constants in the structure is obtained.

It is preferable that in the equivalent material constant calculation system according to the present invention, the dividing portion divides the structure into small regions by dividing the structure into a plurality of layers parallel to each other, and further dividing each layer.

By doing so, for example, it is possible to divide a structure that has a layer structure into a plurality of layers that are parallel to each other according to the layer structure, and to further divide each layer. Due to the dividing portion dividing according to the layer structure of the structure, the combining portion combines the divided small regions and it is possible to obtain efficiently an equivalent material constant.

It is preferable that in the equivalent material constant calculation system according to the present invention, the combining portion obtains the equivalent material constant by deeming the material constant of the material that represents the respective small regions in the plurality of adjacent small regions to be a mutually connected resistance, and obtaining a combined resistance. For example, by deeming the material constant to be resistance when the material constant has characteristics similar to electrical resistance such as thermal resistance, it is possible to obtain a combined resistance using a circuit equation. Thus, it is possible to obtain efficiently an equivalent material constant for a region in which a plurality of adjacent small regions are combined.

In the equivalent material constant calculation system according to the present invention, it is possible to adopt a configuration wherein the structure is an electronic circuit board, and the material constant is a thermal conductivity or thermal resistance.

In the equivalent material constant calculation system according to the present invention, it is possible to adopt a configuration wherein the structure is an electronic circuit board, and the material constant is a thermal conductivity or thermal resistance, and the layer is a wire layer or an insulation layer of the electronic circuit board. By doing so, it is possible to calculate efficiently the equivalent thermal conductivity or the equivalent heat resistance of an electronic circuit board that has a layer structure.

It is preferable that in the equivalent material constant calculation system according to the present invention, the structure is an electronic circuit board, and the dividing portion divides the structure into small regions whose maximum width is not greater than the minimum width of wire formed on the electronic circuit board. By doing so, it is possible to calculate precisely the equivalent thermal conductivity of an electronic circuit board that has a layer structure.

A design system according to the present invention includes the equivalent material constant calculation system according to the present invention, and includes a storage portion that stores design data of the structure including the shape data and the material constant data, an analysis portion that analyzes and outputs the flow of heat, stress distribution electromagnetic fields, or hydrokinetics of the structure, by simulation based on the equivalent material constant of the structure calculated by the equivalent material constant calculation system and the design data, and a design modification portion that modifies the design data of the storage portion based on a command to modify the design data from a designer.

In the design system according to the present invention, the design portion performs analysis using the equivalent material constants of the structure calculated by the equivalent material constant calculation system according to the present invention. The analysis portion can perform analysis using equivalent material constants that take into consideration directionality. Thus, in the analysis portion, analysis by simulation that is closer to the actual phenomenon becomes possible.

Also, because an equivalent material constant of a region in which small regions are combined is obtained by the equivalent material constant calculation system, it is possible to put the characteristics of the structure into the equivalent material constants without modeling the minimum regions of the structure. Thus, the number of elements (mesh number) when performing analysis with the analysis portion decreases, and it is possible to shorten the analysis time greatly.

Because the amount of data of the equivalent material constants calculated by the equivalent material constant calculation system is low, the amount of calculation in the analysis portion is also low. As a result, efficient analysis is possible.

Also, the user can view the analysis results output by the analysis portion and submit a design data modification command to the design modification portion. Thus, the analysis results are reflected in the design data, and high quality design data is obtained.

An equivalent material constant calculation method according to the present invention calculates an equivalent material constant of a structure constituted by a plurality of materials using a computer. The method includes a shape data input step in which a shape data input portion provided by the computer inputs shape data that expresses the shape of each material constituting the structure, a material data input step in which a material data input portion provided by the computer inputs material constant data that expresses a material constant of at least one of the materials constituting the structure, a dividing step in which a dividing portion provided by the computer divides the structure into a plurality of small regions, and a small region interior calculation step in which a small region interior calculation portion provided by the computer calculates equivalent material constants in the small regions. In the small region interior calculation step, the small region interior calculation portion calculates an area of each material included in the small region based on the shape data, obtains a slope of a line that expresses a boundary between the materials relative to a predetermined direction, and calculates an equivalent material constant for the small region based on the slope, the area, and the material constant data.

An equivalent material constant calculation method according to the present invention calculates an equivalent material constant of a structure constituted by a plurality of materials using a computer. The method includes a shape data input step in which a shape data input portion provided by the computer inputs shape data that expresses the shape of each material constituting the structure, a material data input step in which a material data input portion provided by the computer inputs material constant data that expresses a material constant of at least one of the materials constituting the structure, a dividing step in which a dividing portion provided by the computer divides the structure into a plurality of small regions, a representative material determining step in which a representative material determining portion provided by the computer determines a material that represents respective small regions for each of the plurality of small regions, a material constant selection step in which a material constant selection portion provided by the computer selects the material constant of the material that represents the respective small regions from the material constant data, and a combining step in which a combining portion provided by the computer calculates an equivalent material constant for a region in which a plurality of the small regions that are adjacent are combined with respect to at least one direction, by combining the material constant of the representative material of the plurality of adjacent small regions in at least one direction.

A structure manufacturing method according to the present invention, using a computer that can access a storage device in which a plurality of design data of a structure constituted by a plurality of materials is stored, manufactures the structure, and includes a calculating step in which the computer calculates an equivalent material constant of the structure by the equivalent material constant calculation method according to the present invention, an analysis step in which an analysis portion provided by the computer analyzes the flow of heat, stress distribution, electromagnetic field, or hydrokinetics of the structure, by simulation based on the equivalent material constant and the design data, a design data selection step in which a design data selection portion provided by the computer selects design data from among the plurality of design data based on the analysis results obtained by the analysis step for a structure expressed by the plurality of design data stored in the storage device, and a manufacturing step in which a CAM, connected such that data communications are possible with the computer, manufactures a structure based on the design data selected by the design data selection step.

In the combining step of the manufacturing method according to the present invention, by combining a material constant of the selected representative material with respect to at least one direction, an equivalent material constant of the structure can be calculated efficiently for each small region divided by the dividing step that takes into consideration directionality. In the analysis step, because the analysis portion performs analysis using an equivalent material constant that takes into consideration directionality, analysis by simulation that is close to the actual phenomenon becomes possible. Optimum design data is selected based on these analysis results. CAM manufactures the structure based on the optimum design data. As a result, a structure having the optimum structure is effectively manufactured.

A storage medium storing an equivalent material constant calculation program according to the present invention allows a computer to execute processing that calculates an equivalent material constant of a structure constituted by a plurality of materials. The processing includes a shape data input processing that inputs shape data that expresses the shape of each material constituting the structure, a material data input processing that inputs material constant data that expresses a material constant of at least one of the materials constituting the structure, a dividing processing that divides the structure into a plurality of small regions, and a small region interior calculation processing that calculates equivalent material constants in the small regions, wherein the small region interior calculation processing calculates an area of each material included in the small region based on the shape data, obtains a slope of a line that expresses a boundary between the materials relative to a predetermined direction, and calculates an equivalent material constant for the small region based on the slope, the area, and the material constant data.

A storage medium storing an equivalent material constant calculation program according to the present invention allows a computer to execute processing that calculates an equivalent material constant of a structure constituted by a plurality of materials. The processing includes shape data input processing that inputs shape data that expresses the shape of each material constituting the structure, material data input processing that inputs material constant data that expresses a material constant of at least one of the materials constituting the structure, dividing processing that divides the structure expressed by the shape data into a plurality of small regions, representative material determining processing that determines a material that represents respective small regions for each of the plurality of small regions, material constant selection processing that selects the material constant of the material that represents the respective small regions from the material constant data, and combining processing that calculates an equivalent material constant for a region in which a plurality of the small regions that are adjacent are combined with respect to at least one direction, by combining the material constant of the representative material of the plurality of adjacent small regions. Thus, with the equivalent material constant calculation program according to the present invention, it is possible to calculate an equivalent material constant that has taken into consideration anisotropy of the structure.

Hereinafter, the present invention will be described by way of illustrative embodiments with reference to the drawings.

Embodiment 1

Embodiment 1 is an equivalent material constant calculation system in which an equivalent material constant of a structure constituted by a plurality of materials is calculated using an integral formula.

FIG. 1A is a functional block diagram that shows the configuration of an equivalent material constant calculation system of the present embodiment. As shown in FIG. 1A, the equivalent material constant calculation system 1 of the present embodiment includes a storage portion 2, a shape data input portion 3, a material data input portion 4, a dividing portion 5, and a small region interior calculation portion 6 the equivalent material constant calculation system 1 is connected to a CAD system 12 and an analysis system 13.

The equivalent material constant calculation system 1 can be constructed on, for example, general purpose equipment such as a personal computer or a workstation (hereinafter, referred to as 'PC or the like'). The function of the shape data input portion 3, the material data input portion 4, the dividing portion 5, and the small region interior calculation portion 6 can be realized by the CPU of a PC or the like that executes a predetermined program. As the storage portion 2, other than a storage medium built into a PC or the like such as a hard disk or RAM, a portable storage medium such as a floppy (registered trademark) disk or memory card, a storage medium in a storage device on a network, or the like can be used.

The equivalent material constant calculation system 1 can be constructed by, for example, installing the program that allows a computer to execute the processing that is performed by the shape data input portion 3, the material data input portion 4, the dividing portion 5, and the small region interior calculation portion 6 from a storage medium such as a CD-ROM, or by download via a communications line, to a desired PC or the like.

Figure 1B:
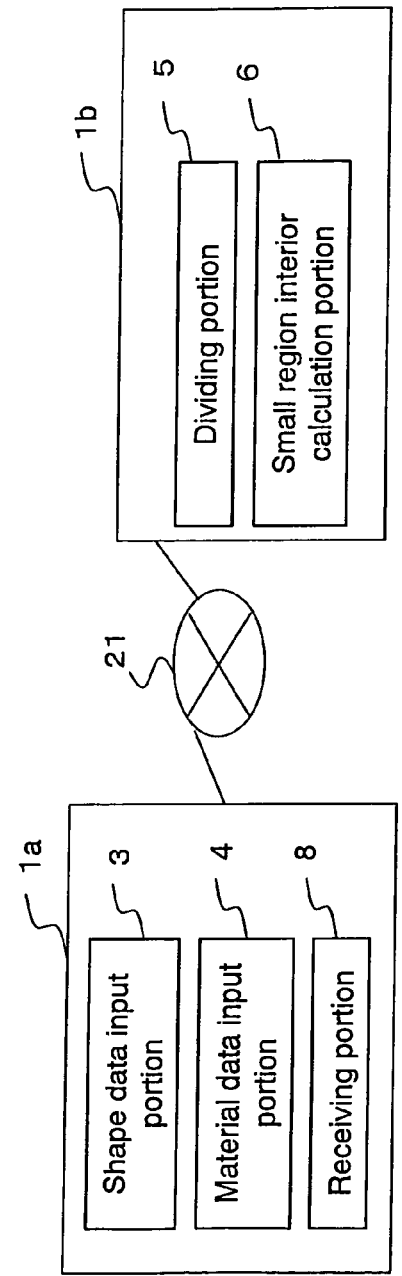
FIG. 1B is a functional block diagram that shows an example of the configuration of an equivalent material constant calculation system in which the function of the equivalent material constant calculation system 1 is distributed to a terminal system 1a and server system 1b.

The hardware configuration is not limited to the configuration shown in FIG. 1A. For example, the function of the equivalent material constant calculation system 1 may be distributed to a plurality of PCs or the like that have been connected by an internet or a LAN such that communication is possible, for example. FIG. 1B is a functional block diagram that shows an example of the configuration of an equivalent material constant calculation system in which the function of the equivalent material constant calculation system 1 is distributed to a terminal system 1a and server system 1b.

As shown in FIG. 1B, the terminal system 1a includes, a shape data input portion 3, a material data input portion 4, and a receiving portion 8. The server system 1b includes a dividing portion 5, and a small region interior calculation portion 6. The terminal system 1a and the server system 1b are connected by an network 21 which is internet or intranet or the like for example. The terminal system 1a can be constructed on, for example, personal computer or the like which is connected to the network 21. The server system 1b can be constructed on, for example, server computer or the like which is connected to the network 21.

The shape date input by the shape data input portion 3 and the material data input by the material data input portion 4 is send to the server system 1b with requirement of calculation for a equivalent material constant. The dividing portion 5, and the small region interior calculation portion 6 included in the server system 1b calculate a equivalent material constant base on the date send from the terminal system 1a. the calculated equivalent material constant is send to the terminal system 1a. the receiving portion 8 receives the equivalent material constant which is send from the server system 1b. According to the configuration shown in FIG. 1B, the terminal system 1a can obtain the equivalent material constant without processing of calculating. The terminal system 1a may include the system of at least one of the CAD system 12 and the analysis system 13.

The shape data input portion 3 inputs shape data of the structure for which an equivalent material constant will be calculated, and saves that data in the storage portion 2. The shape data, for example, is shape data that expresses the shape of each material constituting the structure. An electronic circuit board can be given as an example of the structure. Ordinarily, shape data of an electronic circuit board often is created with a CAD system 12 for electronic circuit board design and saved in the CAD system 12, so in this case information that is stored in a shape database 9 of the CAD system 12 can be used. Also, the shape data input portion 3 may, for example, read a file in which the shape data is stored to input new data, or the shape data input portion 3 may receive input of shape data that a designer created via an input device such as a keyboard or a mouse provided in a PC or the like.

The material data input portion 4 inputs material constant data that expresses the material constants of the materials that constitute the structure. An example of data that expresses a material constant, if the structure is an electronic circuit board, is the material constant (for example, such as a thermal conductivity or thermal resistance) of a material that constitutes the electronic circuit board. Material constant data of an electronic circuit board also can be used if that information is saved in a material database 11 in the CAD system 12 for electronic circuit board design. Also, the possibility of input via a file, keyboard, mouse, or the like is the same as for the shape data input portion.

The dividing portion 5 divides the structure expressed by the shape data stored in the storage portion 2 into a plurality of small regions. The small region interior calculation portion 6 calculates an equivalent material constant for each of the divided small regions.

Figure 2:
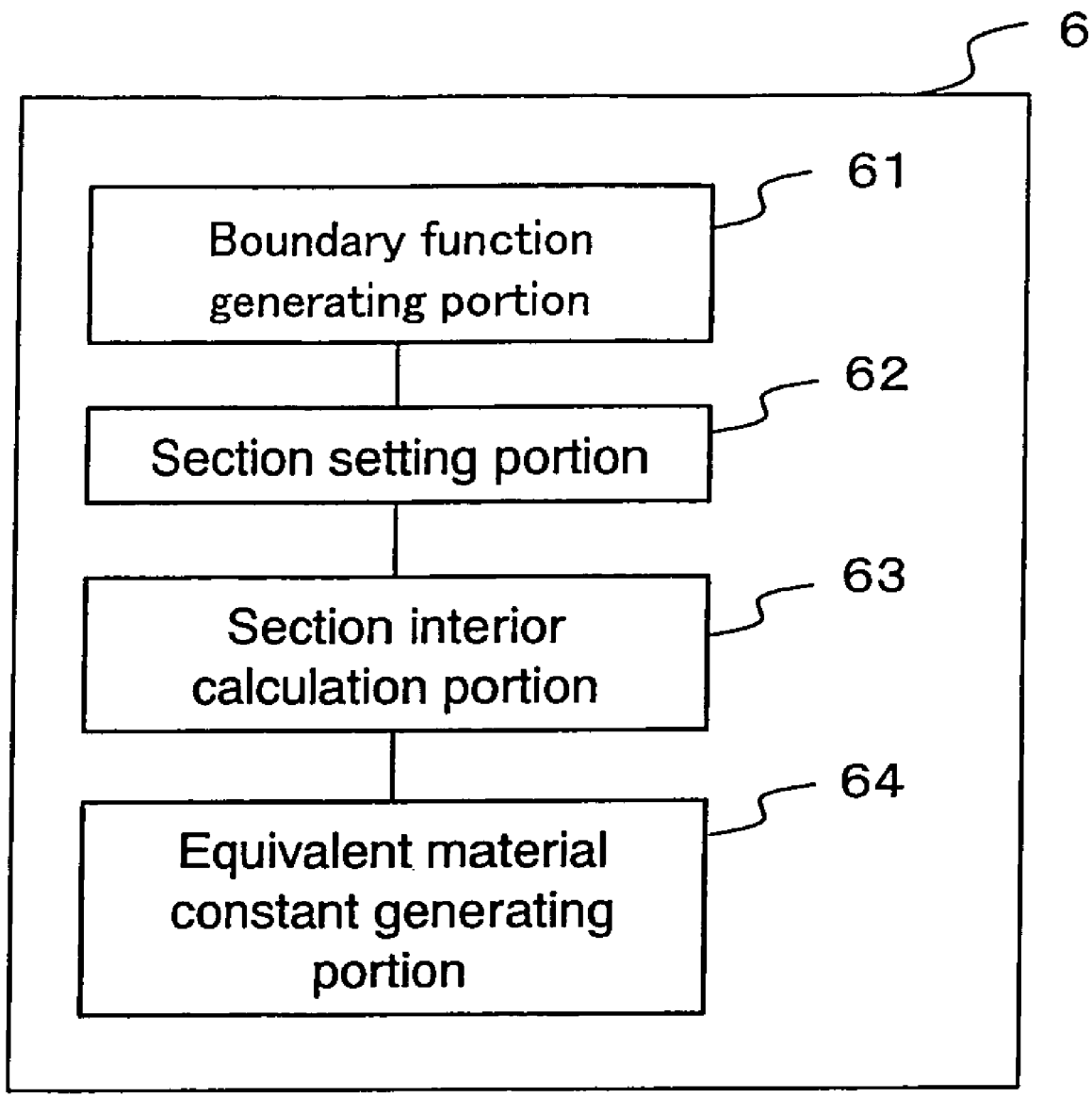
FIG. 2 is a functional block diagram that shows the configuration of a small region interior calculation portion 6.

FIG. 2 is a functional block diagram that shows the configuration of the small region interior calculation portion 6. As shown in FIG. 2, the small region interior calculation portion 6 includes a boundary function generating portion 61, a section setting portion 62, a section interior calculation portion 63, and an equivalent material constant generating portion 64. These functions are described below.

Figure 3:
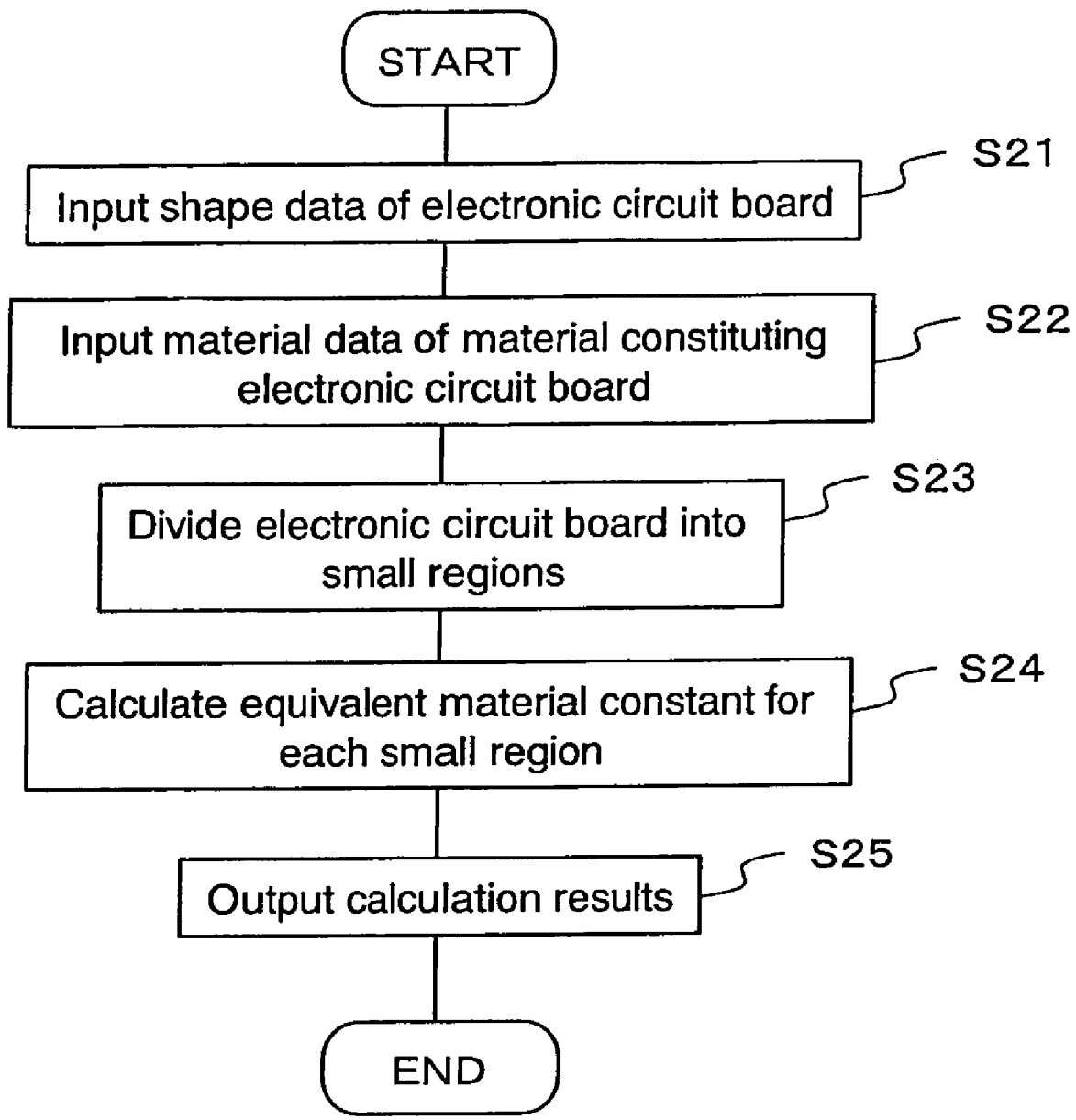
FIG. 3 is a flowchart that shows the operation of an equivalent material constant calculation system 1.

Following is a description of the operation of the equivalent material constant calculation system 1 of the present embodiment with reference to FIGS. 1 to 4. FIG. 3 is a flowchart that shows the operation of the equivalent material constant calculation system 1. In the present embodiment, as one example, the processing that calculates the equivalent thermal conductivity of an electronic circuit board is described. However, the present invention is not limited to an equivalent thermal conductivity calculation method of an electronic circuit board or other structure. The present invention includes calculation methods for an equivalent electrical conductivity, equivalent dielectric constant, equivalent magnetic permeability, equivalent Young's modulus, or other material constants of composite materials.

Figure 4:
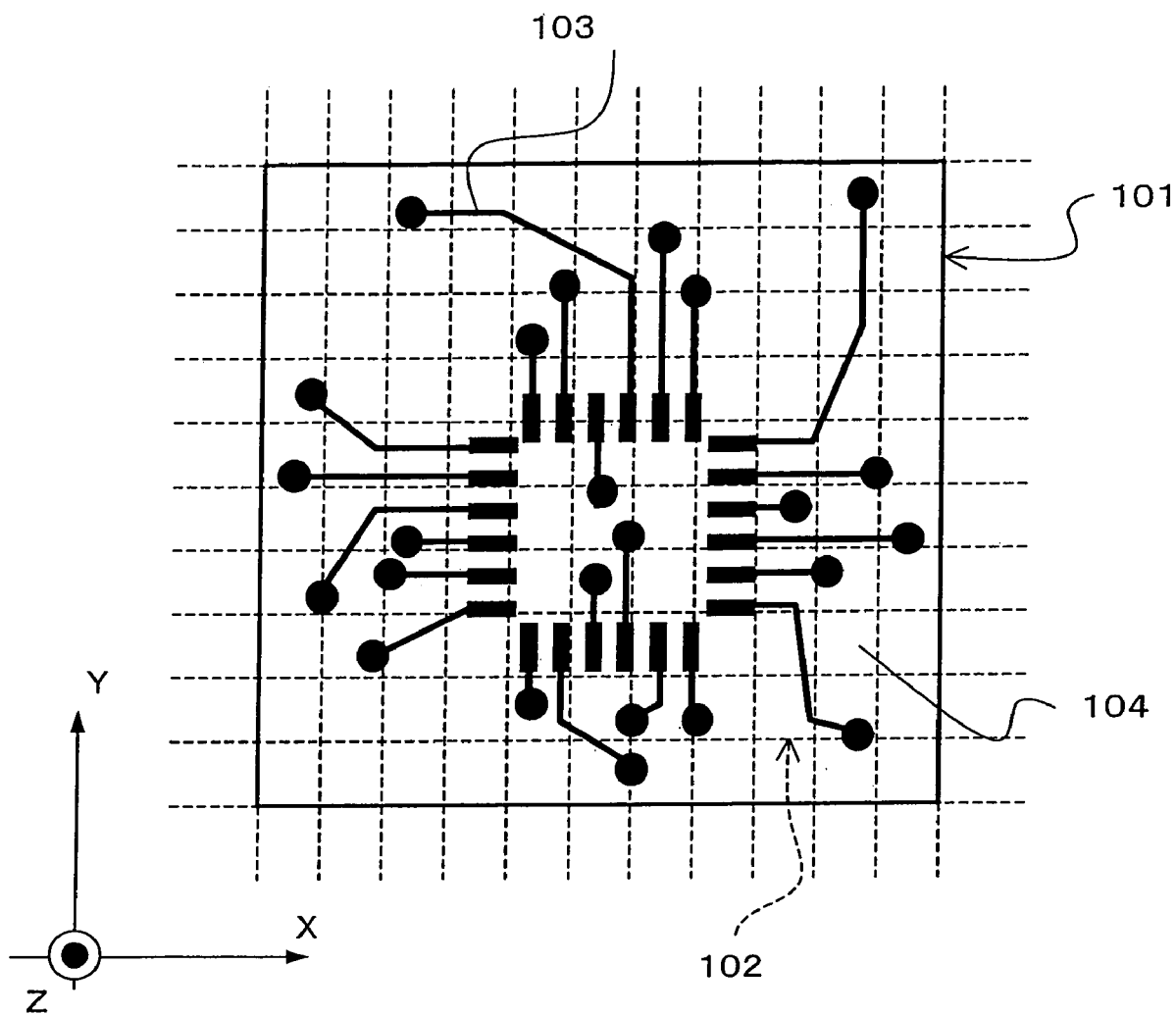
FIG. 4 shows an example of the shape of a wire layer included in an electronic circuit board for which an equivalent thermal conductivity calculation is performed.

First, the shape data input portion 3 inputs shape data of the electric circuit board for which the equivalent thermal conductivity calculation will be performed (Step S21). The shape data of the electric circuit board is created with a CAD system, for example. The electric circuit board ordinarily is configured by alternately layering a wire layer and an insulation layer. FIG. 4 shows an example of the shape of a wire layer included in the electronic circuit board for which the equivalent thermal conductivity calculation will be performed, and is a plan view in a plane parallel to a layer of the electronic circuit board, i.e. in the XY plane.

The wire layer of an electronic circuit board 101 is configured from a wire pattern portion 103 and a non-wire portion 104. Ordinarily the wire pattern portion 103 is constituted by material with a comparatively high thermal conductivity such as metal, and the non-wire portion 104 often is constituted by material with a comparatively low thermal conductivity such as glass, resin, ceramics, or composites of these materials.

The material data input portion 4 inputs material constant data of the materials that constitute the electronic circuit board 101 (Step S22). As material constant data, for example, the thermal conductivity ($\lambda$trace) of the wire material, which is metal material that constitutes the wire pattern portion 103 of the electronic circuit board 101, and the thermal conductivity ($\lambda$insulator) of the insulator material, which is resin material that constitutes the non-wire portion 104, are input. Also, for example, because $\lambda$insulator is extremely small in comparison to $\lambda$trace, in the subsequent equivalent thermal conductivity calculation processing, when it is possible to ignore $\lambda$insulator in the calculation, it is also possible to omit the input of $\lambda$insulator.

Because the shapes of the wire pattern portion 103 and the non-wire portion 104 that constitute the electronic circuit board 101 are extremely complicated, in order to simplify the subsequent processing, the dividing portion 5 divides the electronic circuit board 101 into layers of each wire layer and insulation layer in the direction of the Z axis, and divides each divided layer into small regions 102 in the direction of the XY plane (Step S23). Division in the direction of the Z axis can performed for each of the wire and insulation layers that constitute the electronic circuit board 101. With respect to division in the direction of the XY plane, for example, as shown in FIG. 4, a layer can be divided into 11 equal divisions in the direction of the X axis and 10 equal divisions in the direction of the Y axis, dividing the whole into 110 small regions. It is not necessary for the division into small regions to divide each direction in equal parts. It is also possible to divide into small regions with different sizes as necessary.

It does not matter if this division into the small regions 102 is the same for each of the wire and insulation layers, or if it is different. Also, this division may be the same as the element division in a computer simulation such as a finite element method performed using an equivalent thermal conductivity obtained by this method, for example, or it may be a dividing method that is different from this element division.

Next, the small region interior calculation portion 6 calculates the equivalent thermal conductivity for each of these small regions 102 (Step S24).

Figure 5:
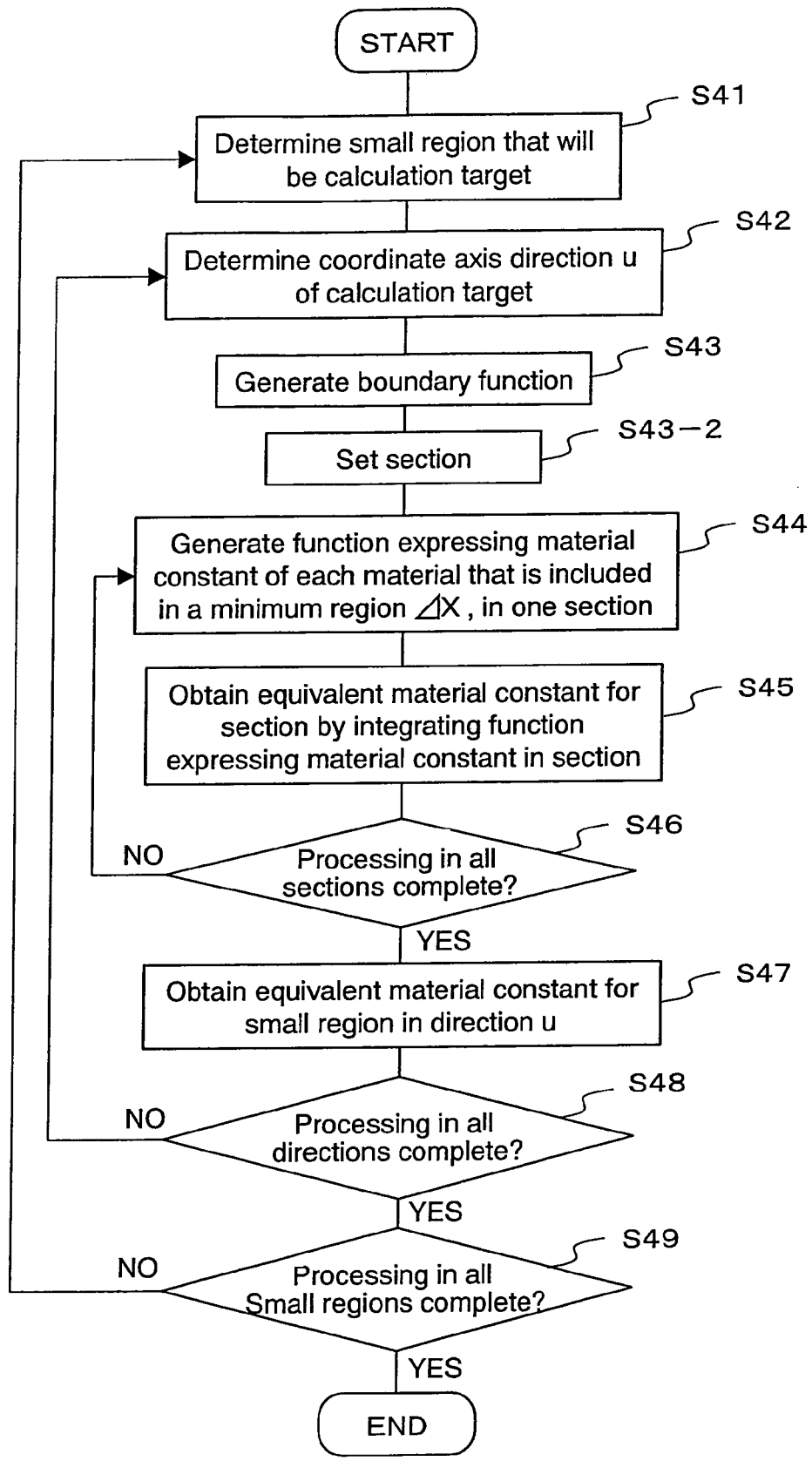
FIG. 5 is a flowchart that shows the detailed flow of processing that calculates an equivalent thermal conductivity for each small region 102.

Here, in Step S24, the details of the processing that calculates an equivalent thermal conductivity for each small region 102 is described with reference to FIGS. 2, 5, and 6. FIG. 5 is a flowchart that shows the detailed flow of processing that calculates an equivalent thermal conductivity for each small region 102 (Step S24).

First, the small region interior calculation portion 6 selects and determines the small region for which an equivalent thermal conductivity will be calculated, from among the divided small regions 102 (Step S41). FIG. 6 shows an example of a selected small region 102. Next, the small region interior calculation portion 6 determines a direction u of the thermal conductivity to be calculated for the selected small region (Step S42). First, the direction u is made equal to the direction of the X axis. That is, an equivalent thermal conductivity of the X axis direction will be calculated. It is preferable that the directions of the coordinate axes (X axis, Y axis, and Z axis) that will be the reference when calculating the equivalent thermal conductivity of the small region are set not only within the small region, but that common coordinate axes are set for the entire electric circuit board.

Figure 6:
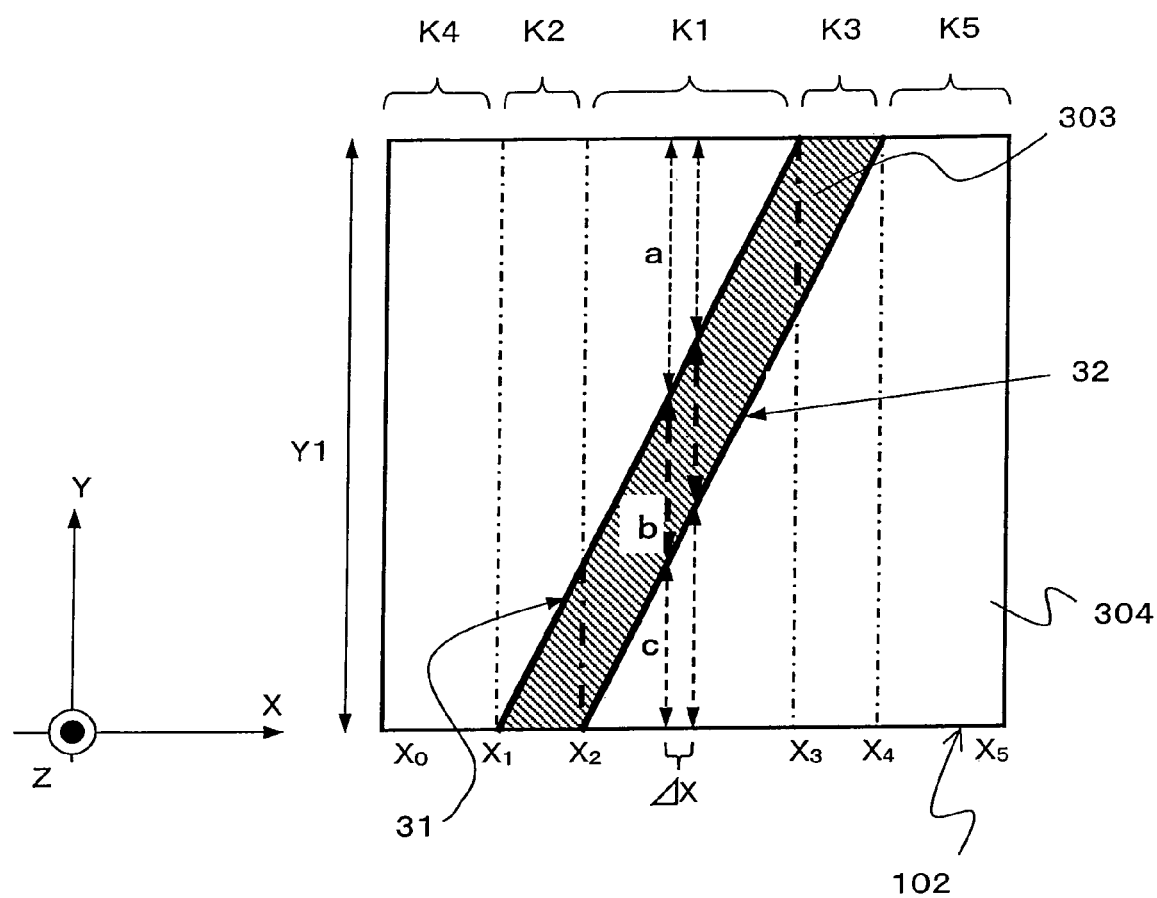
FIG. 6 shows an example of a selected small region 102.

The small region 102 shown in FIG. 6 is configured from one wire pattern portion 303 in the diagonal direction from the lower left to the upper right of the small region 102, and another, non-wire portion 304.

In the boundary function generating portion 61, a function that expresses an upper edge 31 (upper coordinate in the Y axis direction) of the wire pattern portion 303 with an X-Y coordinate system is made Y=F1(X), and a function that expresses a lower edge 32 (lower coordinate in the Y axis direction) of the wire pattern portion 303 with an X-Y coordinate system is made Y=F2(X). However, because only the middle of the small region is handled, the domain of the function F1(X) is the range where X is $X_1$ to $X_3$, and the domain of the function F2(X) is the range where X is $X_2$ to $X_4$. F1(X) and F2(X) are functions that express the boundaries of the wire pattern portion 303 and the non-wire portion 304. These functions are made based on the shape data that the shape data input portion input.

The section setting portion 62, according to the domains of F1(X) and F2(X), sets a section in the small region 102 for X (S43-2). For example, it is possible to set the section $X_2$-$X_3$ where the domain of F1(X) and the domain of F2(X) overlap to be section K1, set the section $X_1$-$X_2$ where only F1(X) is defined to be section K2, set the section $X_3$-$X_4$ where only F2(X) is defined to be section K3, set the section $X_0$-$X_1$ where both F1(X) and F2(X) are not defined to section K4, and set the section $X_4$-$X_5$ to section K5.

Next, the section interior calculation portion 63 generates a function that expresses a material heat resistance Rd (S44) based on functions F1(X), F2(X), and the material constant data of each material (λtrace and λinsulator).

For example, in section K1, when ΔX is made the minimum range of $X_2$ to $X_3$, a heat resistance Rc in the X axis direction of a minimum region expressed by a width in the X axis direction of ΔX and a length in the Y axis direction of c is approximated by ΔX/(λinsulator·c·t). A heat resistance Rb in the X axis direction of a minimum region expressed by a width in the X axis direction of ΔX and a length in the Y axis direction of b is approximated by ΔX/(λtrace·b·t), and a heat resistance Ra in the X axis direction of a minimum region expressed by a width in the X axis direction of ΔX and a length in the Y axis direction of a is approximated by ΔX/(λinsulator·a·t). Here t expresses the thickness of the wire pattern portion 303 in a direction perpendicular to the XY plane.

Here, when the X coordinate of the left end of ΔX is made Xd, and the length in the Y axis direction of the small region 102 is made Y1, a=Y1−F1(Xd), b=F1(Xd)−F2(Xd), and c=F2(Xd), so when using this a, b, and c, the above Ra, Rb, and Rc are indicated by formula 5, formula 6, and formula 7, respectively.

$$Ra = \frac{\Delta X}{\lambda \text{insulator}(Y1 - F1(Xd))t} \quad \text{Formula 5}$$

$$Rb = \frac{\Delta X}{\lambda \text{trace}(F1(Xd) - F2(Xd))t} \quad \text{Formula 6}$$

$$Rc = \frac{\Delta X}{\lambda \text{insulator } F2(Xd)t} \quad \text{Formula 7}$$

where the thermal conductivity of the material that constitutes the wire pattern portion 303 is λtrace, and the thermal conductivity of the material that constitutes the non-wire portion 304 is λinsulator.

In the range where the X axis direction is ΔX and the Y axis direction is the entire small region 102, when considering the thermal resistance in the X axis direction, it is possible to consider the three thermal resistances, whose respective thermal resistance values are Ra, Rb, and Rc, to be connected in parallel, and so the thermal resistance Rd of the whole is shown by formula 8.

$$\frac{1}{Rd} = \frac{1}{Ra} + \frac{1}{Rb} + \frac{1}{Rc} \quad \text{Formula 8}$$
$$= \frac{\lambda \text{insulator}(Y1 - F1(Xd))t}{\Delta X} +$$
$$\frac{\lambda \text{trace}(F1(Xd) - F2(Xd))t}{\Delta X} +$$
$$\frac{\lambda \text{insulator } F2(Xd)t}{\Delta X}$$
$$= \frac{G}{\Delta X}$$
$$G = \lambda \text{insulator}(Y1 - F1(Xd))t +$$
$$\lambda \text{trace}(F1(Xd) - F2(Xd))t + \lambda \text{insulator } F2(Xd)t$$

Formula 8 above is a function that expresses the thermal resistance Rd in the minimum region ΔX. Here, the function shown by the formula 8 is an example of a function that expresses a position where the material constant is applied. Next, the section interior calculation portion 63, by integrating this function within the section K1, obtains an equivalent thermal resistance in the X axis direction for the section K1 (S45).

The equivalent thermal resistance in the X axis direction of the section K1($X_2$-$X_3$) in which both F1(X) and F2(X) are defined can be obtained by reducing the width of ΔX to a limit and integrating Rd in the X axis direction from $X_2$ to $X_3$, and that value Rx1 is shown by formula 9.

$$Rx1 = \int_{X2}^{X3} Rd \quad \text{Formula 9}$$
$$= \int_{X2}^{X3} \frac{1}{G} dx$$
$$G = \lambda \text{insulator}(Y1 - F1(Xd))t +$$
$$\lambda \text{trace}(F1(Xd) - F2(Xd))t + \lambda \text{insulator } F2(Xd)t$$

In the above manner, it is possible to obtain the equivalent thermal resistance in the X axis direction of the section K1 by using the functions F1(X) and F2(X) that express the boundary to form a function (above formula 8) that expresses the thermal resistance of the minimum region ΔX, and integrating this function in the section K1. Accordingly, provided that it is possible to solve functions F1(X) and F2(X), even if the shape of the material is complicated, it is possible to obtain an equivalent thermal resistance with good effectiveness without increasing the processing time and the amount of processing logic.

That is, for each material, by integrating a function (the above formula 8) that includes the product of the size in a particular direction (Y axis direction) of that material and the material constant of that material, with a direction (X axis direction) that differs from the above dimensional direction (Y axis direction), it is possible to obtain an equivalent thermal resistance in the X axis direction.

However, in the present invention, integration does not have only the rigorous mathematical meaning of that word; it includes various kinds of numerical integration performed with a computer using, for example, a trapezoidal approximation method, Simpson method, Gauss-Legendre method, or various other types of approximation methods.

Also, in the present embodiment, calculation was performed taking into consideration the thermal conductivity of both the wire pattern portion 303 and the non-wire portion 304, but when the thermal conductivity λinsulator of the material that constitutes the non-wire portion 304 is very small in comparison to the thermal conductivity λtrace of the material that constitutes the wire pattern portion 303, it is possible to lighten the calculation load by ignoring the thermal conductivity effect of the insulator material that constitutes the non-wire portion.

Also, in the present embodiment, calculation was performed with boundary functions F1(X) and F2(X) as functions that express boundary lines of the XY plane, but calculation also may be performed by generating boundary functions as functions that express boundary planes of the space XYZ.

Figure 7A:
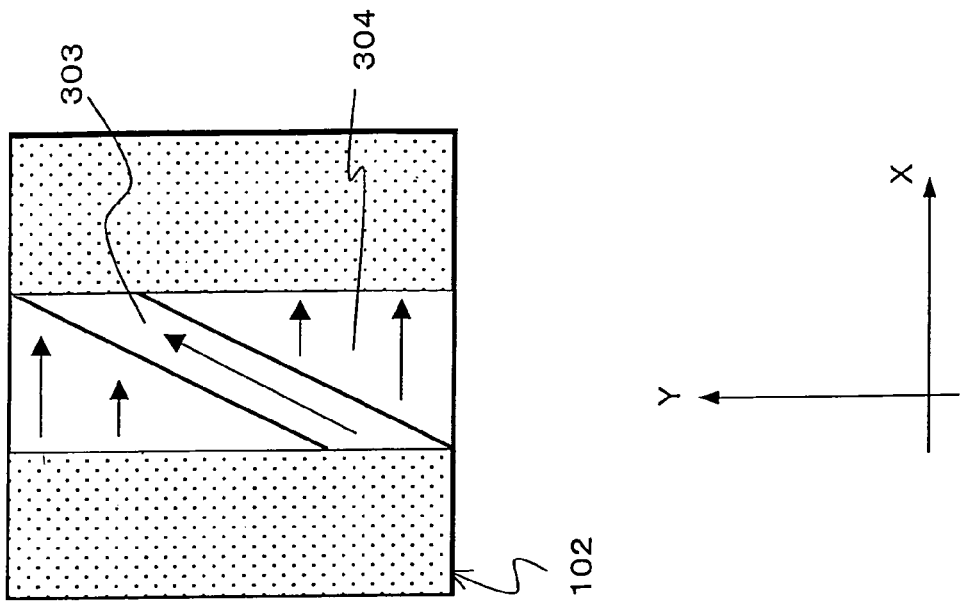
FIG. 7A shows a condition in which heat is transmitted parallel to the direction of the X axis in a section K1 of a small region 102.
Figure 7B:
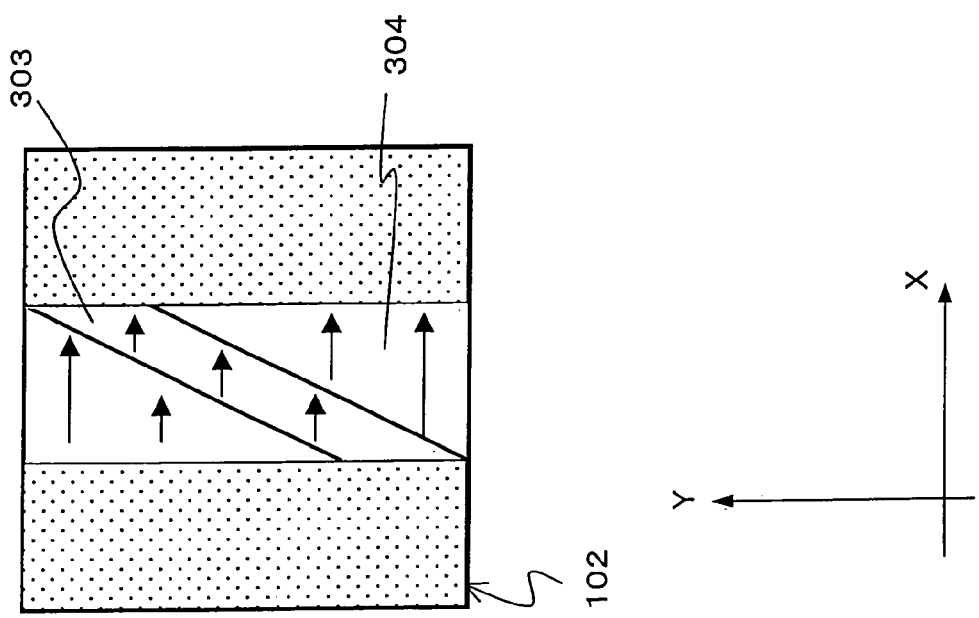
FIG. 7B shows a condition in which heat flows parallel to the direction of a wire pattern portion 303.

In the above, a method was described that calculates the equivalent thermal resistance in the X axis direction of the section K1, here, a correction example that is preferable in the above calculation method will be described. FIG. 7 shows a condition in which heat is transmitted in the section K1 of the small region 102 shown in FIG. 6. The arrows in FIG. 7 show the flow of heat. In the calculation method described above, as shown in FIG. 7A, calculation is performed with the assumption that heat is transmitted parallel to the X axis direction. However, from the results of heat analysis and the like, as in FIG. 7B, it is known that heat flows parallel to the direction of the wire pattern portion 303. Consequently, in the above calculation method, it is preferable to perform correction that takes into account the actual flow of heat.

Figure 8:
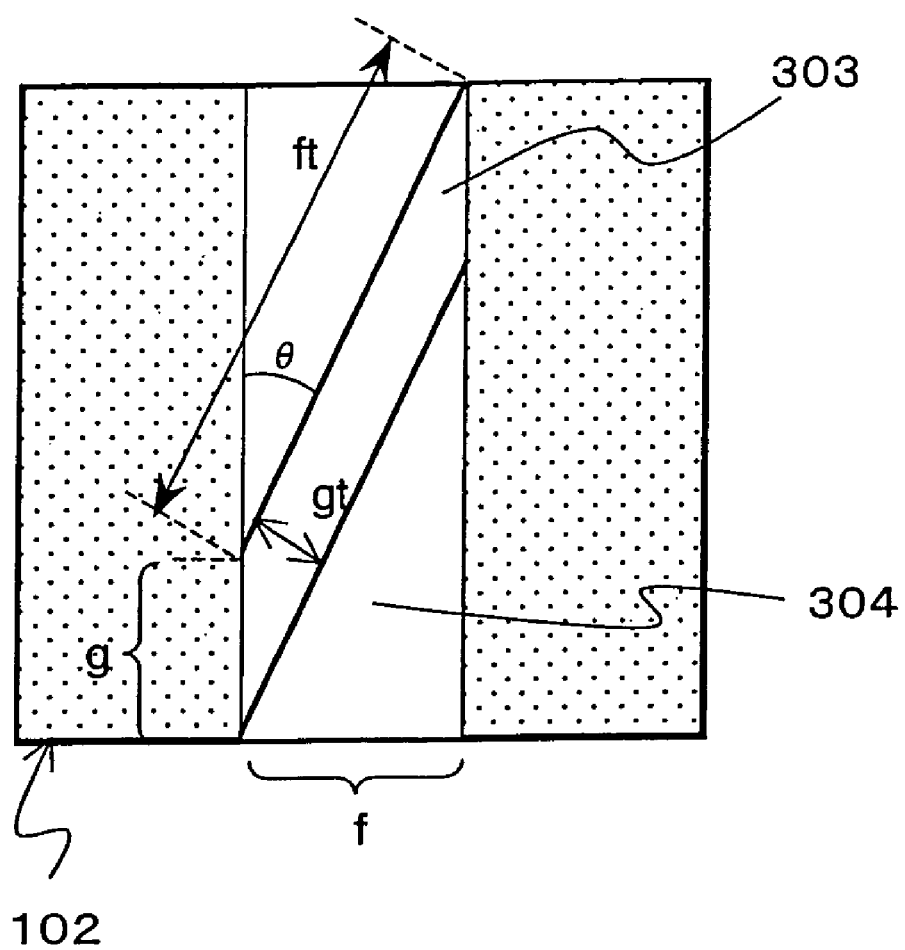
FIG. 8 shows a heat path length and a heat path width of a wire.
Figure 8:
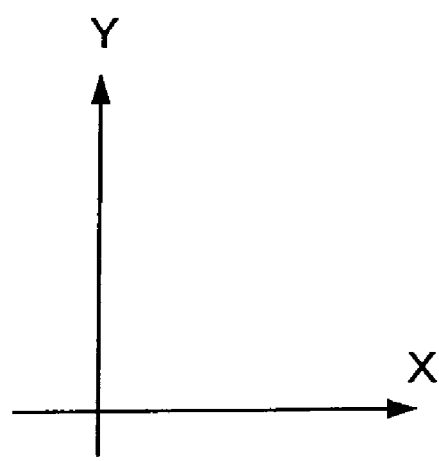

Specifically, as shown in FIG. 8, when the interval of the integrated section of the wire in the above calculation method prior to correction is f, and the heat path width is g, an actual wire heat path length $f_t$ is $f_t = f/\sin\theta$, and a heat path width $g_t$ is $g_t = g\sin\theta$. Considering that in this way, in actuality, the heat path length increases and the heat path width narrows, it is preferable to correct the thermal conductivity $\lambda$trace of the wire pattern portion 303. Specifically, in the above formula 6, formula 8, and formula 9, by performing the calculation with $\lambda$trace replaced by an apparent thermal conductivity $\sin^2\theta*\lambda$trace, calculation of a highly accurate equivalent thermal conductivity becomes possible.

As stated above, an equivalent thermal resistance Rx1 in the X axis direction for the section K1 shown in FIG. 6 is calculated. Likewise, thermal resistances Rx2 to Rx5 are calculated respectively in the X axis direction for sections K2 to K5. The processing of Steps S44 to S45 shown in FIG. 5 is repeated until the processing that obtains the equivalent thermal resistances Rx1 to Rx5 in the X axis direction for all of the sections K1 to K5 is completed.

In Step S46, when it is judged that the equivalent thermal resistances Rx1 to Rx5 in the X axis direction have been calculated for all of the sections of the small region 102, the equivalent material constant generating portion 64 generates an equivalent thermal resistance Rx in the X axis direction for the entire small region 102. The equivalent thermal resistance Rx in the X axis direction for the entire small region 102 is expressed by the sum of the equivalent thermal resistances Rx1 to Rx5 of the regions K1 to K5 (see formula below), because it is possible to consider the equivalent thermal resistances Rx1 to Rx5 of the regions K1 to K5 to be connected in series.

$$Rx = \Sigma Rxi \ (\Sigma \text{ is the summation of } i=1, 2, 3, 4, 5)$$

An equivalent thermal conductivity $\lambda X$ in the X axis direction of the small region 102 in the direction of XY plane is expressed by $\lambda x = Lx/(Rx \cdot Ly \cdot t)$, where Lx is the size in the X axis direction of the small region 102, Ly is the size in the Y axis direction, and t is the size (thickness) in the direction perpendicular to the XY plane.

When the equivalent thermal conductivity $\lambda x$ in the X axis direction is calculated, again in Step S42, the coordinate axis direction u of the calculation target is made the Y axis direction. Afterwards, by similarly repeating the processing in Step S43 to Step S47, an equivalent thermal conductivity $\lambda y$ in the Y axis direction of the small region 102 is calculated. When the equivalent thermal conductivity $\lambda x$ in the X axis direction and the equivalent thermal conductivity $\lambda y$ in the Y axis direction have been calculated, when the equivalent material constant generating portion 64 performs judgment (S48), again in Step S41, the small region interior calculation portion 6 next selects a new small region, and performs equivalent thermal conductivity calculation processing for the selected region (S49).

By performing the above processing for all of the small regions on the electronic circuit board 101, an equivalent thermal conductivity in the X axis direction and an equivalent thermal conductivity in the Y axis direction are calculated for each of the small regions. The calculated data is saved in the storage portion 2 (S25 in FIG. 3).

When an analysis system 13 performs, for example, thermal analysis or the like of the electronic circuit board 101, the equivalent thermal conductivities are used by reading them from the storage portion 2.

According to the present embodiment, both an equivalent thermal conductivity in the X axis direction and an equivalent thermal conductivity in the Y axis direction is obtained for each of the small regions. Thus, for example, for each of the small regions, anisotropy of the thermal conductivity is identified in the X and Y directions, in which heat is easily transmitted in the X axis direction but not easily transmitted in the Y axis direction. That is, equivalent thermal conductivities are obtained that have taken into consideration the directionality of the materials that constitute the electronic circuit board. As a result, at the same time that the calculation accuracy of the equivalent material constants is dramatically improved, it is possible to also realize a reduction in the calculation time.

This method of calculating an equivalent thermal conductivity, which is a first embodiment of the present invention, can be expressed by being stored as steps of a program executable by a computer.

This program executable by a computer is one embodiment of the equivalent material constant calculation program of the present invention.

Also, this program executable by a computer requires that data necessary to execute the processing of the program be input externally, such as from user operation for example, and also may include a prompting step to for such input, and a step to execute that input.

A program executable by a computer that includes these sorts of steps is also one embodiment of the equivalent material constant calculation program of the present invention.

Also, these programs executable by a computer are stored on a recording medium that can be read by a computer, and this recording medium is one embodiment of a recording medium on which the equivalent material constant calculation program of the present invention is stored.

Further, the recording medium that can be read by a computer on which this program executable by computer is stored, and the computer, along with any number of other constituent elements, constitute an equivalent thermal conductivity calculation device, and this is one embodiment of the equivalent material constant calculation device.

Embodiment 2

Following is a description of another embodiment of the present invention. Embodiment 2 is an equivalent material constant calculation system that calculates an equivalent material constant of a structure constituted by a plurality of materials, using an FFT method stated later.

The configuration of the equivalent material constant calculation system of the present embodiment is the same as the functional block diagram shown in FIG. 1A, except for the points stated below, so that the explanation thereof will be omitted here. The operation of the equivalent material constant calculation system of the present embodiment is the same as the flowchart shown in FIG. 3, except for the points stated below, so that explanation thereof also will be omitted here.

The processing of the system in the present embodiment differs from the processing of the system in Embodiment 1 in that the equivalent material constant calculation processing for the small region (Step S24) is different. Below, the equivalent material constant calculation processing for the small region in the present embodiment will be described with reference to FIG. 9 and FIG. 10.

Figure 9:
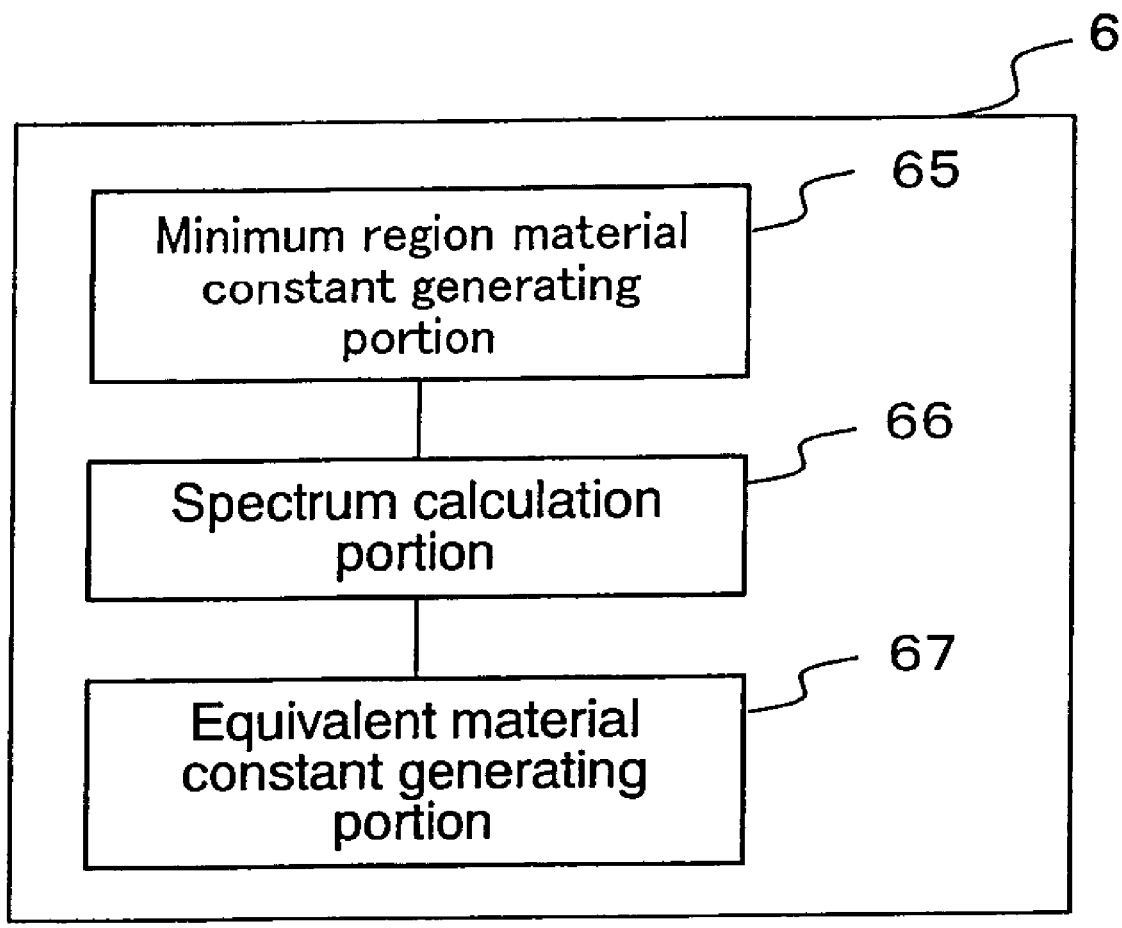
FIG. 9 is a functional block diagram that shows the configuration of a small region interior calculation portion 6.

FIG. 9 is a functional block diagram that shows the configuration of the small region interior calculation portion 6 in the present embodiment. As shown in FIG. 9, the small region interior calculation portion 6 includes a minimum region material constant generating portion 65, a spectrum calculation portion 66, and an equivalent material constant generating portion 67.

Figure 10:
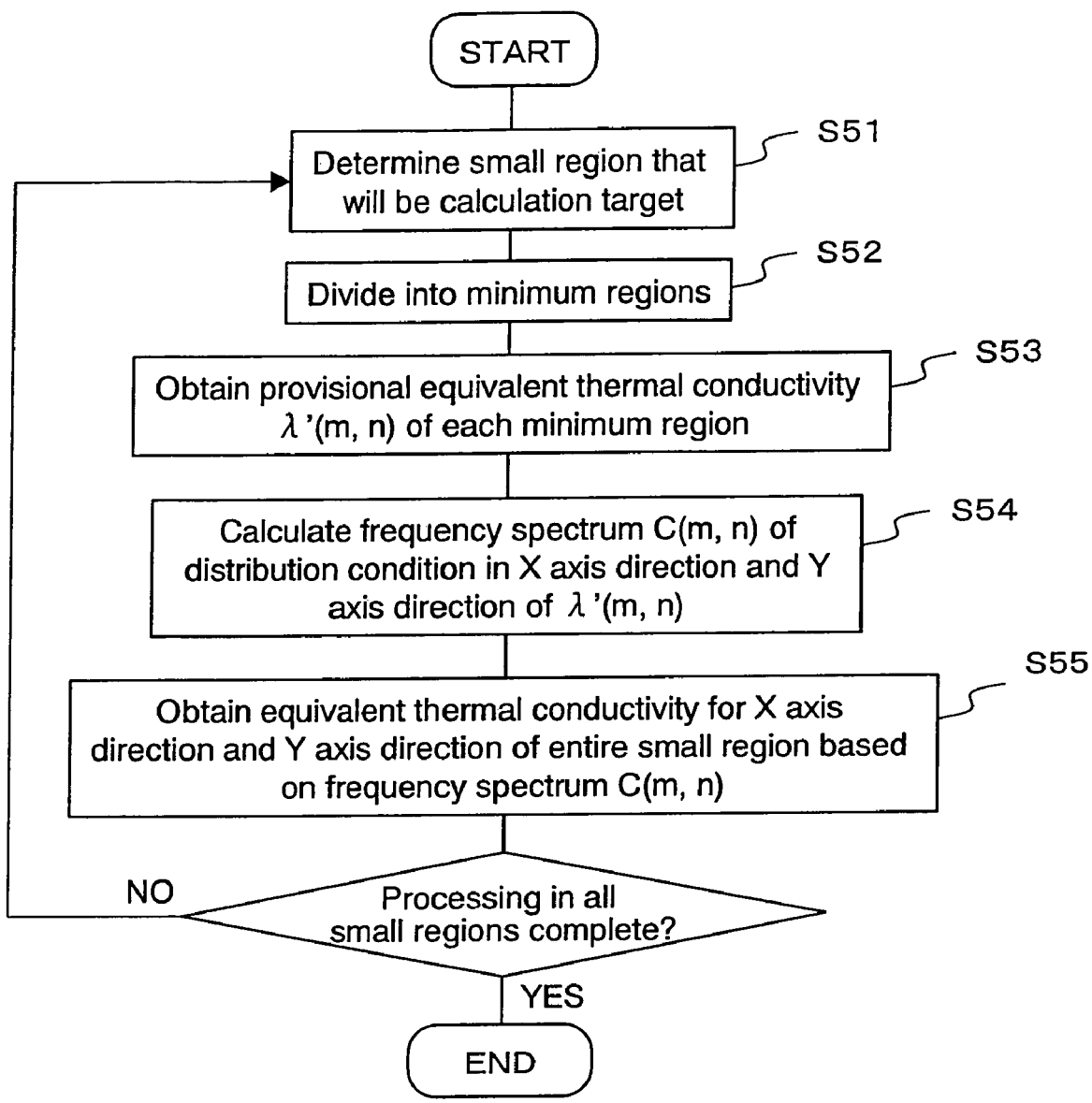
FIG. 10 is a flowchart that shows the detailed flow of processing that calculates an equivalent thermal conductivity for each small region 102.

FIG. 10 is a flowchart that shows the detailed flow of processing that calculates an equivalent thermal conductivity for each small region 102 in the present embodiment.

Figure 11:
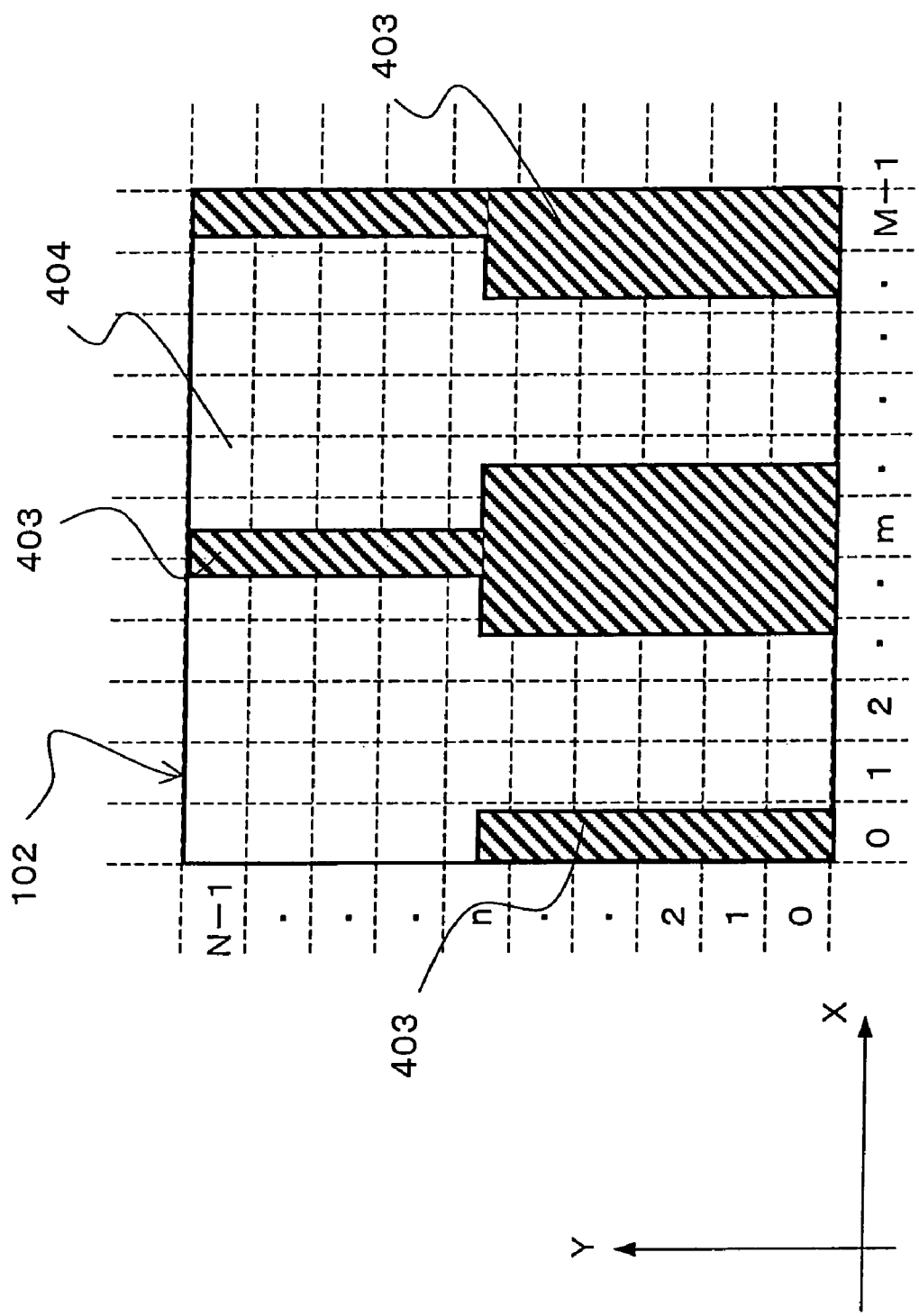
FIG. 11 shows an example of a selected small region 102.

First, the small region interior calculation portion 6 selects and determines the small region for which an equivalent thermal conductivity will be calculated, from among the divided small regions 102 (Step S51). FIG. 11 shows an example of a selected small region 102.

The small region 102 shown in FIG. 11 is configured from three wire pattern portions lined up with a fixed interval in the X axis direction (the portion of the non-wire portion 404), and each wire pattern portion 403 has a shape that continues in the Y axis direction. That is, the shape occupied by the wire pattern portions 403 in the small region 102 is a shape that is repeatedly distributed, with a high frequency (short wavelength) in the X axis direction and a low frequency in the Y axis direction (long wavelength).

In order to measure this quantitatively, the minimum region material constant generating portion 65, as shown in FIG. 11, again divides the small region 102 into small minimum regions (Step S52). For example, the small region 102 is divided into M-regions of 0 . . . m . . . M−1 in the X axis direction, and N-regions of 0 . . . n . . . N−1 in the Y axis direction. These respective minimum regions are made a minimum region (m, n).

Next, the minimum region material constant generating portion 65 defines a function that associates 1 or 0 with each minimum region (m, n) according to whether or not a wire pattern portion 403 is present in that minimum region (m, n). Alternatively, it defines a function f(m, n) for each minimum region (m, n) that associates an area ratio of the wire pattern portion 403 included in that minimum region (m, n).

For example, when a wire pattern portion 403 is present in the minimum region (0, 0), and the area ratio of that region is half or more, a function f(0, 0)=1 may be defined. Alternatively, the area ratio for the entire minimum region of the wire pattern portion 403 in the minimum region may be made the value of the function f. For example, when a wire pattern portion 403 is present in the minimum region (0, 0) and the area ratio of that region is about 0.9, a function f(0, 0)=0.9 may be defined.

Also, the function may be defined by more rigorously calculating the area ratio of the wire pattern portion 403 occupied in each minimum region and making that area ratio the value of f(m, n), or the function may defined by making the value of f(m, n) 1 or 0, depending on whether or not the area ratio of the wire pattern portion 403 occupied in each minimum region exceeds a specific threshold value (for example, 0.5 or 0.8).

Next, the minimum region material constant generating portion 65 calculates an equivalent thermal conductivity $\lambda'(m, n)$ of this minimum region (m, n) (Step S53). This equivalent thermal conductivity $\lambda'(m, n)$ of the minimum region (m, n) is made a provisional equivalent thermal conductivity $\lambda'(m, n)$. The calculation of $\lambda'(m, n)$ can be performed using, for example, formula 10. In formula 10, $\lambda$trace is the thermal conductivity of the material that constitutes the wire pattern portion 403, and $\lambda$insulator is the thermal conductivity of the material that constitutes the non-wire portion 404.

$$\lambda'(m,n) = \lambda\text{trace} f(m,n) + \lambda\text{insulator}(1-f(m,n)) \qquad \text{Formula 10}$$

Also, $\lambda'(m, n)$ may be calculated by applying, for example, the method of generating the equivalent material constant of the small region in Embodiment 1, that is, a method that integrates a function that expresses the boundaries of the wire pattern portion 403 and the non-wire portion 404.

Next, the frequency spectrum of the distribution status in the X axis direction and the Y axis direction of the provisional equivalent thermal conductivity $\lambda'(m, n)$ that accompanies the distribution profile of the wire pattern portion 403 in the small region 102, i.e. the frequency components, are calculated (Step S54). Specifically, a spectrum calculation portion 66 performs a two-dimensional discrete Fourier transformation for $\lambda'(m, n)$, and obtains each frequency component c (m, n) (frequency components corresponding to $2\pi m/M$ in the X axis direction, and corresponding to $2\pi n/N$ in the Y axis direction).

This formula that calculates frequency components c(m, n) is shown in formula 11. In formula 11, i expresses a complex number.

$$c(m, n) = \sum_{y=0}^{N-1} \sum_{x=0}^{M-1} \Delta x \cdot \exp(-2\pi i m y/N) \cdot \Delta y \cdot \exp(-2\pi i n x/M) \cdot \lambda'(x, y) \qquad \text{Formula 11}$$

Based on the frequency components c(m, n), the equivalent material constant generating portion 67 obtains respective equivalent thermal conductivities $\lambda$equivalent, X and $\lambda$equivalent, Y for the X axis direction and the Y axis direction of the entire small region 102 (Step S55). The respective equivalent thermal conductivities $\lambda$equivalent, X and $\lambda$equivalent, Y for the X axis direction and the Y axis direction of the entire small region 102 are obtained by calculating the sum of the frequency components c(m, n), which have been weighted. Specifically, they can be obtained by calculating the weighted sum of the powers to be fixed for the frequency components c(m, n) of the provisional equivalent thermal conductivity $\lambda'(m, n)$. This formula is shown in formula 12 and formula 13.

$$\lambda\text{equivalent, } X = \sum_r \sum_m \sum_n \alpha_{mnr}(c(m, n))^r \qquad \text{Formula 12}$$

$$\lambda\text{equivalent, } Y = \sum_r \sum_m \sum_n \beta_{mnr}(c(m, n))^r \qquad \text{Formula 13}$$

The power r and the weights ($\alpha$ and $\beta$) of the weighted sum are values determined by advance testing or a logical method. For example, it is possible to perform the calculation with $\alpha$ and $\beta$ as constants only where r=1. Similarly, it is possible to perform the calculation with $\alpha$ and $\beta$ as constants only where r=2, only where r=3, only where r=−1, only where r=−2, or only where r=−3. Also, for example, the weighted sum may by calculated where r=1 to 3 (for example, $\alpha=\alpha_1, \alpha_2, \alpha_3$, $\beta=\beta_1, \beta_2, \beta_3$). A weighted sum of r=2 to 10, a weighted sum of only odd-numbered powers r=−5 to +5, or a weighted sum of various other powers can be used.

An equivalent thermal conductivity in the X axis direction and the Y axis direction of the small region 102 can be calculated in the above manner.

In the present embodiment, in the above formula 11, using a two-dimensional discrete Fourier transformation, a frequency spectrum was obtained for the material constants in the X and Y directions, but it is also possible to obtain a frequency spectrum using the distribution of material constants in a three-dimensional space, i.e. in the X, Y, and Z directions, using a three-dimensional discrete Fourier transformation.

Embodiment 3

Following is a description of another embodiment of the present invention. Embodiment 3 is an equivalent material constant calculation system that calculates an equivalent material constant of a structure constituted by a plurality of materials.

The configuration of the equivalent material constant calculation system of the present embodiment is the same as the functional block diagram shown in FIG. 1A, except for the points stated below, so that the explanation thereof will be omitted here. The operation of the equivalent material constant calculation system of the present embodiment is the same as the flowchart shown in FIG. 3, except for the points stated below, so that the explanation thereof will also be omitted here.

The processing of the system in the present embodiment differs from the processing of the system in Embodiment 1 in that the equivalent material constant calculation processing for the small region (Step S24) is different. Below, the equivalent material constant calculation processing for the small region in the present embodiment will be described with reference to FIG. 12 and FIG. 13.

Figure 12:
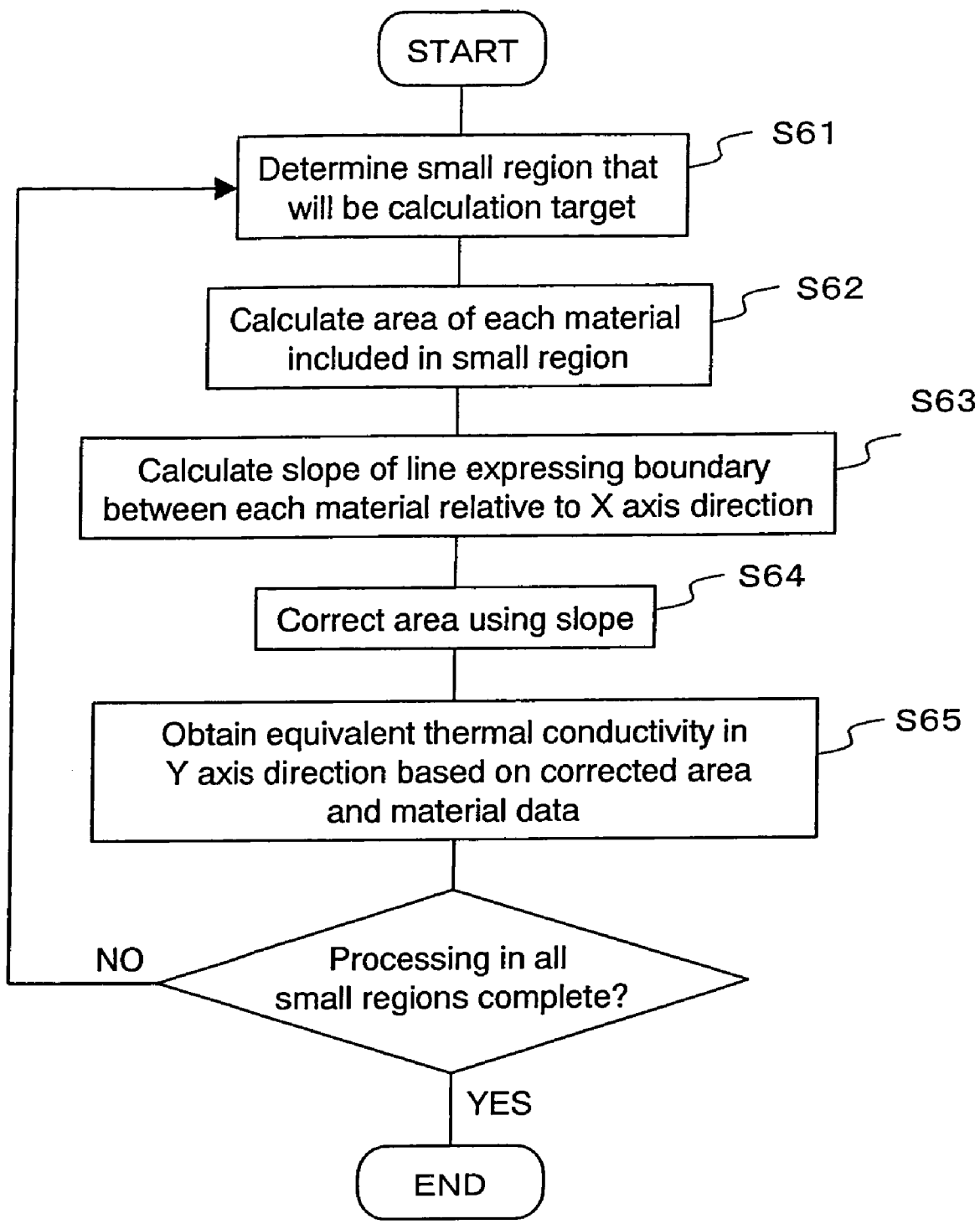
FIG. 12 is a flowchart that shows the detailed flow of processing that calculates an equivalent thermal conductivity for a small region 102.

FIG. 12 is a flowchart that shows the detailed flow of processing that calculates an equivalent thermal conductivity for the small region 102 in the present embodiment.

Figures 13A, 13B:
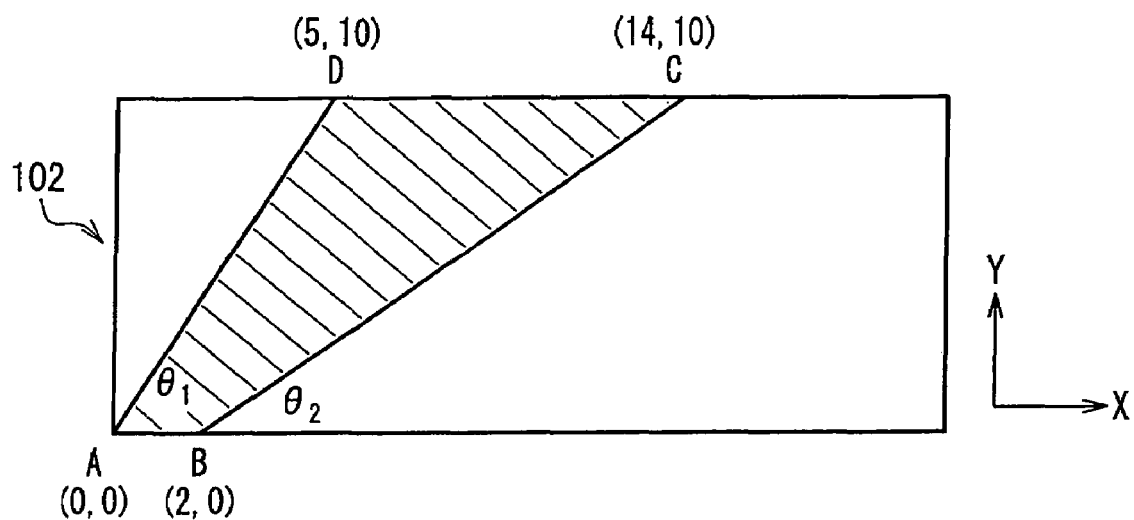
FIG. 13A shows an example of a selected small region 102.
FIG. 13B shows an example of equivalent material constants calculated respectively using an arithmetic mean, weighted mean, maximum value, and minimum value as θav.

First, the small region interior calculation portion 6 selects and determines the small region for which an equivalent thermal conductivity will be calculated, from among the divided small regions 102 (Step S61). FIG. 13A shows an example of a selected small region 102.

In the small region 102 shown in FIG. 13A, a trapezoidal portion with vertexes is the wire pattern portion, and the other portions are the non-wire portions. The wire pattern portions, are, for example, constituted by material such as copper, and the non-wire portions, are, for example, constituted by material such as epoxy.

The small region interior calculation portion 6 calculates the area of the trapezoid ABCD (Step S61). The coordinates of these trapezoid vertexes ABCD, for example, are expressed by the shape data that has been input with the shape data input portion 3. Thereby the area of the wire pattern portions is obtained.

Next, the small region interior calculation portion 6 obtains a slope relative to the X axis direction of a line that indicates a boundary between a wire pattern portion and a non-wire portion (Step 563). The slope is indicated by an angle, for example. In the example shown in FIG. 13A, an angle θ1 of the boundary line AD relative to the X axis, and an angle θ2 of the boundary line BC relative to the X axis are obtained. The small region interior calculation portion 6 also obtains an average value θav of these angles θ1 and θ2. The average value θav, for example, is a value of the arithmetic mean of angles θ1 and θ2.

The small region interior calculation portion 6 obtains an equivalent thermal conductivity λequivalent for the small region 102 using the average value θav, the material constant λtrace of the material that constitutes the wire pattern portions, and the area of the wire pattern portions.

The equivalent thermal conductivity λequivalent, for example, is expressed as in formula 14. In formula 14, the area ratio of the wire pattern portions in the small region 102 is made α, and the area ratio of the non-wire portions in the small region 102 is made (1−α). Also, the material constant of the material of the non-wire portions is made λinsulator.

$$\lambda\text{equivalent}=\sin^2 \theta_{av}\cdot\lambda\text{trace}\cdot\alpha+\lambda\text{insulator}\cdot(1-\alpha) \quad \text{Formula 14}$$

In formula 14 above, by multiplying λtrace by $\sin^2 \theta\text{av}$ and adding correction, the material constant in the Y axis direction of the small region 102 is calculated. That is, with a simple calculation, a material constant that takes directionality into consideration is obtained. When obtaining a material constant in the X axis direction of the small region 102, for example, it is preferable to obtain the slope relative to the Y axis of the boundary line between each material. By making the average value of the slope relative to the Y axis θav and substituting in above formula 14, it is possible to obtain a material constant in the X axis direction.

The average value θav is not limited to the arithmetic mean of the angles θ1 and θ2. For example, it is possible to make a geometric mean value of the angles θ1 and θ2 the average value θav. Or, for example, maximum and minimum values may be used in place of an average value.

FIG. 13B shows an example of equivalent material constants for the small region 102 calculated respectively using an arithmetic mean, geometric mean, maximum value, and minimum value as θav.

In this table, "precise analysis value" is an equivalent material constant calculated using a finite element method with sufficient accuracy to obtain a value close to reality.

The value of "no correction" is an equivalent material constant obtained based on the area ratio of the wire pattern portion and the non-wire portion without taking into consideration the slope of boundary lines. That is, the value of "no correction" is an equivalent material constant calculated without using $\sin^2 \theta\text{av}$ in formula 14.

The value of "maximum value" is an equivalent material constant calculated using the maximum values of the angles θ1 and θ2 for θav in formula 14. The value of "minimum value" is an equivalent material constant calculated using the minimum values of the angles θ1 and θ2 for θav.

The value of "arithmetic mean" is an equivalent material constant calculated using the arithmetic average of the angles θ1 and θ2 for θav. The value of "geometric mean" is an equivalent material constant calculated using the geometric mean of the angles θ1 and θ2 for θav.

In the table shown in FIG. 13B, the percentage of each value when the "precise analysis value" is made 100% is also shown. From this chart, it is understood that the weighted average value and the arithmetic average value are extremely close to the precise analysis value.

Embodiment 4

Following is a description of another embodiment of the present invention. Embodiment 4 is an equivalent material constant calculation system that, using a proportional allocation method, calculates an equivalent material constant of individual solids included in a structure constituted from a plurality of materials, and also calculates an equivalent material constant for a region in which this plurality of solids has been combined.

Figure 14:
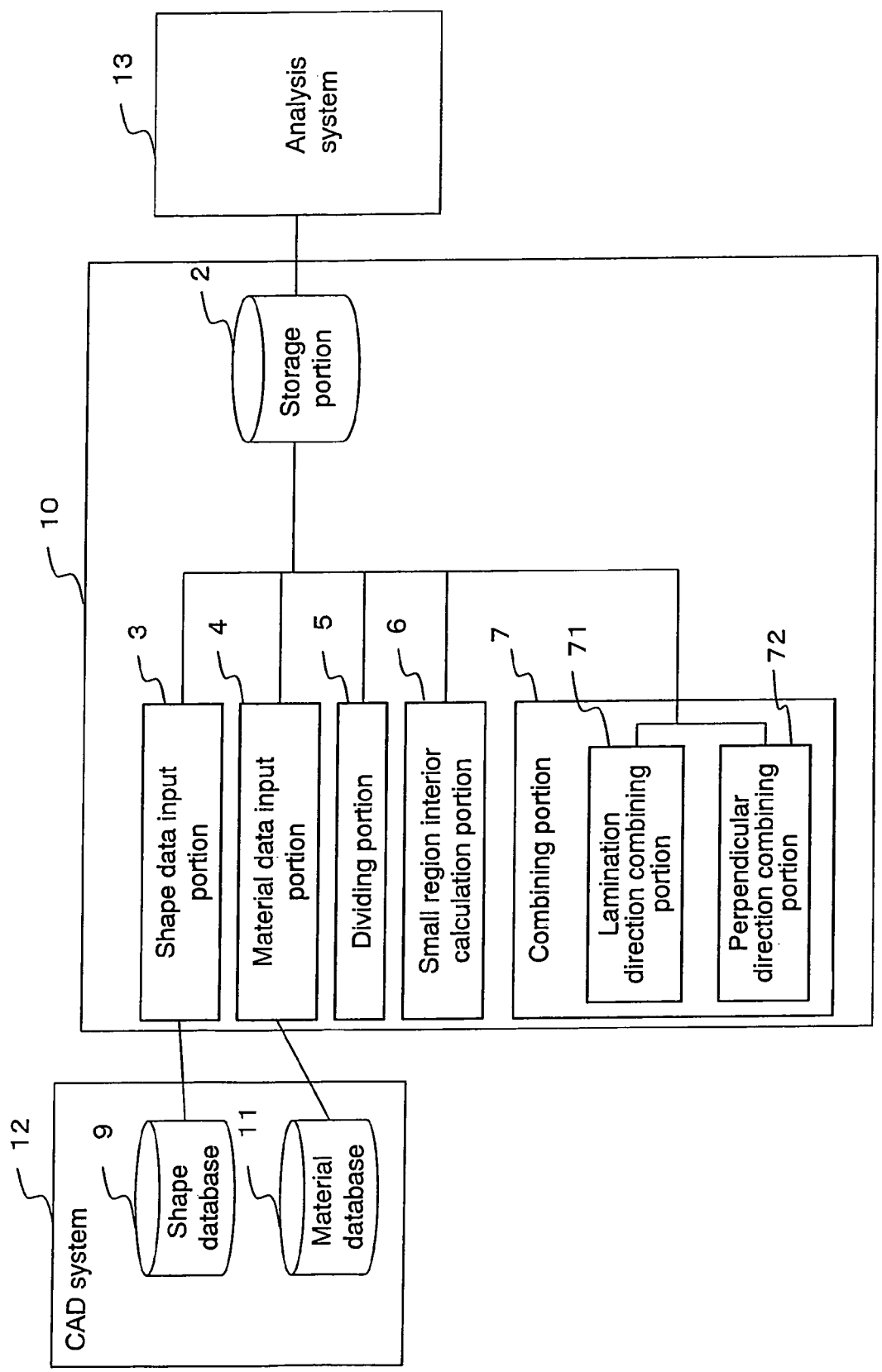
FIG. 14 is a functional block diagram that shows an example of the configuration of an equivalent material constant calculation system 10.

FIG. 14 is a functional block diagram that shows an example of a configuration of an equivalent material constant calculation system 10 of the present embodiment. In the block diagram shown in FIG. 14, the same numerals are attached to the same blocks as the block diagram shown in FIG. 1A, and their explanation is not repeated.

The block diagram shown in FIG. 14 differs from FIG. 1A in that a combined portion 7 is provided. The combined portion 7 includes a lamination direction combining portion 71 and a perpendicular direction combining portion 72. The lamination direction combining portion 71 obtains an equivalent material constant of a region in which the small regions divided by the dividing portion 5 are combined in the lamination direction. The perpendicular direction combining portion 72 obtains an equivalent material constant of a region in which adjacent small regions have been combined in the direction perpendicular to the lamination direction of the small regions.

Figure 15:
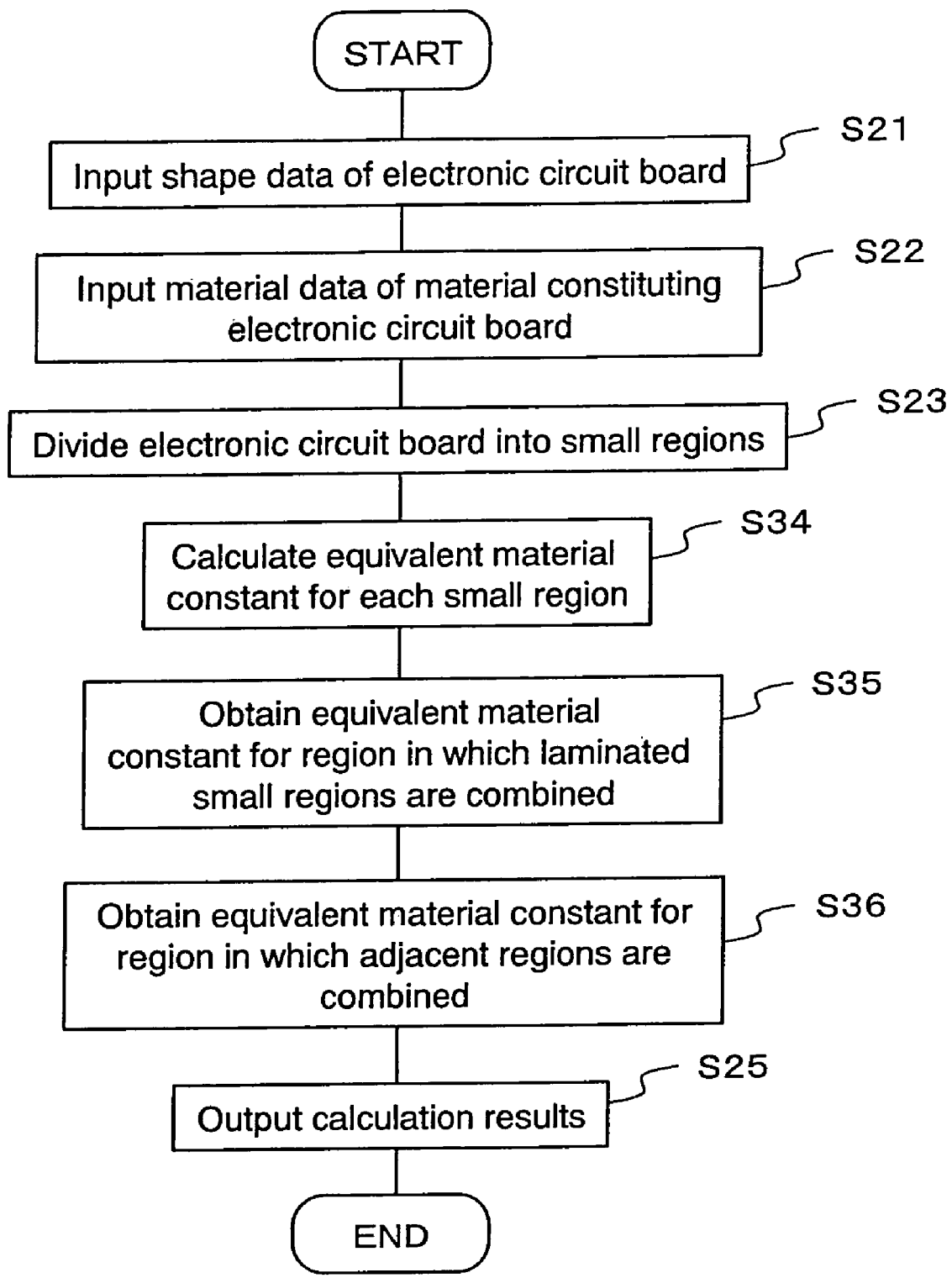
FIG. 15 is a flowchart that shows the operation of an equivalent material constant calculation system.

FIG. 15 is a flowchart that shows the operation of the equivalent material constant calculation system of the present embodiment. In the flowchart shown in FIG. 15, the same numerals are attached to steps that are the same as in the flowchart shown in FIG. 3, and their explanation is not repeated.

The flowchart shown in FIG. 15 is different from FIG. 3 in that the processing of Step S35 and Step S36 is newly added. Also, the processing that obtains equivalent material constants for each small region in FIG. 15 (S34) is different from the processing that obtains equivalent material constants for each small region in FIG. 3. First, the details of the processing in Step S34 will be described.

Figure 16:
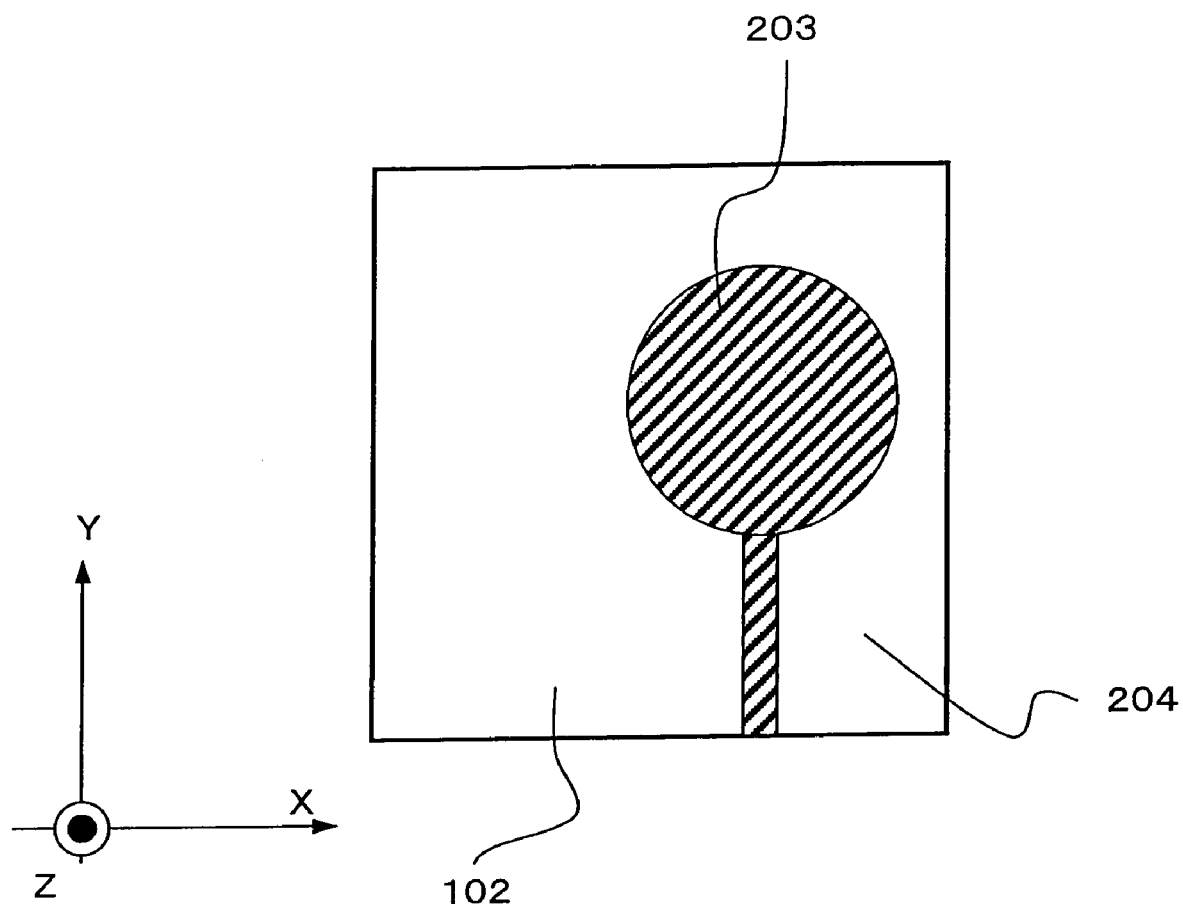
FIG. 16 shows one selected small region 102.

First, the small region interior calculation portion 6 selects and determines the small region for which an equivalent thermal conductivity will be calculated, from among the divided small regions 102. FIG. 16 shows an example of a selected small region 102.

This selected small region 102 is constituted from a portion that is a round wire pattern portion 203 that occupies about ¼ of the area of the entire small region 102, a portion that is a wire pattern portion 203 that is a thin lead line drawn out from the round portion, and a non-wire portion 204, which is the remaining portion of the small region 102.

The position and diameter of the round wire pattern portion 203 portion and position, width, length, and the like of the thin lead line wire pattern portion 203 portion are stored in the storage portion 2 as the shape data input by the shape data input portion. So when prescribing the position coordinates, the length in the X axis direction and the length in Y axis direction of this small region 102, it is possible to calculate directly the area of the wire pattern portions 203 and the area of the non-wire portion 204 in this small region 102, and the area ratio of these ratios.

The area ratio of the wire pattern portions 203 in the small region 102 is made α, and the area ratio of the non-wire portion 204 in the small region 102 is made (1−α). The thermal conductivity of the material that constitutes the wire pattern portions 203 is made λtrace, and the thermal conductivity of the material that constitutes the non-wire portion 204 is made λinsulator. The thermal conductivity λequivalent of the small region 102 is expressed as in formula 15.

$$\lambda\text{equivalent} = \lambda\text{trace}\alpha + \lambda\text{insulator}(1-\alpha) \quad \text{Formula 15}$$

Regarding the thermal conductivity λequivalent expressed in the above formula 15, the thermal conductivity in the X axis direction and the thermal conductivity in the Y axis direction are not necessarily distinguished. For example, it is possible to consider the thermal conductivity in the X axis direction and the thermal conductivity in the Y axis direction as having the same λequivalent.

Thus anisotropy is not taken into consideration in the thermal conductivity λequivalent, and it has low accuracy. In order to increase accuracy, it is necessary to divide the electronic circuit board more finely, and obtain equivalent material constants for a greater number of small regions. However, when the number of small regions is large, the number of output equivalent material constants also increases to that extent. As a result, analysis processing also becomes difficult when performing analysis using the output equivalent material constants, and efficiency worsens.

Consequently, it becomes necessary to decrease the amount of output data, while maintaining a particular level of accuracy for the equivalent material constants. Therefore, in the present embodiment, processing (S35 and S36) is provided that obtains an equivalent material constant for a region in which a plurality of adjacent small regions have been combined.

Following is a description of this processing (S35 and S36). By adding this processing after Step S24 in the flowchart shown in FIG. 3, it can be applied to Embodiment 1, Embodiment 2, and Embodiment 3 also. Thus, the processing below is described assuming that the thermal conductivity λequivalent in the X axis direction and the thermal conductivity λequivalent in the Y axis direction both have been obtained for the small region 102, as in the case of Embodiment 1-3.

In Step S34, when the equivalent thermal conductivity of each small region 102 is calculated, the lamination direction combining portion 71 obtains the thermal conductivity in the X axis direction and the thermal conductivity in the Y axis direction, for a region in which small regions for layers that have been layered in the Z axis direction have been combined in the lamination direction (Step S35).

Following is a description of the processing of Step S35, that is, processing that obtains an equivalent thermal conductivity for a region in which the small regions of each layer have been combined in the lamination direction.

Figure 17:
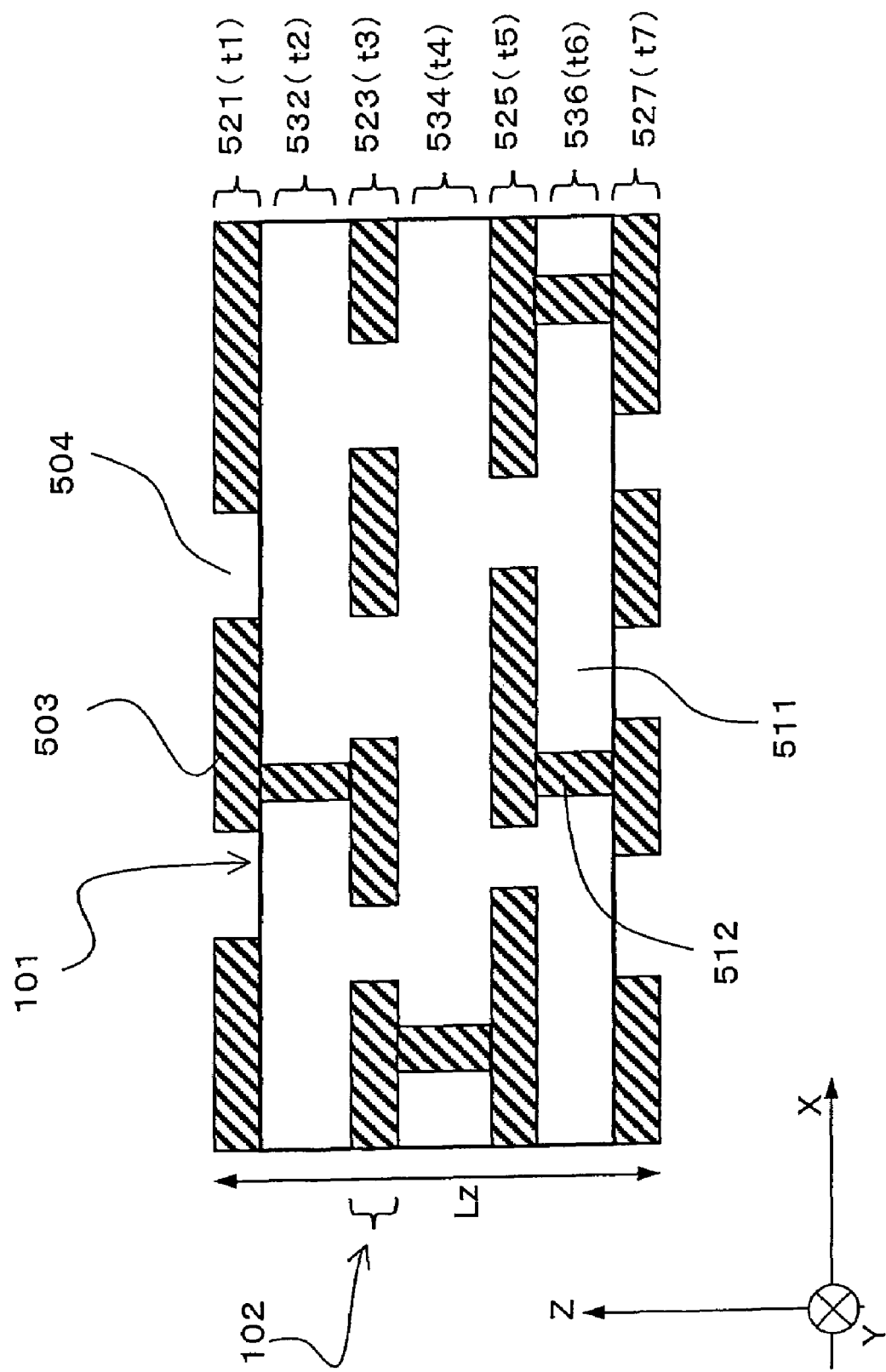
FIG. 17 is a cross-sectional diagram viewing one of the small regions 102 in the XZ plane.

FIG. 17 is a cross-sectional diagram in plane XZ, when the electronic circuit board 101 is divided into seven layers in the Z axis direction, the divided layers are further divided into small regions 102 in the XY plane, and a cross section including one of these further divided small regions 102 is viewed from the Y axis direction in a three-dimensional space.

This cross section including the small regions 102, when viewed as a cross-sectional diagram in the XZ plane, includes the small regions of seven layers parallel to the XY plane laminated in the Z axis direction. Those small regions of seven layers, beginning from the small region with the upper coordinates in the Z axis direction, are a wire layer 521, an insulation layer 532, a wire layer 523, an insulation layer 534, a wire layer 525, an insulation layer 536, and a wire layer 527, whose respective thicknesses are t1, t2, t3, t4, t5, t6, and t7.

The respective wire layers 521, 523, 525, and 537 are configured from the wire pattern portion 503 and the non-wire portion 504, and the wire pattern portion ordinarily is made of metal material or the like. The non-wire portion 504 may be made from an insulator portion 511, or may be a space in which there is nothing.

The respective insulation layers 532, 534, and 536 are configured by the insulator portion 511, but metal material or the like that constitutes the wire pattern portion 503 (such as a through-hole 512) also may be included in a portion thereof.

The equivalent thermal conductivity in the X axis direction of the small region of a layer No. i (i=1, 2, . . . 7) of the seven layers is made λequivalent,X,i, and the equivalent thermal conductivity in the Y axis direction of the small region of the layer No. i is made λequivalent,Y,i, and when the X axis direction and the Y axis direction are not particularly distinguished, their equivalent thermal conductivity is expressed by λequivalent,i. When doing so, an equivalent thermal resistance Requivalent,X,i in the X axis direction for the unit width (unit measurement in the Y axis direction) of the layer No. i is expressed by the reciprocal of the equivalent thermal conductivity λequivalent,X,i.

Requivalent,X,i=1/(λequivalent,X,i·ti)

Likewise, the equivalent thermal resistance Requivalent,Y,i in the Y axis direction of the layer No. i is 1/(λequivalent,Y,i·ti).

It is possible to consider that, when viewing the region in which the small regions of the seven small layers are all combined in the lamination direction (Z axis direction) from the X axis direction or the Y axis direction, the small regions of the seven layers (i=1 to 7) with equivalent thermal resistance Requivalent,i are connected in parallel. Accordingly, the equivalent thermal resistance Requivalent of the region in which the small regions 102 have been combined across all layers in the Z axis direction is expressed by formula 16.

$$\frac{1}{Requivalent} = \sum_i \lambda equivalent, i \cdot t_i \quad \text{Formula 16}$$

The equivalent thermal conductivity λequivalent in the X axis direction and the Y axis direction of a three-dimensional region in which the small regions 102 are combined across all layers in the Z axis direction can be calculated by dividing the reciprocal of the equivalent thermal resistance Requivalent expressed in formula 16 by an entire thickness Lz, and so it is expressed by formula 17.

$$\lambda equivalent = \frac{\sum_i \lambda equivalent, i \cdot t_i}{lz} \quad \text{Formula 17}$$

This formula in which the X axis direction and the Y axis direction are distinguished is expressed in formula 18 and formula 19.

$$\lambda equivalent, X = \frac{\sum_i \lambda equivalent, X, i \cdot t_i}{lz} \quad \text{Formula 18}$$

$$\lambda equivalent, Y = \frac{\sum_i \lambda equivalent, Y, i \cdot t_i}{lz} \quad \text{Formula 19}$$

As described above, in Step S35, it is possible to calculate the equivalent thermal resistance Requivalent,X in the X axis direction and the equivalent thermal resistance Requivalent,Y in the Y axis direction of a three-dimensional region in which the small regions 102 are combined across all layers in the lamination direction.

Next, based on the equivalent thermal resistance Requivalent obtained in Step S35, the perpendicular direction combining portion 72 obtains an equivalent material constant for a region in which a plurality of adjacent regions are combined (Step S36).

Figure 18:
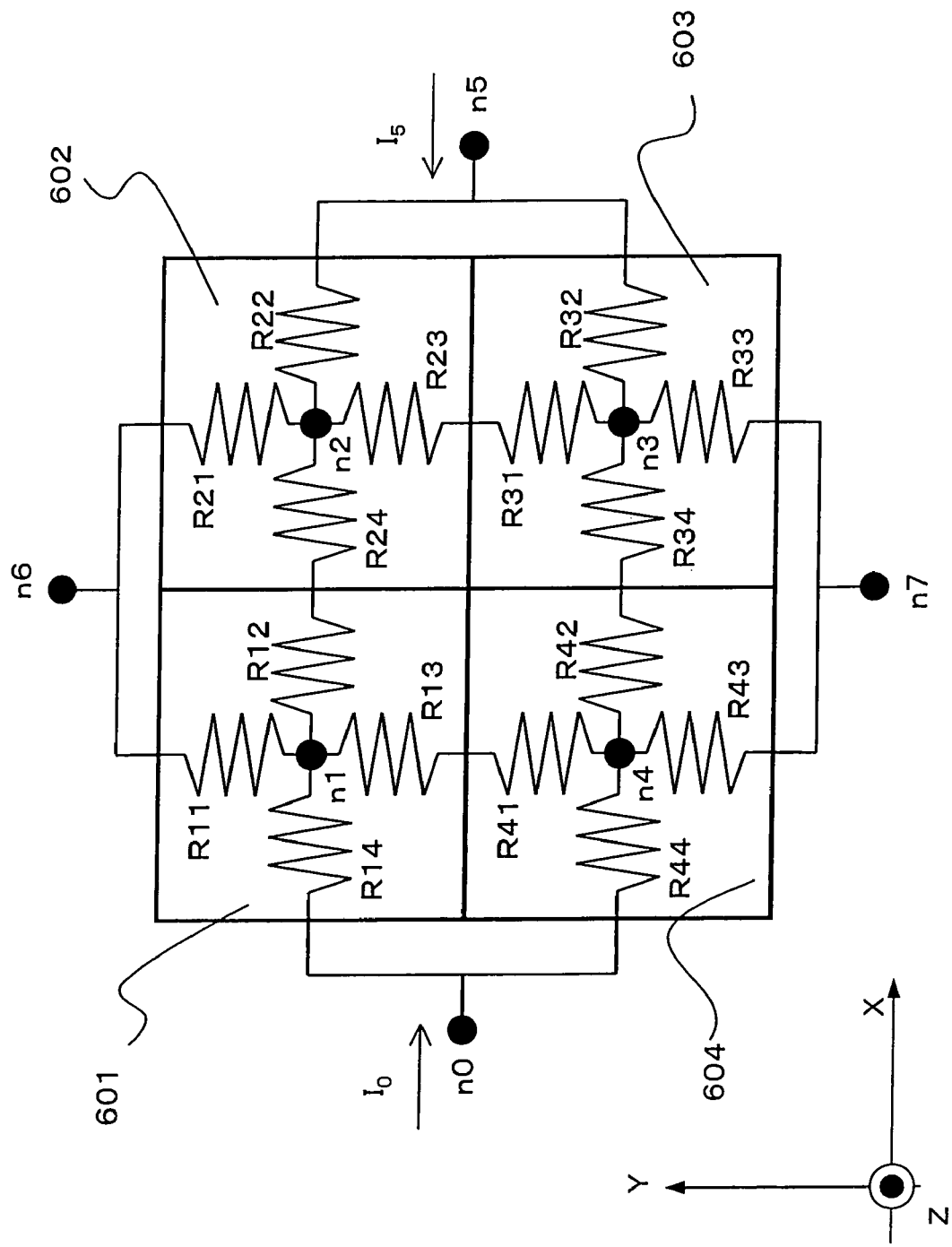
FIG. 18 is a plan view viewing four adjacent small regions 601, 602, 603, and 604 in the XY plane.

FIG. 18, for example, is a plan view showing four adjacent small regions 601, 602, 603, and 604 from the Z axis direction.

The small region 601, for example, in Step S35, is a three-dimensional region in which the small regions 102 are combined across all layers in the lamination direction. In that case, the small region 601 has the equivalent thermal resistance Requivalent,X in the X axis direction and the equivalent thermal resistance Requivalent,Y in the Y axis direction. Similarly, the other three small regions 602, 602, and 604 are three-dimensional regions in which the small regions 102 are combined across all layers in the lamination direction, respectively having an equivalent thermal resistance in the X axis direction and an equivalent thermal resistance in the Y axis direction.

Here, one small region 601 is expressed by a square with a center of, for example, n1. For the equivalent thermal resistance in the X axis direction of the small region 601, it is possible to consider R12 and R14 as being connected in series. R12 and R14 have the relationship shown in the formula below. In the below formula, 0<α<1.

R14=Requivalent,X·α

R12=Requivalent,X·(1−α)

The value of α is ordinarily 0.5, but it can be changed according to circumstances.

Likewise, for the equivalent thermal resistance in the Y axis direction of the small region 601, it is possible to consider R11 and R13 as being connected in series. This is also true for the other small regions 602, 603, and 604.

The equivalent thermal resistance in the X axis direction of the region in which the four small regions 601, 602, 603, and 604 can be considered to be a thermal resistance between n0 and n5. Also, because it is possible to consider that for the thermal resistance of the entire combined region, the thermal resistances R11 to R14, R21 to R24, R31, and R41 to R44 of the small regions 601, 602, 603, and 604 are connected as shown in FIG. 18, the thermal resistance between n0 and n5 can be calculated using Kirchoff's law in the calculation of electrical resistance. When the thermal resistance between n0 and n5 is calculated using Kirchoff's law in the calculation of electrical resistance, it is possible to use a matrix operation.

Here, an example of calculating the thermal resistance between n0 and n5 using Kirchoff's law is explained. In FIG. 18, the electrical potentials in nodes n0, n1, n2, n3, n4, and n5 are respectively made V1, V2, V3, V4, and V5. Here, because the sum of current that enters ni is 0, formulas 20 to 24 are satisfied. For example, the sum of current that enters node n0 is expressed by the left side of below formula 20, and this is 0. Likewise, formula 21 is satisfied at node n1, formula 22 is satisfied at node n2, formula 23 is satisfied at node n3, formula 24 is satisfied at node n4, and formula 25 is satisfied at node n5. Here, the current that enters node n0 is made $I_0$, and the current that enters node n5 is made $I_5$.

$$\frac{V_1 - V_0}{R14} + \frac{V_4 - V_0}{R44} + I_0 = 0 \quad \text{Formula 20}$$

$$\frac{V_1 - V_0}{R14} + \frac{V_4 - V_1}{R13 + R41} + \frac{V_2 - V_1}{R12 + R24} = 0 \quad \text{Formula 21}$$

-continued $$\frac{V_2 - V_1}{R24 + R12} + \frac{V_5 - V_2}{R22} + \frac{V_3 - V_2}{R31 + R23} = 0 \quad \text{Formula 22}$$

$$\frac{V_3 - V_2}{R31 + R23} + \frac{V_3 - V_4}{R34 + R42} + \frac{V_5 - V_3}{R32} = 0 \quad \text{Formula 23}$$

$$\frac{V_4 - V_0}{R44} + \frac{V_4 - V_1}{R13 + R41} + \frac{V_3 - V_4}{R34 + R42} = 0 \quad \text{Formula 24}$$

$$\frac{V_5 - V_2}{R22} + \frac{V_5 - V_3}{R32} + I_5 = 0 \quad \text{Formula 25}$$

Also, because the current that enters n0 and the current that exits from n5 are equal, below formula 26 is satisfied.

$$I_0 + I_5 = 0 \quad \text{Formula 26}$$

The seven formulas 20 through 26 can be expressed in matrix form. It is possible to obtain the values of V5, V0, and $I_0$ by simplifying each row of that determinant, using the Gauss-Jordan method, for example. It is possible to calculate a combined resistance $\lambda$eq,x between n0 and n5 by substituting these values into formula 27.

$$\lambda eq, x = \frac{V_5 - V_0}{I} \cdot \frac{lx}{lylz} \quad \text{Formula 27}$$

In formula 27, lx, ly, and lz are the sizes in the x, y, and z directions of the region in which the small regions 601, 602, 603, and 604 are combined, and I is $I_0$ or $I_5$.

The equivalent thermal resistance in the Y axis direction of the region in which the small regions 601, 602, 603, and 604 are combined can be considered as the thermal resistance between n6 and n7, and this also can be calculated in the same manner.

In FIG. 18, a method was described that obtains an equivalent thermal resistance for a region in which the adjacent small regions 601, 602, 603, and 604 are combined in the direction of the XY plane. Because this is also the same when considering a region in which adjacent regions are combined in a three-dimensional space, that explanation is omitted.

Also, the calculation method of an equivalent material constant for a region in which adjacent regions are combined is not limited to the above method using Kirchoff's law. For example, it is possible to use a finite element method, a calculus of finite differences, or the like.

Modified Example of a Combined Region Equivalent Material Constant Calculation Method Here, an example of a method that calculates an equivalent material constant for the region in which adjacent regions are combined using a finite element method will be explained. In the example of the method of solving with a finite element method, the material constant of the small region is deemed to be a spring constant, and a force that works in the region in which the small regions are combined is obtained.

Figure 19:
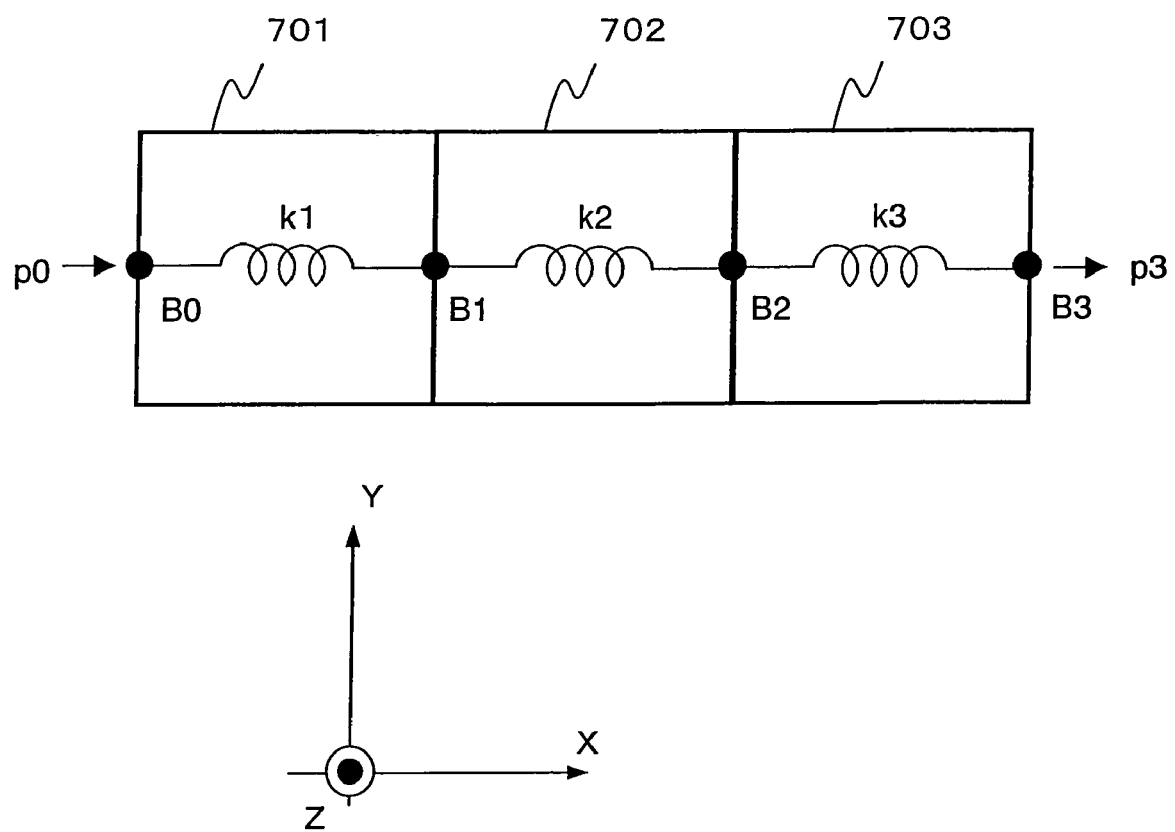
FIG. 19 is a plan view viewing three adjacent small regions 701, 702, and 703 from the direction of the Z axis.

FIG. 19 is, for example, a plan view viewing three adjacent small regions 701, 702, and 703 from the direction of the Z axis. The material constants possessed by the small regions 701, 702, and 703 are deemed to be X axis direction spring constants k1, k2, and k3, respectively. Using these spring constants in the X axis direction, by creating a stiffness equation and obtaining a solution with a matrix calculation, it is possible to obtain a combined equivalent material constant for the X axis direction.

Following is an explanation of an example of a method of creating a stiffness equation. In FIG. 19, external force that works at a node B0 is made p0, and external force that works at a node B3 is made, p3. Displacement at nodes B0, B1, B2, and B3 is made $u_0$, $u_1$, $u_2$, and $u_3$. The equilibrium of force at node B0 is expressed by the below equations.

$$k_1(u_0 - u_1) = p0 \quad \text{(Equation 1)}$$

In the same manner, the equilibrium at nodes B1, B2, and B3 is as follows:

$$-k_1(u_0 - u_1) + k_2(u_1 - u_2) = 0 \quad \text{(Equation 2)}$$

$$-k_2(u_1 - u_2) + k_3(u_2 - u_3) = 0 \quad \text{(Equation 3)}$$

$$-k_3(u_2 - u_3) = p3 \quad \text{(Equation 4)}$$

Expressed as a matrix, above equation 1 to 4 become below formula 28.

$$\begin{Bmatrix} p0 \\ 0 \\ 0 \\ p3 \end{Bmatrix} = \begin{bmatrix} k_1 & -k_1 & 0 & 0 \\ -k_1 & k_1 + k_2 & -k_2 & 0 \\ 0 & -k_2 & k_2 + k_3 & -k_3 \\ 0 & 0 & -k_3 & k_3 \end{bmatrix} \begin{Bmatrix} u_0 \\ u_1 \\ u_2 \\ u_3 \end{Bmatrix} \quad \text{Formula 28}$$

In above formula 28, output p3 is calculated from input of a suitable p0 and boundary condition (for example, $u_0 = 0$). From this p0 and p3, an equivalent spring constant is obtained for the region in which small regions 701, 702, and 703 are combined.

The above is a modified example of a combined region equivalent material constant calculation method. In FIG. 18 a case was explained in which the four small regions 601, 602, 603, and 604 are combined, but because this is the same if the combined region is constituted by a larger number of small regions 102, an explanation of such a case is omitted.

Also, in the present embodiment, an explanation was given with the equivalent thermal resistance as a material constant, but it is also possible to calculate the equivalent thermal conductivity by obtaining the reciprocal of the equivalent thermal resistance.

Also, in the present embodiment, an equivalent material constant is obtained for the region in which the divided small regions 102 are combined in the Z axis direction, and an equivalent material constant is obtained for a region in which these regions combined in the Z axis direction are further combined in the direction of the XY plane. The order of combination is not limited to this; for example, the small regions 102 may be combined in the Z axis direction after they are combined in the direction of the XY plane. The small regions 102 may be combined only in the Z axis direction, or only in the direction of the XY plane.

Also, when dividing the structure, it is not necessarily required to divide into each layer in the Z axis direction. For example, it is possible to divide into regions that reach into a three-dimensional space, in the manner of a cube, a rectangular solid, or the like. In the respective divided small regions, it is possible to perform the processing that calculates an equivalent material constant for each small region as disclosed in Embodiments 1 and 2, and obtain an equivalent material constant for a region in which adjacent small regions are combined by the method stated above.

Also, in the present embodiment, by way of example all of the materials that constitute the wire pattern portion 103 are the same, and it is assumed that the thermal conductivity is also the same, but the wire pattern portions 103 also may be constituted from a plurality of materials with different thermal conductivity. This is also true for the non-wire portion 104.

Embodiment 5

Figure 20:
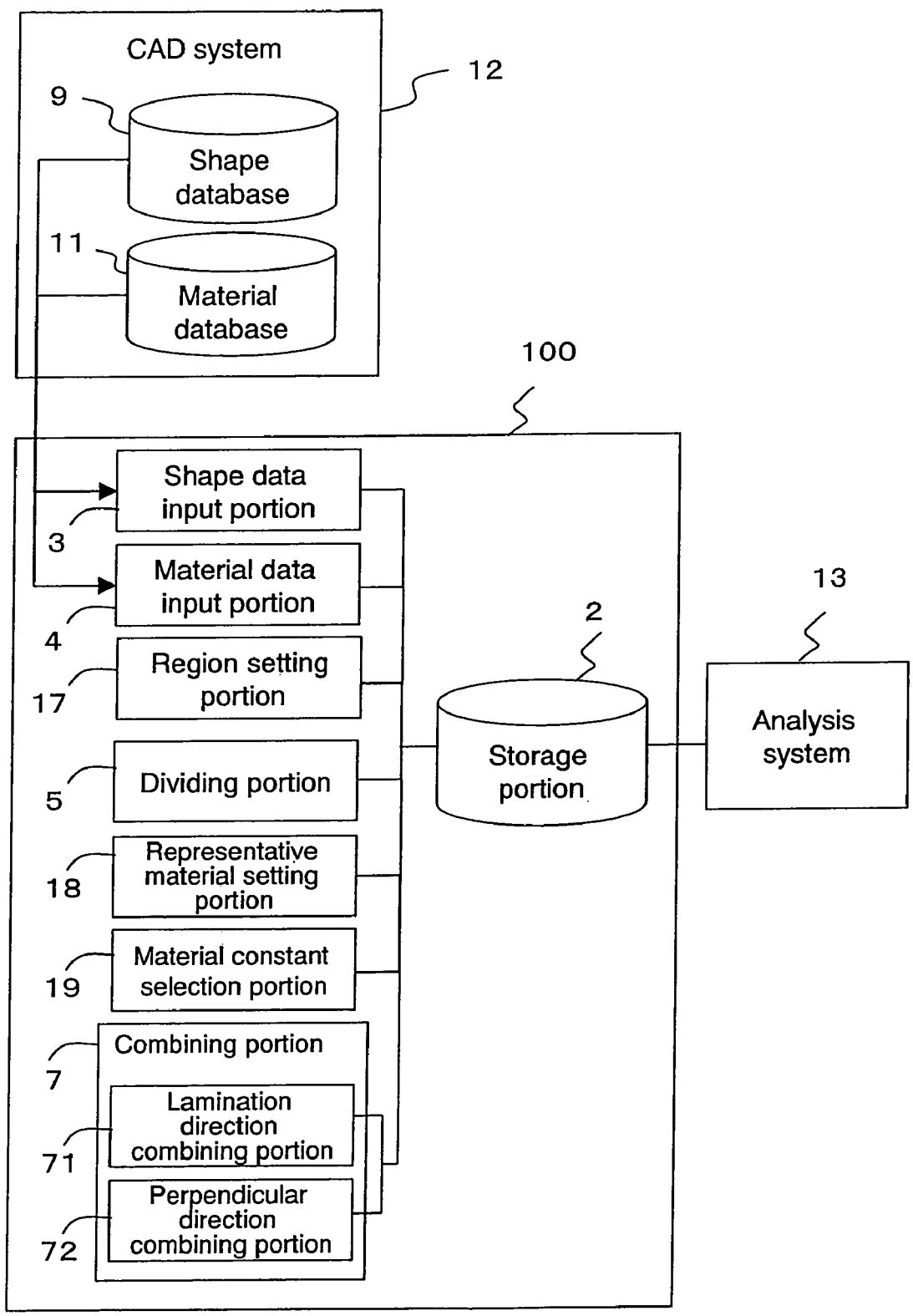
FIG. 20 is a functional block diagram that shows the configuration of an equivalent material constant calculation system.

FIG. 20 is a functional block diagram that shows an example of the configuration of an equivalent material constant calculation system 100 in the present embodiment. As shown in FIG. 20, the equivalent material constant calculation system 100 is configured from a storage portion 2, a shape data input portion 3, a material data input portion 4, a region setting portion 17, a dividing portion 5, a representative material determining portion 18, a material constant selection portion 19, and a combining portion 7.

The equivalent material constant calculation system 100 can be constructed on, for example, general purpose equipment such as a personal computer or a workstation (hereinafter, referred to as 'PC or the like'). The function of the shape data input portion 3, the material data input portion 4, the region setting portion 17, the dividing portion 5, the representative material determining portion 18, the material constant selection portion 19, and the combining portion 7 can be realized by the CPU of a PC or the like executing a predetermined program. The storage portion 2 can employ, other than a storage medium built into a PC or the like such as a hard disk or RAM, a portable storage medium such as a flexible disk or memory card, a storage medium in a storage device on a network, or the like.

The equivalent material constant calculation system 100 can be constructed by, for example, installing the program that allows a computer to execute the processing that is performed by the shape data input portion 3, the material data input portion 4, the region setting portion 17, the dividing portion 5, the representative material determining portion 18, the material constant selection portion 19, and the combining portion 7 from a storage medium such as a CD-ROM, or by download via a communications line, to a desired PC or the like.

The hardware configuration is not limited to the configuration shown in FIG. 20. For example, the function of the equivalent material constant calculation system 100 may be distributed to a plurality of PCs or the like that have been connected by an internet or a LAN such that communication is possible, for example.

The shape data input portion 3 inputs shape data of a structure for which an equivalent material constant will be calculated, and saves that data in the storage portion 2.

The shape data, for example, is shape data that expresses the shape of each material that constitutes the structure. An electronic circuit board can be given as an example of the structure. Ordinarily, shape data of an electronic circuit board often is created with a CAD system 12 for electronic circuit board design and saved in the CAD system 12. The shape data input portion 3 reads information stored in a shape database 9 of the CAD system 12 to the equivalent material constant calculation system 100.

Also, the input processing of the shape data input portion 3 is not limited to the case of reading shape data from the shape database 9. For example, it may read a file in which the shape data has been stored and input new data. Alternatively, the shape data input portion 3 may receive input of shape data from a designer via an input device such as a keyboard or a mouse provided in a PC or the like.

The material data input portion 4 inputs material constant data that expresses the material constants of the materials that constitute the structure. An example of data that expresses a material constant, if the structure is an electronic circuit board, is the material constant (for example, a thermal conductivity) of a material that constitutes the electronic circuit board. Material constant data of the electronic circuit board can be read by the material data input portion 4 when that information is saved in a material database 11 in the CAD system 12 for electronic circuit board design. Also, the possibility of input via a file, keyboard, mouse, or the like is the same as for the shape data input portion 3.

The region setting portion 17 sets a region in which an equivalent material constant for the structure will be obtained. The region in which an equivalent material constant will be obtained can be made a part of the structure or the entire structure. The region setting portion 17, for example, may receive input of data that indicates the region in which an equivalent material constant will be obtained from a designer via an input device such as a keyboard or a mouse provided in a PC or the like. Thereby, the designer can designate a region within the structure in which an equivalent material constant is desired to be obtained.

The dividing portion 5 divides the structure expressed by the shape data stored in the storage portion 2 into a plurality of small regions. The dividing portion 5 divides the region set by the region setting portion 17 into a plurality of small regions. The representative material determining portion 18 determines a material that represents the divided small regions. The material constant selection portion 19 selects the material constant of the material that represents the small region determined by the representative material determining portion 18 from the material constants input by the material data input portion 2.

The combined portion 7 includes a lamination direction combining portion 71 and a perpendicular direction combining portion 72. The lamination direction combining portion 71 combines, from among the small regions divided by the dividing portion 5, a plurality of adjacent small regions in the lamination direction, and obtains an equivalent material constant. The perpendicular direction combining portion 72 combines a plurality of adjacent small regions in the direction perpendicular to the lamination direction, and obtains an equivalent material constant. Here, the order in which the lamination direction combining portion 71 and the perpendicular direction combining portion 72 are allowed to operate may begin with either the lamination direction combining portion 71 or the perpendicular direction combining portion 72. Also only the lamination direction combining portion 71 may be allowed to operate, or only the perpendicular direction combining portion 72 may be allowed to operate.

The equivalent material constants obtained in this manner are saved in the storage portion 2 along with the position and dimensions of the combined small regions. Data related to the equivalent material constants saved in the storage portion 2 is delivered to an analysis system 13 as necessary. In the analysis system 13, analysis of the flow of heat, stress distribution, electromagnetic fields, hydrokinetics, and the like of the structure are performed using the delivered data.

Figure 21:
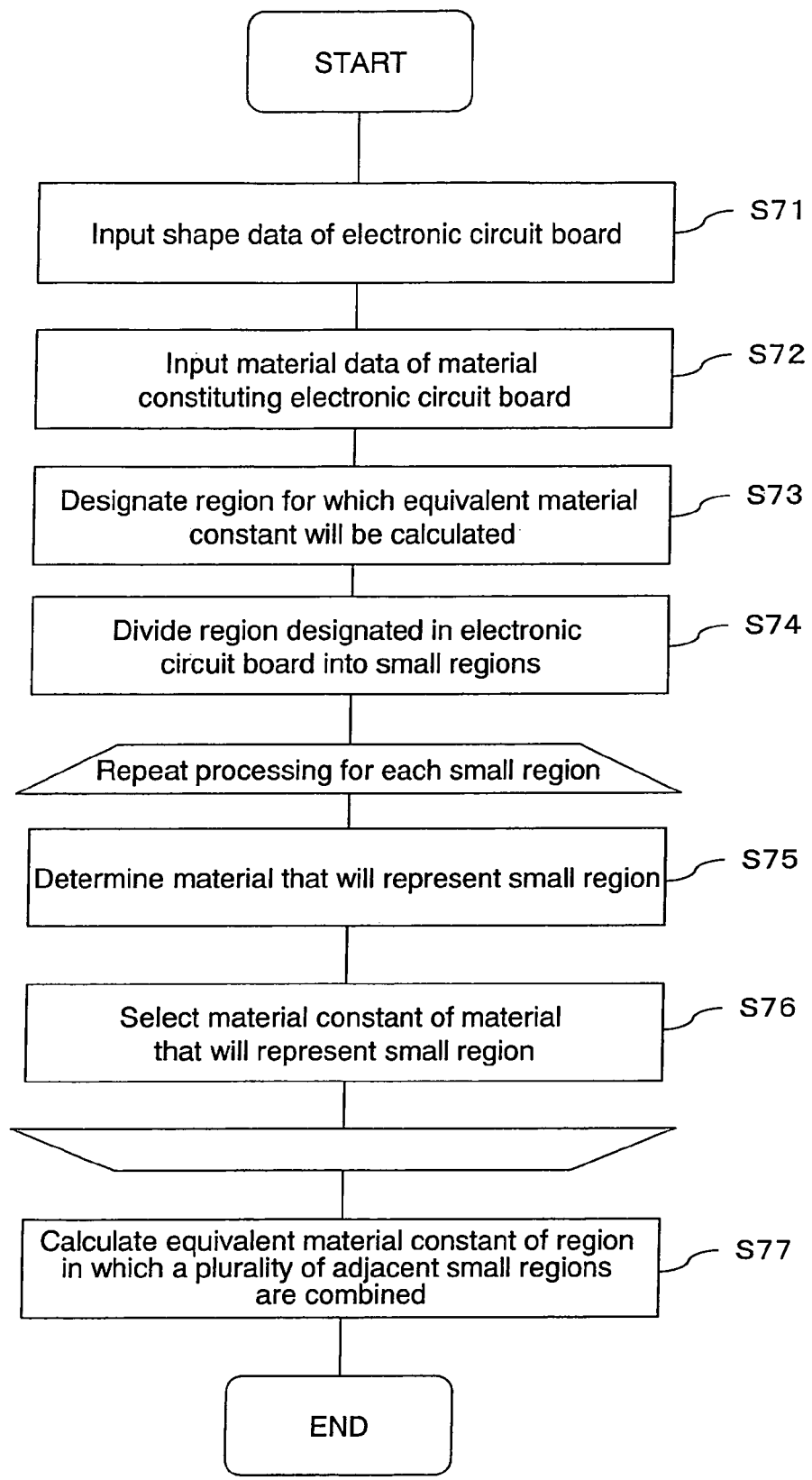
FIG. 21 is a flowchart that shows the operation of an equivalent material constant calculation system 100.

FIG. 21 is a flowchart that shows the operation of the equivalent material constant calculation system 100. FIG. 4 shows an example of the shape of a wire layer included in an electronic circuit board that is the target of an equivalent thermal conductivity calculation.

Following is a description of the flow of operation of the equivalent material constant calculation system 100, with reference to FIG. 20, FIG. 21, and FIG. 4. Here, as one example, processing is described that calculates an equivalent thermal conductivity of an electronic circuit board.

First, the shape data input portion 3 inputs shape data of the electric circuit board that will be the target of the equivalent thermal conductivity calculation (Step S71). The shape data of the electric circuit board is created with the CAD system 12, for example. The electric circuit board ordinarily is configured by alternately layering wire layers and insulation layers.

FIG. 4 is a plan view of a plane perpendicular to the lamination direction of the electronic circuit board, i.e., a wire layer in the XY plane. The wire layer of an electronic circuit board 101 is configured from a wire pattern portion 103 and a non-wire portion 104. Ordinarily the wire pattern portion 103 is constituted by material with a comparatively high thermal conductivity such as metal material, and the non-wire portion 104 is often constituted by material with a comparatively low thermal conductivity such as glass, resin, ceramics, or composites of these.

The material data input portion 4 inputs material constant data of the materials that constitute the electronic circuit board 101 (Step S72). As material constant data, for example, the thermal conductivity (λtrace) of the wire material, which is metal material that constitutes the wire pattern portion 103 of the electronic circuit board 101, and the thermal conductivity (λinsulator) of the insulator material, which is resin material that constitutes the non-wire portion 104, are input.

The region setting portion 17 sets a region for which an equivalent material will be calculated, which is a region included in the electronic circuit board 101 (Step S73). The region for which an equivalent material will be calculated is designated by input from a designer, for example. In the present embodiment, a case is described in which the entire electronic circuit board 101 is set as the region for which an equivalent material will be calculated.

The region set by the region setting portion 17 is not limited to the case in which the region is the entire electronic circuit board 101; a region that is a portion of the electronic circuit board 101 also may be set. For example, it is possible to remove a region where it is not necessary to obtain an equivalent material constant, such as an edge portion of the electronic circuit board 101 where there are few wire patterns, from the set region. It is possible to omit the processing by the dividing portion 5, the representative material determining portion 18, the material constant selection portion 19, and the combining portion 7 for the region removed from the set region. By doing so, the calculation load for the equivalent material constant calculation is lightened.

Because the shapes of the wire pattern portion 103 and the non-wire portion 104 that constitute the electronic circuit board 101 are extremely complicated, in order to make the subsequent processing simple, the dividing portion 5 divides the electronic circuit board 101 into a plurality of small regions (Step S74).

The dividing portion 5, for example, divides the electronic circuit board 101 into layers of each wire layer or insulation layer in the Z axis direction. Further, the dividing portion 5 perpendicularly divides each layer in a respective first axis and second axis of Cartesian coordinates set as desired. That is, the dividing portion 5 divides each divided layer in the XY plane. The small region 102 is one of the divided small regions.

Division in the direction of the Z axis can performed for each of the wire layers and insulation layers that constitute the electronic circuit board 101. Division in the direction of the XY plane, for example, as shown in FIG. 4, can divide a layer into 11 equal divisions in the direction of the X axis and 10 equal divisions in the direction of the Y axis, dividing the whole into 110 small regions. It is not necessary for the division into small regions to divide in equal parts in each direction. It is also possible to divide into small regions with different sizes as necessary.

It does not matter if this division into the small regions is the same for each wire layer and insulation layer, or if it is different.

The fineness of the division into small regions can be set as necessary. For example, it is possible to divide the small regions 102 shown in FIG. 4 more finely, and it is also possible to divide a size equal to four of the small regions 102 as one small region.

Figure 22:
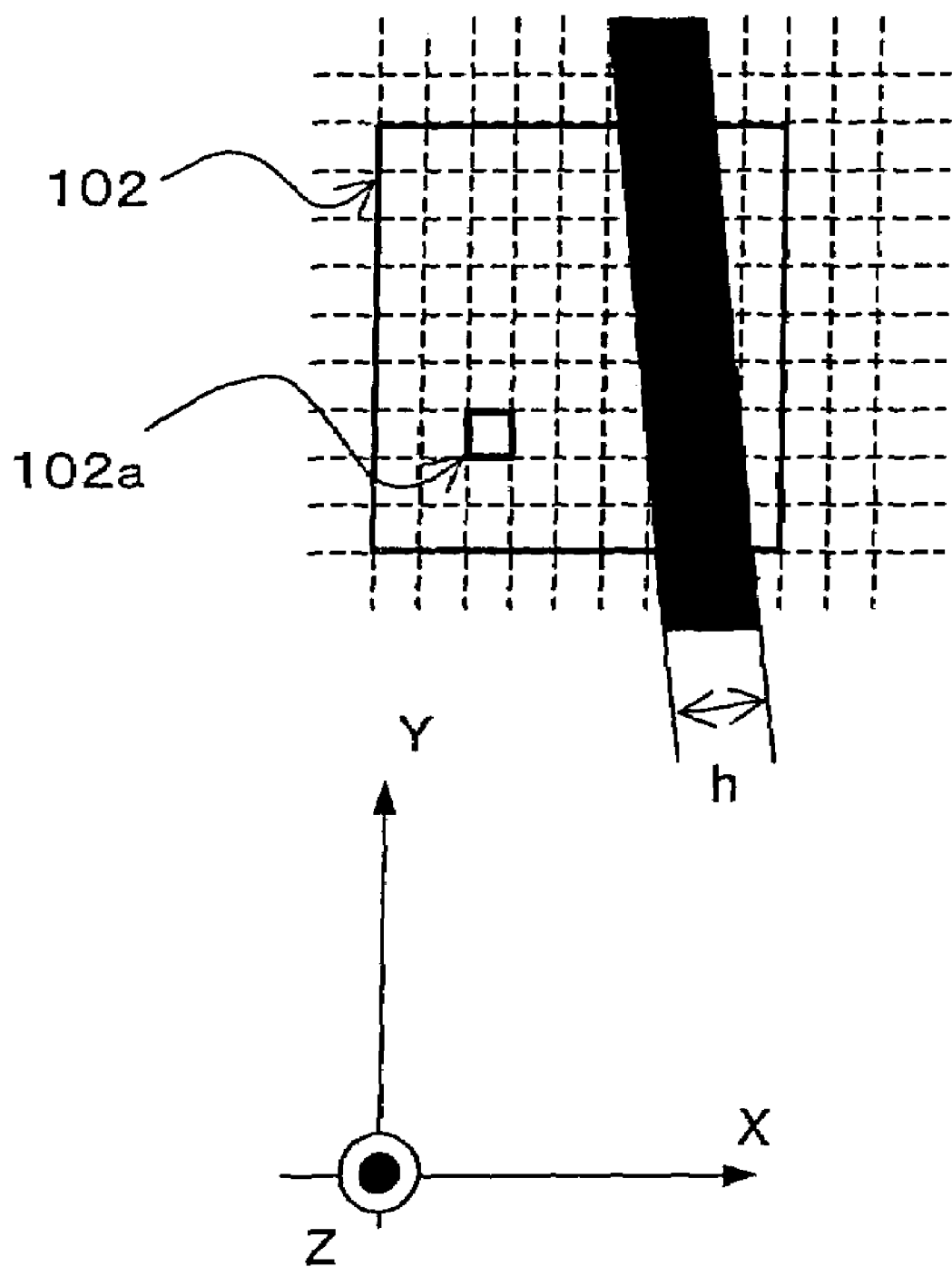
FIG. 22 shows an example in which small regions 102 are more finely divided.

Here, when setting the dividing width to be less than the smallest wire width of each layer, accuracy further increases. FIG. 22 shows an example of a case in which the small regions 102 are more finely divided, and the dividing width is made not more than the wire width. The example shown in FIG. 22 is an example of a case in which the small regions 102 in FIG. 4 have been further divided. A small region 102a is one of the divided small regions. The dividing width of the small region 102a is smaller than a wire width h.

Next, referring to FIG. 21, the representative material determining portion 18 determines the material that represents the respective small regions (Step S75). The representative material determining portion 18, for example, can make a material that is positioned in the center of a small region the representative material of that small region. The representative material determining portion 18 also may decide that a material in a defined location in the small region is the representative material; it is not limited to material located in the center of the small region. For example, when the shape in the XY plane of the small region is a square, it is possible to make a material that is located at one of the vertexes of this square the representative material.

FIG. 16 shows an example of a small region. The small region 102 shown in FIG. 16 is constituted from a round wire pattern portion 203 that occupies about ¼ of the area of the entire small region 102, a wire pattern portion 203 that is a thin lead line drawn out from the round portion, and a non-wire portion 204, which is the remaining portion of the small region 102. In the small region 102, the material located in the center is the material of the wire pattern portion 203, and so the material that represents this small region is determined to be the material of the wire pattern.

Next, the material constant selection portion 19 selects the material constant of the material that represents the respective small regions (Step S76), based on the material constant that that was input in the material constant data input step (Step S72). The material constant selection portion 19 selects the material constant of the representative material determined in Step S75 by referring to the material constant data input in Step S72. The representative material of the small region 102 shown in FIG. 16 is the material of the wire pattern. Accordingly, for example, the thermal conductivity of the wire material included in the material constant data is selected as the representative material constant of the small region 102.

The representative material determining portion 18 and the material constant selection portion 19 repeat the processing of Step S75 and Step S76 for all of the small regions.

When a representative material constant is obtained for each small region, the combining portion 7 obtains an equivalent material constant for the region in which a plurality of small regions are combined, based on the representative material constants of each small region (Step S77). The combining portion 7, for example, obtains an equivalent material constant for the region in which a plurality of small regions adjacent in the X axis direction, Y axis direction, or Z axis direction are combined for at least one direction.

The processing in which the combining portion 7 obtains an equivalent material constant for the region in which a plurality of adjacent small regions are combined is the same as the processing described using FIG. 17 and FIG. 18 in the above embodiment, so that description will be omitted here.

Figure 23:
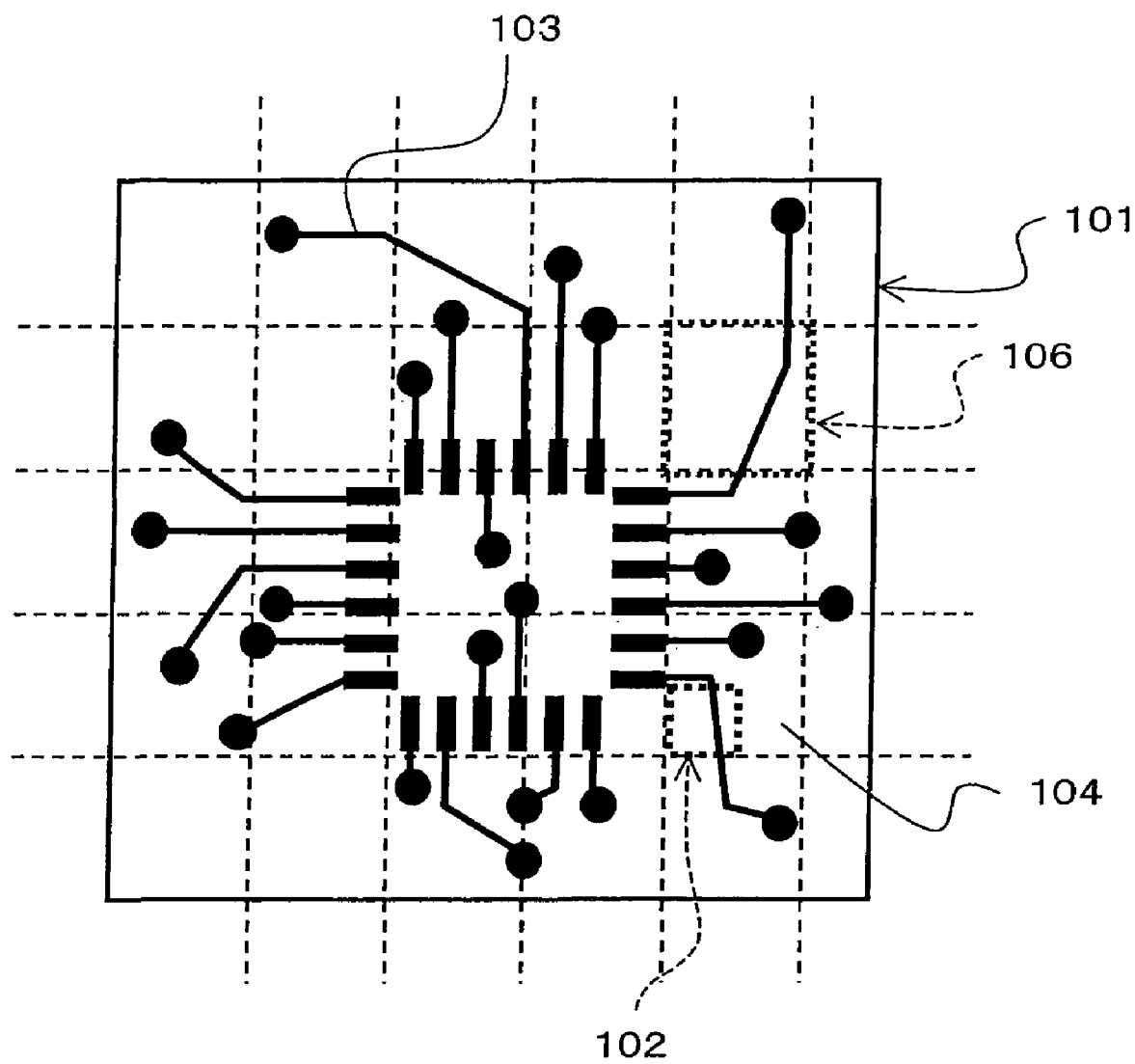
FIG. 23 shows an example of a medium region included in an electronic circuit board 101.
Figure 23:
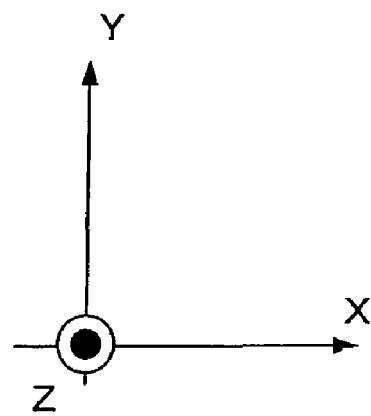

With the processing described using FIG. 17 and FIG. 18 in the above embodiment, by obtaining an equivalent material constant for the region in which a plurality of small regions are combined, it is possible to calculate an equivalent material constant for each of a plurality of medium regions included in the electronic circuit board 101, which are regions that are a portion of the electronic circuit board 101. FIG. 23 shows an example of a medium region included in the electronic circuit board 101. In FIG. 23, a region in the XY plane that has the size of four small regions is made one medium region. A medium region 106 is one of the medium regions.

In FIG. 23, four small regions are made one medium region, but it is preferable to change the size of the medium region as necessary. It is also possible to combine all of the small regions, and obtain one equivalent material constant for the entire electrical circuit board 101.

Also, for example, it is possible to omit the combining processing by the combining portion 7 for regions in which it is not necessary to obtain an equivalent material constant, such as the edge portions of the electronic circuit board 101 where there is not much wire pattern. By doing so, the calculation load for the equivalent material constant calculation is reduced.

In the present embodiment, by way of example it is assumed that all of the materials that constitute the wire pattern portion 103 are the same, and the thermal conductivities are also the same, but the wire pattern portion 103 also may be constituted from a plurality of materials with differing thermal conductivity. This is also true for the non-wire portion 104.

Also, in the present embodiment, a case was explained in which an equivalent thermal conductivity of the electronic circuit board is obtained. The equivalent material constant calculation system according to the present invention is not limited to an equivalent thermal conductivity calculation system of an electronic circuit board; it also may be used in a system that calculates an equivalent material constant of a structure that includes other composite materials. For example, it can be used in the calculation of an equivalent material constant of a semiconductor component that has a structure in which a semiconductor is provided in resin, a substrate that includes resin and glass, a sealant resin that includes resin and silica, a conductive adhesive that includes resin and silver, or the like.

Also, the equivalent material constant calculation according to the present invention is not limited to a system that calculates an equivalent thermal conductivity. For example, an equivalent material constant calculation system that calculates an equivalent electrical conductivity, equivalent dielectric constant, equivalent magnetic permeability, equivalent Young's modulus, or other material constants of composite materials is also included in the present invention.

Embodiment 6

Embodiment 6 is a design system that includes the equivalent material constant calculation system 100 of Embodiment 1-5. The design system according to the present embodiment is a system for designing a structure constituted from a plurality of materials.

Figure 24:
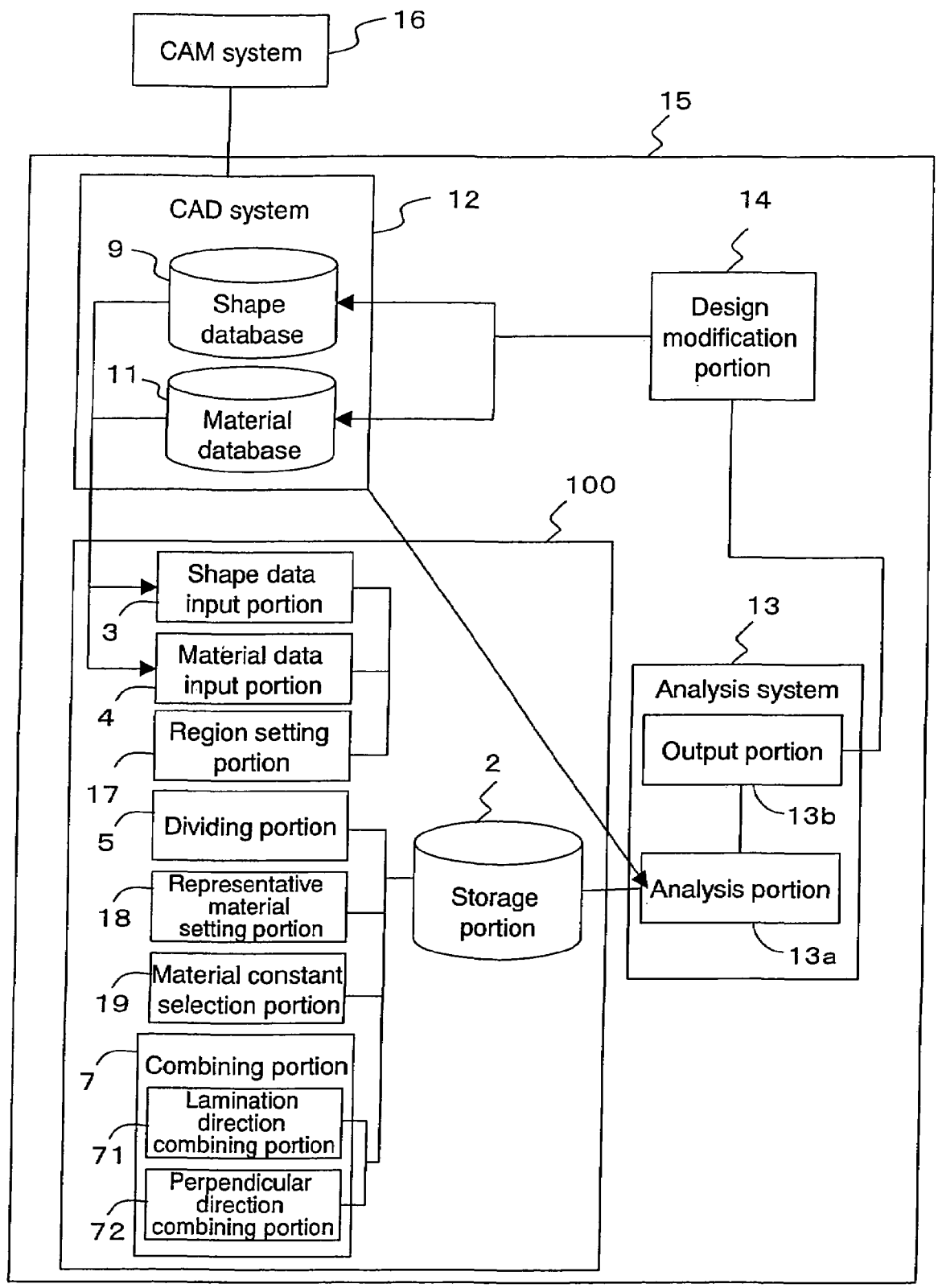
FIG. 24 is a functional block diagram that shows an example of the configuration of a design system 15.

FIG. 24 is a functional block diagram that shows an example of the configuration of a design system 15 according to the present embodiment. In the block diagram shown in FIG. 24, the same blocks as in the block diagram shown in FIG. 20 are given the same numerals, and that explanation is not repeated. Also, because the processing of the equivalent material constant calculation system 100 is the same as in Embodiment 5, that explanation is also omitted.

The design system 15 includes, in addition to the equivalent material constant calculation system 100, a CAD system 12, an analysis system 13, and a design modification portion 14.

The CAD system 12 designs a structure constituted from a plurality of materials, and stores that design data. Shape data and material constant data is included in the design data. The shape data is saved in a shape database 9, and the material constant data is saved in a material database 11.

The CAD system 12 is connected such that data communication with a CAM (Computer Aided Manufacturing) system 16 is possible. The CAD system 12 sends design data to the CAM system 16.

The CAM system 16 automatically manufactures a structure based on the design data received from the CAD system 12. The CAM system 16 is an automatic manufacturing system invoking a computer. In the CAM system 16, a computer transmits a work command to an automatic machine for manufacturing a structure (not shown in the figures).

The analysis system 13 includes an analysis portion 13a and an output portion 13b. The analysis portion 13a analyzes the flow of heat, pressure distribution, magnetic fields, or hydrokinetics in a structure by simulation, based on the equivalent material constant of the structure calculated by the equivalent material constant calculation system 100 and the design data created by the CAD system 12. The output portion 13b outputs the analysis results of the analysis portion 13a. The output portion 13b includes a function to send the analysis results to the design modification portion 14, and a function to print or display the analysis results such that they are understood by the designer. The function to print or display the analysis results is realized, for example, by a display or printer.

The design modification portion 14 modifies the design data saved in the CAD system 12, based on the analysis results received from the output portion 13b of the analysis system 13. Also, the design modification portion 14 includes a user interface for receiving a design data modification command from the designer. The design modification portion 14 modifies the design data saved in the CAD system 12, based on the design data modification command received from the designer.

Figure 25:
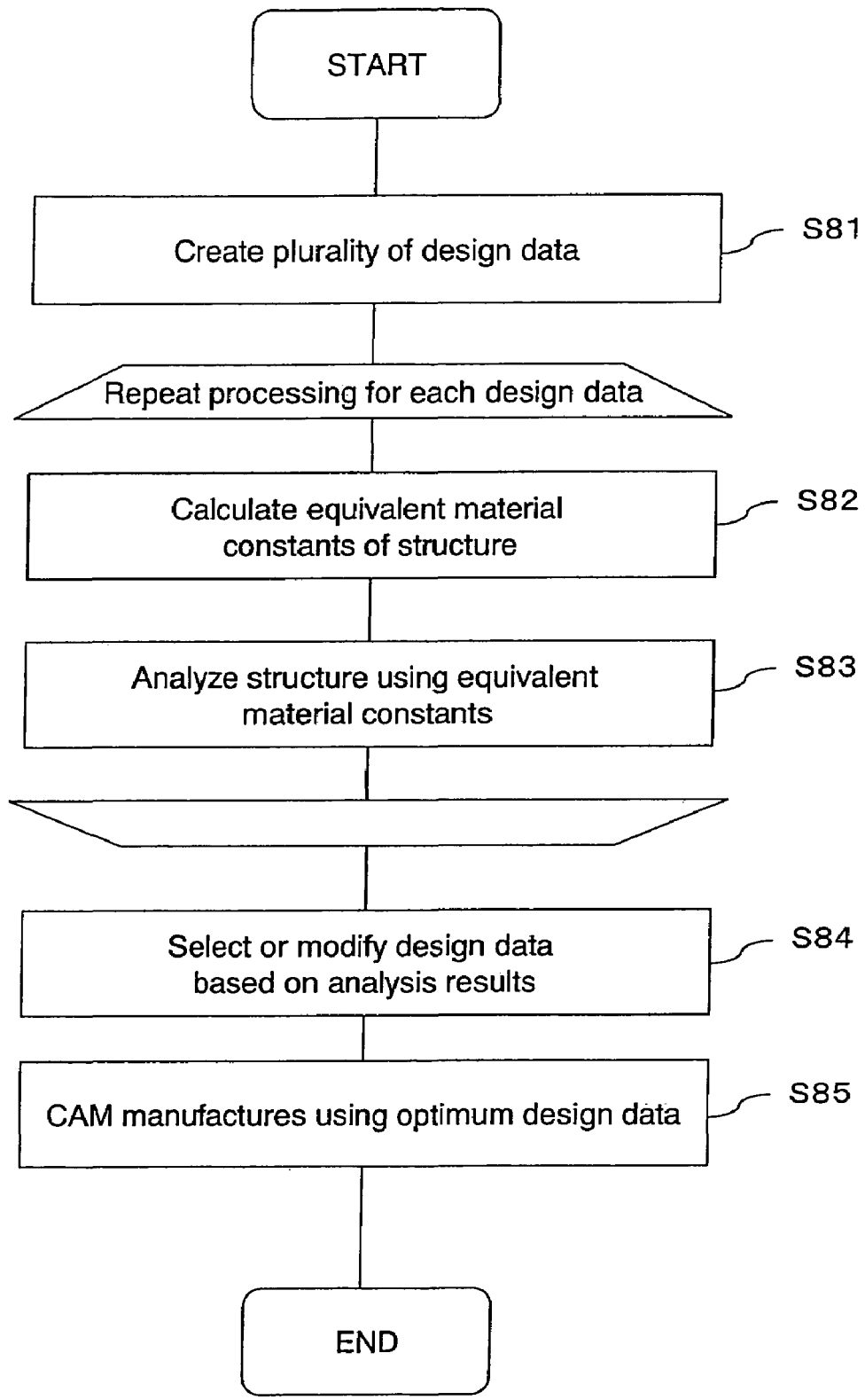
FIG. 25 is a flowchart that shows the flow of processing in which a design system 15 manufactures a structure.
Figure 26:
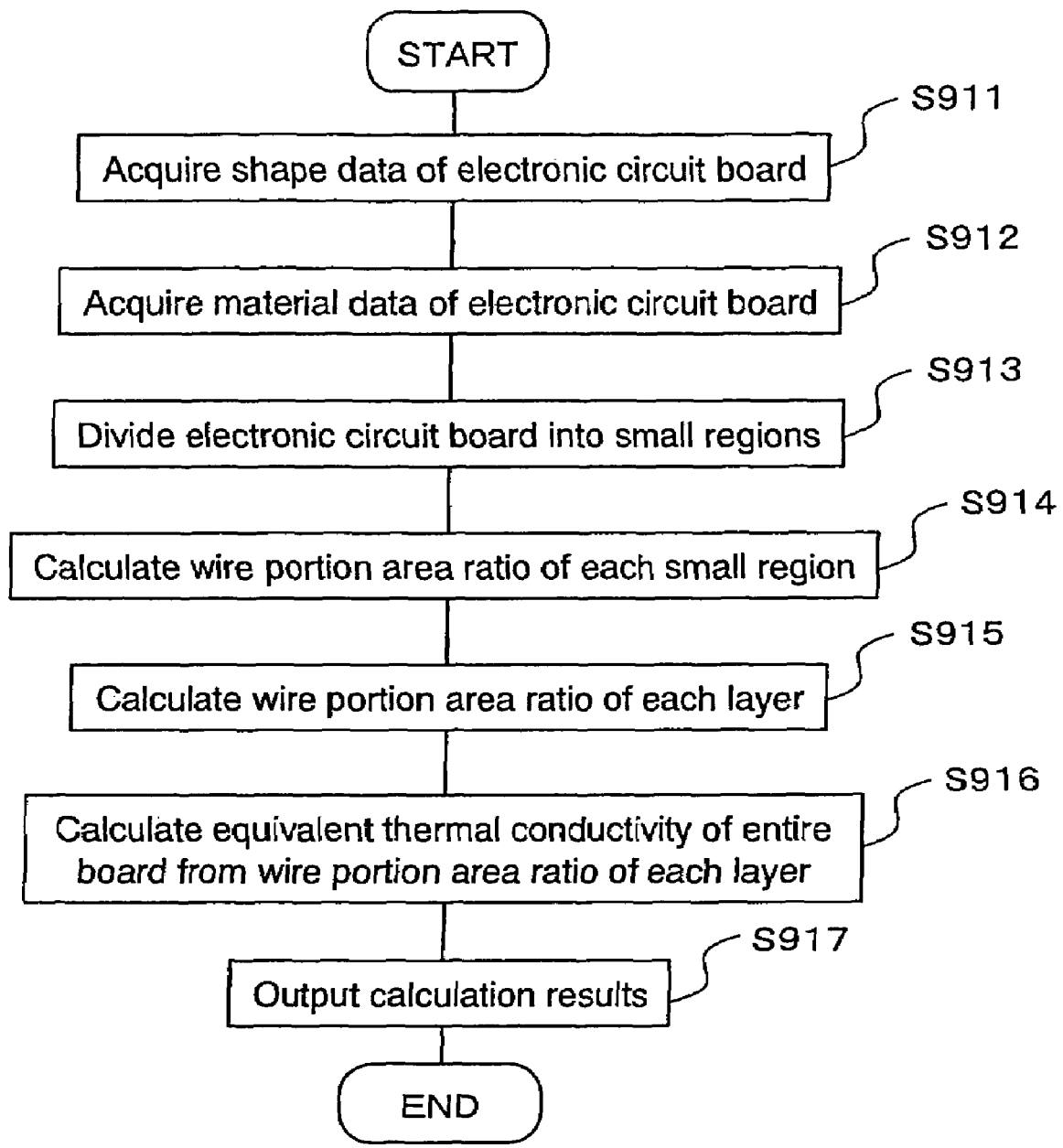
FIG. 26 shows an example of a conventional equivalent material constant calculation method.
Figure 27A:
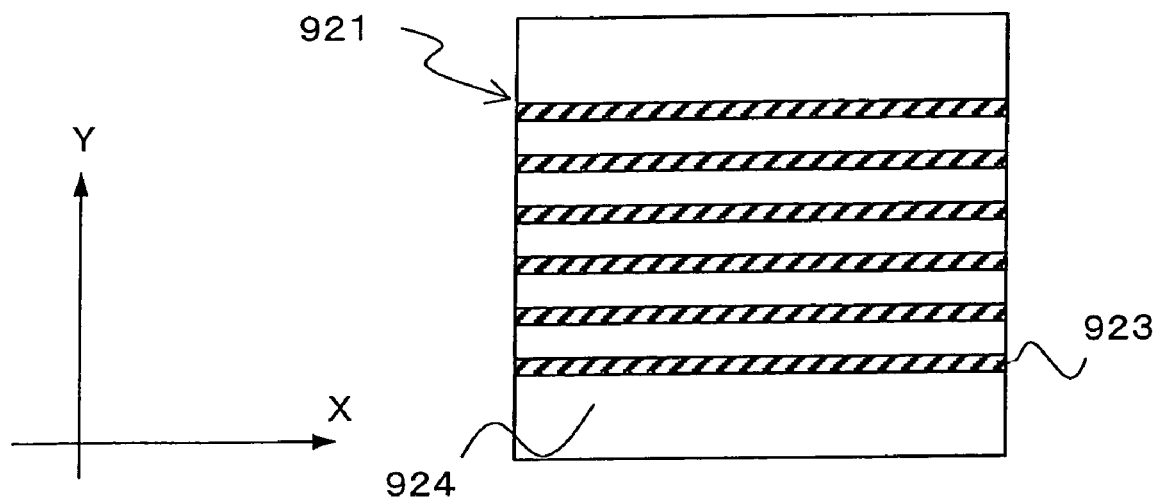
FIGS. 27A and 27B show examples of a wire pattern of an electronic circuit board.
Figure 27B:
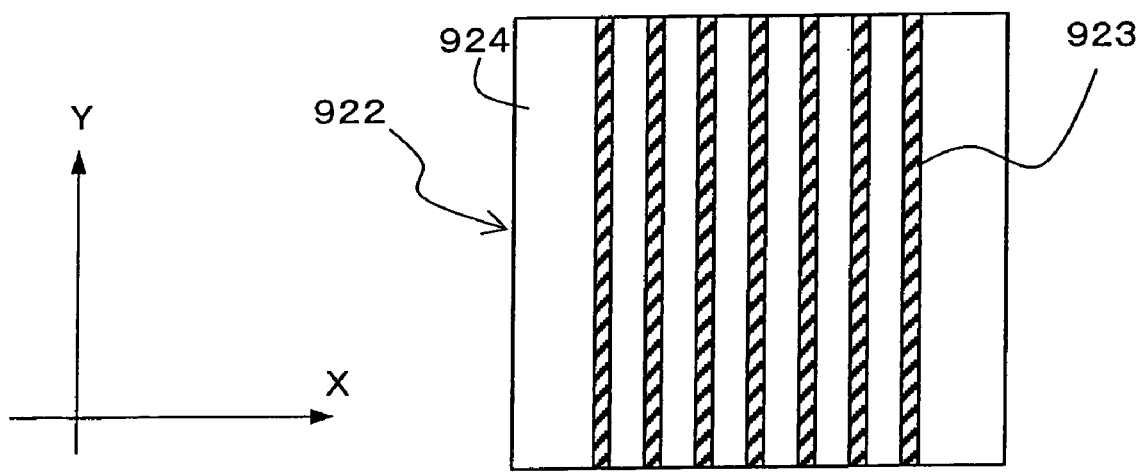

Following is a description of the method for designing and manufacturing a structure using the design system 15. FIG. 25 is a flowchart that shows the flow of processing in which the design system 15 manufactures a structure.

First, the CAD system 12 designs the structure (Step S81). For example, it creates design data with a plurality of different patterns for the same kind of structure. Shape data and material constant data are included in the design data created by the CAD system 12. Those are saved in the shape database 9 and the material database 11 of the CAD system 12.

Based on the plurality of design data created in Step S81, the equivalent material constant calculation system 100 calculates an equivalent material constant of the structure expressed by the respective design data (Step S82). The calculation method of the equivalent material constant is the same as the processing in Embodiment 5, and therefore is omitted here.

Based on the design data created in Step S81 and the equivalent material constant calculated in Step S82, the analysis portion 13a analyzes the flow of heat, pressure distribution, magnetic fields, or hydrokinetics in the structure expressed by the design data by simulation (Step S83). It is possible to use commercially available CAE (Computer Aided Engineering) software for the analysis processing. Using the analysis portion 13a, it is possible to investigate whether design specifications such as temperature, strength, and noise level of the structure are satisfied, or whether the permissible temperature and strength of the material of the structure are exceeded. The analysis processing by the analysis portion 13a is performed for each structure that the plurality of design data expresses.

The output portion 13b displays the analysis results so that they may be understood by the designer. Examples of analysis results for the flow of heat in the structure include a heat contour diagram on the surface or in a cross section of the structure, a graph in which position is plotted on the horizontal axis and temperature is plotted on the vertical axis, a temperature value at a predetermined position in the structure, or the like.

Also, the output portion 13b sends all or a part of the analysis results to the design modification portion 14. For example, the output portion 13b sends data that expresses the temperature in a specified portion of the structure, or the like, to the design modification portion 14 as analysis results.

Based on the analysis results of Step S83, the design modification portion 14 selects optimum design data from among the plurality of design data (Step S84). For example, the design modification portion 14, when the temperature distribution of the structure has been obtained as analysis results, selects design data for which the temperature at a particular portion of the structure does not exceed a certain value as the design data of the structure that is to be sent to the CAM system 16. Design data also can be selected that is judged to have passed not only heat analysis, but all of the analysis such as stress analysis, magnetic field analysis, and the like. Here, the selected design data is not necessarily one design data. The design modification portion 14 selects design data based on the analysis results, and so it is also possible to select design data that is not expected to generate defects even when manufactured by the CAM system 16.

The design modification portion 14 also can automatically modify the design data saved in the CAD system 12 based on the analysis results received from the output portion 13b.

The design modification portion 14 also may modify design data saved on the CAD system 12 based on a design data modification command from the designer. The designer can view the analysis results displayed by the output portion 13b and input a design modification command to the design modification portion 14.

Design data of a higher quality structure can be obtained due to the design data being modified by the design modification portion 14.

With the design modification portion 14, it is possible to perform the analysis processing of Steps S82 and S83 again for the modified or selected design data. By repeating the selection or modification of design data (Step S84) and the processing of Steps S82 and S83, design data of a high quality structure can be obtained.

The CAD system 12 sends the ultimately selected design data to the CAM system 16. The CAM system 16 creates a mask pattern for manufacturing the structure based on the design data sent from the CAD system 12 (Step S85). For example, a computer of the CAM system 16 reads the shape data included in the design data and creates a mask pattern having the shape that the shape data indicates.

The present invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

The present invention can be used as an equivalent material constant calculation system in which it is possible to calculate an equivalent material constant that takes into consideration the directionality of each electronic material that constitutes a structure, an equivalent material constant calculation program, an equivalent material constant calculation method, and a design system and manufacturing method of a structure for which those are used.

What is claimed is:

1. An equivalent material constant calculation system that calculates an equivalent material constant of a structure constituted by a plurality of materials, comprising:
  a shape data input portion that inputs shape data that expresses the shape of each material constituting the structure,
  a material data input portion that inputs material constant data that expresses a material constant of at least one of the materials constituting the structure,
  a dividing portion that divides the structure into a plurality of small regions, and
  a small region interior calculation portion that calculates equivalent material constants in the small regions,
  wherein the small region interior calculation portion expresses, based on the shape data and material constant data, an equivalent material constant for a region that is part of a small region with a function that includes a value in a variable that expresses a position in at least one direction in the small regions, and calculates equivalent material constants in the small region with respect to the at least one direction using the function, and
  wherein the small region interior calculation portion comprises:
  a boundary function generating portion that sets a coordinate in the direction of one coordinate axis to u in an orthogonal coordinate system that has been set for the structure and generates, based on the shape data, a boundary function F(u) that expresses a boundary between the materials in a small region,
  a section setting portion that sets one or more sections for u in the small region according to a domain of the boundary function F(u),
  a section interior calculation portion that creates, in the section, based on the function F(u) and the material constant data, a function that expresses a position where the material constant is applied, and obtains an equivalent material constant of the coordinate axis direction in the section by integrating the function in the section, and
  an equivalent material constant generating portion that, based on a section equivalent material constant of each section obtained by the section interior calculation portion, obtains an equivalent material constant of the coordinate axis direction in the small region.

2. The equivalent material constant calculation system according to claim 1, further comprising a combining portion that obtains, based on the equivalent material constant for the small region, an equivalent material constant for a region in which a plurality of small regions that are adjacent are combined.

3. The equivalent material constant calculation system according to claim 2, wherein the combining portion obtains the equivalent material constant for a region in which a plurality of the small regions that are adjacent are combined, by deeming the equivalent material constant for each of the plurality of small regions to be a mutually connected resistance, and obtaining a combined resistance.

4. A design system that includes the equivalent material constant calculation system according to claim 1, comprising:
   a storage portion that stores design data of the structure including the shape data and the material constant data,
   an analysis portion that analyzes and outputs the flow of heat, stress distribution, electromagnetic fields, or hydrokinetics of the structure, by simulation based on the equivalent material constant of the structure calculated by the equivalent material constant calculation system and the design data, and
   a design modification portion that modifies the design data of the storage portion based on a command to modify the design data from a designer.

5. An equivalent material constant calculation system that calculates an equivalent material constant of a structure constituted by a plurality of materials, comprising:
   a shape data input portion that inputs shape data that expresses the shape of each material constituting the structure,
   a material data input portion that inputs material constant data that expresses a material constant of at least one of the materials constituting the structure,
   a dividing portion that divides the structure into a plurality of small regions, and
   a small region interior calculation portion that calculates equivalent material constants in the small regions,
   wherein the small region interior calculation portion expresses, based on the shape data and material constant data, an equivalent material constant for a region that is part of a small region with a function that includes a value in a variable that expresses a position in at least one direction in the small regions, and calculates equivalent material constants in the small region with respect to the at least one direction using the function, and
   wherein the small region interior calculation portion comprises:
   a minimum region material constant generating portion that further divides the small regions into a plurality of minimum regions along one or more directions, and obtains an equivalent material constant for each minimum region based on the shape data and the material constant data,
   a spectrum calculation portion that obtains a frequency spectrum in each minimum region by performing a Fourier transformation of the distribution of the equivalent material constant of the minimum regions in the small region in one or more directions, and
   an equivalent material constant generating portion that obtains an equivalent material constant for the small region in the one or more directions, based on the frequency spectrum in each of the minimum regions.

6. The equivalent material constant calculation system according to claim 5, further comprising a combining portion that obtains, based on the equivalent material constant for the small region, an equivalent material constant for a region in which a plurality of small regions that are adjacent are combined.

7. A design system that includes the equivalent material constant calculation system according to claim 5, comprising:
   a storage portion that stores design data of the structure including the shape data and the material constant data,
   an analysis portion that analyzes and outputs the flow of heat, stress distribution, electromagnetic fields, or hydrokinetics of the structure, by simulation based on the equivalent material constant of the structure calculated by the equivalent material constant calculation system and the design data, and
   a design modification portion that modifies the design data of the storage portion based on a command to modify the design data from a designer.

8. A storage medium storing an equivalent material constant calculation program that allows a computer to execute processing that calculates an equivalent material constant of a structure constituted by a plurality of materials, the processing comprising:
   shape data input Processing that inputs shape data that expresses the shape of each material constituting the structure,
   material data input processing that inputs material constant data that expresses a material constant of at least one of the materials constituting the structure,
   dividing processing that divides the structure into a plurality of small regions, and
   small region interior calculation processing that calculates equivalent material constants in the small regions,
   wherein the small region interior calculation processing expresses, based on the shape data and material constant data, an equivalent material constant in a region that is a portion of a small region with a function that includes a value in a variable that expresses a position in at least one direction in the small regions, and calculates an equivalent material constant for the small region with respect to the at least one direction using the function, and
   wherein the small region interior calculation processing includes:
   boundary function generating processing that sets a coordinate in the direction of one coordinate axis to u in an orthogonal coordinate system that has been set for the structure, and generates, based on the shape data, a boundary function F(u) that expresses a boundary between the materials in a small region,
   section setting processing that sets one or more sections for u in the small region according to a domain of the boundary function F(u),
   section interior calculation processing that creates, in the section, based on the function F(u) and the material constant data, a function that expresses a position where the material constant is applied, and obtains an equivalent material constant of the coordinate axis direction in the section by integrating the function in the section, and
   equivalent material constant generating processing that, based on a section equivalent material constant of each section obtained by the section interior calculation portion, obtains an equivalent material constant of the coordinate axis direction in the small region.

9. A storage medium storing an equivalent material constant calculation program that allows a computer to execute processing that calculates an equivalent material constant of a structure constituted by a plurality of materials, the processing comprising:
   shape data input processing that inputs shape data that expresses the shape of each material constituting the structure, material data input processing that inputs material constant data that expresses a material constant of at least one of the materials constituting the structure, dividing processing that divides the structure into a plurality of small regions, and small region interior calculation processing that calculates equivalent material constants in the small regions, wherein the small region interior calculation processing expresses, based on the shape data and material constant data, an equivalent material constant in a region that is a portion of a small region with a function that includes a value in a variable that expresses a position in at least one direction in the small regions, and calculates an equivalent material constant for the small region with respect to the at least one direction using the function, and wherein the small region interior calculation processing includes:

minimum region material constant generating processing that further divides a small regions into a plurality of minimum regions along one or more directions, and obtains an equivalent material constant for each minimum region based on the shape data and the material constant data, spectrum calculation processing that obtains a frequency spectrum in each minimum region by performing a Fourier transformation of the distribution of the equivalent material constant of the minimum regions in the small region in one or two or more directions, and equivalent material constant generating processing that obtains an equivalent material constant for the small region in the one or more directions, based on the frequency spectrum in each of the minimum regions.

10. An equivalent material constant calculation method that calculates an equivalent material constant of a structure constituted by a plurality of materials using a computer comprising, a shape data input step in which a shape data input portion provided by the computer inputs shape data that expresses the shape of each material constituting the structure, a material data input step in which a material data input portion provided by the computer inputs material constant data that expresses a material constant of at least one of the materials constituting the structure, a dividing step in which a dividing portion provided by the computer divides the structure into a plurality of small regions, and a small region interior calculation step in which a small region interior calculation portion provided by the computer calculates equivalent material constants in the small regions, wherein the small region interior calculation step, in which a small region interior calculation portion expresses, based on the shape data and material constant data, an equivalent material constant for a region that is a portion of a small region with a function that includes value in a variable a that expresses a location in the small region in at least one direction and calculates an equivalent material constant for the small region with respect to the at least one direction using the function, and wherein the small region interior calculation step comprises:

a boundary function generating step of setting a coordinate in the direction of one coordinate axis to u in an orthogonal coordinate system that has been set for the structure, and generating, based on the shape data, a boundary function F(u) that expresses a boundary between the materials within the small region, a section setting step of setting one or more sections for u in the small region according to a domain of the boundary function F(u), a section interior calculation step of creating a function, in the section, that expresses a position where the material constant is applied, based on the function F(u) and the material constant data, and obtaining an equivalent material constant of the coordinate axis direction in the section by integrating the function in the section, and an equivalent material constant generating step of obtaining an equivalent material constant of the coordinate axis direction in the small region, based on a section equivalent material constant of each section which is obtained in the section interior calculation step.

11. A structure manufacturing method that, using a computer that can access a storage device in which a plurality of design data of a structure constituted by a plurality of materials is stored, manufactures the structure, comprising:

a calculating step in which the computer calculates an equivalent material constant of the structure by the equivalent material constant calculation method according to claim 10, an analysis step in which an analysis portion provided by the computer analyzes the flow of heat, stress distribution, electromagnetic field, or hydrokinetics of the structure, by simulation based on the equivalent material constant and the design data, a design data selection step in which a design data selection portion provided by the computer selects design data from among the plurality of design data based on the analysis results obtained by the analysis step for a structure expressed by the plurality of design data stored in the storage device, and a manufacturing step in which a CAM, connected such that data communications are possible with the computer, manufactures a structure based on the design data selected by the design data selection step.

12. An equivalent material constant calculation method that calculates an equivalent material constant of a structure constituted by a plurality of materials using a computer comprising, a shape data input step in which a shape data input portion provided by the computer inputs shape data that expresses the shape of each material constituting the structure, a material data input step in which a material data input portion provided by the computer inputs material constant data that expresses a material constant of at least one of the materials constituting the structure, a dividing step in which a dividing portion provided by the computer divides the structure into a plurality of small regions, and a small region interior calculation step in which a small region interior calculation portion provided by the computer calculates equivalent material constants in the small regions, wherein the small region interior calculation step, in which a small region interior calculation portion expresses, based on the shape data and material constant data, an equivalent material constant for a region that is a portion of a small region with a function that includes value in a variable a that expresses a location in the small region in at least one direction and calculates an equivalent material constant for the small region with respect to the at least one direction using the function, and wherein the small region interior calculation step comprises:
- a minimum region material constant generating step of further dividing a small regions into a plurality of minimum regions along one or more directions, and obtaining an equivalent material constant for each minimum region, based on the shape data and the material constant data,
- a spectrum calculation step of obtaining a frequency spectrum in each minimum region by performing a Fourier transformation of the distribution of the equivalent material constant of the minimum regions in the small region in one or more directions, and
- an equivalent material constant generating step of obtaining an equivalent material constant for the small region in the one or more directions, based on the frequency spectrum in each of the minimum regions.

13. A structure manufacturing method that, using a computer that can access a storage device in which a plurality of design data of a structure constituted by a plurality of materials is stored, manufactures the structure, comprising:
- a calculating step in which the computer calculates an equivalent material constant of the structure by the equivalent material constant calculation method according to claim 12,
- an analysis step in which an analysis portion provided by the computer analyzes the flow of heat, stress distribution, electromagnetic field, or hydrokinetics of the structure, by simulation based on the equivalent material constant and the design data,
- a design data selection step in which a design data selection portion provided by the computer selects design data from among the plurality of design data based on the analysis results obtained by the analysis step for a structure expressed by the plurality of design data stored in the storage device, and
- a manufacturing step in which a CAM, connected such that data communications are possible with the computer, manufactures a structure based on the design data selected by the design data selection step.

14. An equivalent material constant calculation system that calculates an equivalent material constant of a structure constituted by a plurality of materials, comprising:
- a shape data input portion that inputs shape data that expresses the shape of each material constituting the structure,
- a material data input portion that inputs material constant data that expresses a material constant of at least one of the materials constituting the structure,
- a dividing portion that divides the structure into a plurality of small regions, and
- a small region interior calculation portion that calculates equivalent material constants in the small regions, wherein
- the small region interior calculation portion calculates an area of each material included in the small region based on the shape data, obtains a slope of a line that expresses a boundary between the materials relative to a predetermined direction, and calculates an equivalent material constant for the small region based on the slope, the area, and the material constant data.

15. The equivalent material constant calculation system according to claim 14, further comprising a combining portion that obtains an equivalent material constant for a region in which a plurality of small regions that are adjacent arc combined, based on the equivalent material constant for the small region.

16. The equivalent material constant calculation system according to claim 15, wherein the combining portion obtains the equivalent material constant for a region in which a plurality of the small regions that are adjacent are combined, by deeming the equivalent material constant for each of the plurality of small regions to be a mutually connected resistance, and obtaining a combined resistance.

17. A design system that includes the equivalent material constant calculation system according to claim 14, comprising:
- a storage portion that stores design data of the structure including the shape data and the material constant data,
- an analysis portion that analyzes and outputs the flow of heat, stress distribution, electromagnetic fields, or hydrokinetics of the structure, by simulation based on the equivalent material constant of the structure calculated by the equivalent material constant calculation system and the design data, and
- a design modification portion that modifies the design data of the storage portion based on a command to modify the design data from a designer.

18. An equivalent material constant calculation method that calculates an equivalent material constant of a structure constituted by a plurality of materials using a computer, comprising:
- a shape data input step in which a shape data input portion provided by the computer inputs shape data that expresses the shape of each material constituting the structure,
- a material data input step in which a material data input portion provided by the computer inputs material constant data that expresses a material constant of at least one of the materials constituting the structure,
- a dividing step in which a dividing portion provided by the computer divides the structure into a plurality of small regions, and
- a small region interior calculation step in which a small region interior calculation portion provided by the computer calculates equivalent material constants in the small regions, wherein
- in the small region interior calculation step, the small region interior calculation portion calculates an area of each material included in the small region based on the shape data, obtains a slope of a line that expresses a boundary between the materials relative to a predetermined direction, and calculates an equivalent material constant for the small region based on the slope, the area, and the material constant data.

19. A structure manufacturing method that, using a computer that can access a storage device in which a plurality of design data of a structure constituted by a plurality of materials is stored, manufactures the structure, comprising:
- a calculating step in which the computer calculates an equivalent material constant of the structure by the equivalent material constant calculation method according to claim 18,
- an analysis step in which an analysis portion provided by the computer analyzes the flow of heat, stress distribution, electromagnetic field, or hydrokinetics of the structure, by simulation based on the equivalent material constant and the design data,
- a design data selection step in which a design data selection portion provided by the computer selects design data from among the plurality of design data based on the analysis results obtained by the analysis step for a structure expressed by the plurality of design data stored in the storage device, and a manufacturing step in which a CAM, connected such that data communications are possible with the computer, manufactures a structure based on the design data selected by the design data selection portion.

20. A storage medium storing an equivalent material constant calculation program that allows a computer to execute processing that the processing calculates an equivalent material constant of a structure constituted by a plurality of materials, the processing comprising:

a shape data input processing that inputs shape data that expresses the shape of each material constituting the structure, a material data input processing that inputs material constant data that expresses a material constant of at least one of the materials constituting the structure, a dividing processing that divides the structure into a plurality of small regions, and a small region interior calculation processing that calculates equivalent material constants in the small regions, wherein the small region interior calculation processing calculates an area of each material included in the small region based on the shape data, obtains a slope of a line that expresses a boundary between the materials relative to a predetermined direction, and calculates an equivalent material constant for the small region based on the slope, the area, and the material constant data.

* * * * *

UNITED STATES PATENT AND TRADEMARK OFFICE
CERTIFICATE OF CORRECTION

PATENT NO. : 7,548,792 B2
APPLICATION NO. : 12/077879
DATED : June 16, 2009
INVENTOR(S) : Kumano et al.

It is certified that error appears in the above-identified patent and that said Letters Patent is hereby corrected as shown below:

Column 44, line 20 (claim 8): "Processing" should read --processing--.
Column 45, line 19 (claim 9): "regions" should read --region--.
Column 47, line 65 (claim 15): "adjacent arc" should read --adjacent are--.

Signed and Sealed this

Twenty-sixth Day of January, 2010

David J. Kappos
*Director of the United States Patent and Trademark Office*